(12) United States Patent
Rapoport

(10) Patent No.: US 10,499,830 B2
(45) Date of Patent: *Dec. 10, 2019

(54) PREMATURE NEONATE LIFE SUPPORT ENVIRONMENTAL CHAMBER FOR USE IN MRI/NMR DEVICES

(71) Applicant: Aspect Imaging Ltd., Shoham (IL)

(72) Inventor: Uri Rapoport, Moshav Ben Shemen (IL)

(73) Assignee: Aspect Imaging Ltd., Shoham (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,839

(22) Filed: Dec. 2, 2016

(65) Prior Publication Data

US 2017/0188879 A1    Jul. 6, 2017

Related U.S. Application Data

(63) Continuation-in-part of application No. 13/808,476, filed as application No. PCT/IL2011/000537 on Jul.
(Continued)

(51) Int. Cl.
*A61B 5/05* (2006.01)
*A61B 5/055* (2006.01)
(Continued)

(52) U.S. Cl.
CPC .......... *A61B 5/0555* (2013.01); *A61B 5/6887* (2013.01); *A61G 11/00* (2013.01);
(Continued)

(58) Field of Classification Search
CPC ............ A61B 2503/045; A61B 5/0555; A61G 11/002; G01R 33/307; G01R 33/422
See application file for complete search history.

(56) References Cited

U.S. PATENT DOCUMENTS

| 1,900,342 A | 3/1933 | Hess |
| 2,638,087 A | 5/1953 | Livsey |

(Continued)

FOREIGN PATENT DOCUMENTS

| CA | 2815746 | 5/2012 |
| CN | 2448344 | 9/2001 |

(Continued)

OTHER PUBLICATIONS

Incubator Enables MRI Scans on Preemies for Preventing Birth Asphyxia, Science Daily, http://web.archive.org/web/20130303154220/http://www.sciencedaily.com/videos/2005/2011-inside_the_preemie_brain.htm.
(Continued)

*Primary Examiner* — Christopher L Cook
(74) *Attorney, Agent, or Firm* — Loeb & Loeb LLP

(57) ABSTRACT

A magnetic resonance system, useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar. At least a portion of the cart and the MRD are configured to fit together such that at least a portion of the incubator is reversibly housed within the MRD, and further at least a portion of the base is reversibly housed within at least one recess.

10 Claims, 15 Drawing Sheets

Related U.S. Application Data 7, 2011, now abandoned, said application No. 15/367, 839 is a continuation-in-part of application No. 14/892,207, filed as application No. PCT/IL2014/050450 on May 21, 2014.

(60) Provisional application No. 61/361,936, filed on Jul. 7, 2011, provisional application No. 61/994,901, filed on May 18, 2014.

(51) Int. Cl.
*G01R 33/30* (2006.01)
*A61B 5/00* (2006.01)
*A61G 11/00* (2006.01)
*G01R 33/38* (2006.01)

(52) U.S. Cl.
CPC ...... *G01R 33/307* (2013.01); *A61B 2503/045* (2013.01); *G01R 33/3806* (2013.01)

(56) References Cited

U.S. PATENT DOCUMENTS

| | | | |
|---|---|---|---|
| 2,708,927 A | 5/1955 | Dixon et al. | |
| 3,012,836 A | 12/1961 | Smith et al. | |
| 3,315,671 A | 4/1967 | Creelman | |
| 3,470,866 A | 10/1969 | Gittelson | |
| 3,655,178 A | 4/1972 | Vezina | |
| 3,710,791 A | 1/1973 | Deaton | |
| 3,920,000 A | 11/1975 | Atherton et al. | |
| 4,161,172 A | 7/1979 | Pickering | |
| 4,509,505 A | 4/1985 | Mercey et al. | |
| 4,567,894 A | 2/1986 | Bergman | |
| 4,712,263 A | 12/1987 | Pronzinski | |
| 4,750,474 A | 6/1988 | Dukhan et al. | |
| 4,936,824 A | 6/1990 | Koch et al. | |
| 5,038,515 A | 8/1991 | Moorhead | |
| 5,059,906 A | 10/1991 | Yamanaka | |
| 5,100,375 A | 3/1992 | Koch | |
| 5,402,543 A | 4/1995 | Dietrich et al. | |
| 5,446,934 A | 9/1995 | Frazier | |
| 5,509,159 A | 4/1996 | Du-bois | |
| 5,534,669 A | 7/1996 | Schroeder et al. | |
| 5,759,149 A | 6/1998 | Goldberg et al. | |
| 5,797,833 A | 8/1998 | Kobayashi et al. | |
| 5,800,335 A | 9/1998 | Koch et al. | |
| 5,817,003 A | 10/1998 | Moll et al. | |
| 5,917,324 A | 6/1999 | Leussler | |
| 5,943,716 A | 8/1999 | Chu | |
| 5,971,913 A | 10/1999 | Newkirk et al. | |
| 6,036,634 A | 3/2000 | Goldberg et al. | |
| 6,155,970 A | 12/2000 | Dykes et al. | |
| 6,231,499 B1 | 5/2001 | Jones | |
| D446,675 S | 8/2001 | Straub | |
| 6,317,618 B1 | 11/2001 | Livni et al. | |
| 6,409,654 B1 | 6/2002 | McClain et al. | |
| 6,433,548 B1 | 8/2002 | Furuta | |
| 6,471,634 B1 | 10/2002 | Dykes et al. | |
| 6,511,414 B1 | 1/2003 | Hamsund | |
| 6,611,702 B2 | 8/2003 | Rohling et al. | |
| 6,641,521 B2 | 11/2003 | Kolarovic | |
| 6,666,816 B2 | 12/2003 | Mountain | |
| RE38,453 E | 3/2004 | Lessard et al. | |
| 6,776,527 B1 | 8/2004 | Tybinkowski et al. | |
| 6,860,272 B2 | 3/2005 | Carter et al. | |
| 6,992,486 B2 | 1/2006 | Srinivasan | |
| 7,255,671 B2 | 8/2007 | Boone et al. | |
| 7,278,962 B2 | 10/2007 | Lönneker-Lammers | |
| D567,948 S | 4/2008 | Tierney et al. | |
| 7,482,558 B2 | 1/2009 | Koch | |
| 7,599,728 B2 | 10/2009 | Feenan | |
| 7,719,279 B2 | 5/2010 | Rapoport | |
| 7,784,121 B2 | 8/2010 | Ahlman | |
| 8,147,396 B2 | 4/2012 | Srinivasan | |
| 8,194,866 B2 | 6/2012 | Smith | |
| 8,217,653 B2 | 7/2012 | Vaughan | |
| 8,390,288 B2 | 3/2013 | Graesslin et al. | |
| 8,807,084 B2 | 8/2014 | Rapoport et al. | |
| 8,851,018 B2 | 10/2014 | Rapoport et al. | |
| 8,896,310 B2 | 11/2014 | Rapoport | |
| 2001/0049465 A1 | 12/2001 | Goldberg et al. | |
| 2002/0072648 A1 | 6/2002 | Dykes et al. | |
| 2002/0123681 A1 | 9/2002 | Zuk et al. | |
| 2002/0143233 A1 | 10/2002 | Donnelly et al. | |
| 2002/0173696 A1 | 11/2002 | Kolarovic et al. | |
| 2002/0173717 A1 | 11/2002 | Rohling et al. | |
| 2003/0088175 A1* | 5/2003 | Branch | G01R 33/422 600/410 |
| 2004/0030241 A1 | 2/2004 | Green et al. | |
| 2004/0034273 A1 | 2/2004 | Boris | |
| 2004/0133064 A1 | 7/2004 | Castillon Levano et al. | |
| 2004/0186341 A1* | 9/2004 | McDermott | G16H 40/63 600/22 |
| 2004/0236174 A1 | 11/2004 | Boone et al. | |
| 2004/0236175 A1* | 11/2004 | Boone | A61B 5/02055 600/22 |
| 2005/0004422 A1 | 1/2005 | Caspary et al. | |
| 2005/0020906 A1* | 1/2005 | Seijger | A61B 5/0555 600/415 |
| 2005/0038314 A1 | 2/2005 | Falk | |
| 2005/0113668 A1 | 5/2005 | Srinivasan | |
| 2006/0079730 A1 | 4/2006 | Getsla | |
| 2007/0232894 A1 | 10/2007 | Feenan | |
| 2008/0163425 A1 | 7/2008 | White | |
| 2009/0044335 A1 | 2/2009 | Brewin et al. | |
| 2009/0237077 A1 | 9/2009 | Vaughan | |
| 2010/0004502 A1 | 1/2010 | Honma et al. | |
| 2010/0168502 A1 | 7/2010 | Delaporte et al. | |
| 2010/0172468 A1 | 7/2010 | Gregerson | |
| 2010/0198047 A1 | 8/2010 | Zagorchev et al. | |
| 2010/0236426 A1 | 9/2010 | Stewart et al. | |
| 2010/0315085 A1 | 12/2010 | Brown et al. | |
| 2011/0048424 A1 | 3/2011 | Radko | |
| 2011/0113555 A1 | 5/2011 | Smith | |
| 2011/0125010 A1 | 5/2011 | Vaquero Lopez et al. | |
| 2011/0160521 A1 | 6/2011 | Khodak et al. | |
| 2011/0162652 A1 | 7/2011 | Rapoport | |
| 2011/0186049 A1 | 8/2011 | Rapoport | |
| 2011/0234347 A1 | 9/2011 | Rapoport | |
| 2011/0304333 A1 | 12/2011 | Rapoport | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0119742 A1 | 5/2012 | Rapoport | |
| 2012/0126814 A1 | 5/2012 | Fischer et al. | |
| 2012/0140899 A1 | 6/2012 | Bailey et al. | |
| 2013/0079624 A1 | 3/2013 | Rapoport | |
| 2013/0109956 A1 | 5/2013 | Rapoport | |
| 2013/0150656 A1* | 6/2013 | Falk | A61B 5/0555 600/22 |
| 2013/0204074 A1 | 8/2013 | Belval et al. | |
| 2013/0204617 A1 | 8/2013 | Kuo et al. | |
| 2013/0237803 A1 | 9/2013 | Rapoport | |
| 2013/0267765 A1 | 10/2013 | Rapoport | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2013/0334439 A1 | 12/2013 | Etters | |
| 2014/0003614 A1 | 1/2014 | Levitov et al. | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0055136 A1 | 2/2014 | Leussler et al. | |
| 2014/0078301 A1 | 3/2014 | Fazzi et al. | |
| 2014/0098934 A1 | 4/2014 | Kondo | |
| 2014/0099010 A1 | 4/2014 | Rapoport | |
| 2014/0103747 A1 | 4/2014 | Rapoport | |
| 2014/0117989 A1 | 5/2014 | Rapoport | |
| 2014/0128725 A1 | 5/2014 | Rapoport | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |

(56) References Cited

U.S. PATENT DOCUMENTS

| | | |
|---|---|---|
| 2014/0158062 A1 | 6/2014 | Rapoport et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0354279 A1* | 12/2014 | Dumoulin ............ G01R 33/422 324/318 |
| 2014/0357981 A1 | 12/2014 | Dumoulin |
| 2014/0364722 A1* | 12/2014 | Dumoulin ............ A61B 5/0555 600/415 |
| 2014/0378821 A1 | 12/2014 | Rapoport |
| 2014/0378825 A1 | 12/2014 | Rapoport et al. |
| 2015/0059655 A1 | 3/2015 | Rapoport |
| 2015/0137812 A1 | 5/2015 | Rapoport |
| 2015/0141799 A1 | 5/2015 | Rapoport et al. |
| 2015/0065788 A1 | 6/2015 | Rapoport |
| 2016/0030264 A1 | 2/2016 | Lehmann et al. |
| 2016/0081582 A1 | 3/2016 | Rapoport |

FOREIGN PATENT DOCUMENTS

| | | |
|---|---|---|
| CN | 102551719 A | 7/2012 |
| DE | 19617739 | 6/1997 |
| EP | 1132072 | 9/2001 |
| EP | 2581071 | 4/2013 |
| IL | 226488 | 7/2016 |
| JP | 2007252741 | 10/2007 |
| JP | 2010178857 | 8/2010 |
| WO | WO1998/048756 | 11/1998 |
| WO | WO9921526 | 5/1999 |
| WO | WO2008137003 | 11/2008 |
| WO | WO2010054457 | 5/2010 |
| WO | WO2010/125559 | 11/2010 |
| WO | WO2011/001429 | 1/2011 |
| WO | WO2011109761 | 9/2011 |
| WO | WO2012/143825 | 10/2012 |
| WO | WO2013/115847 | 8/2013 |
| WO | WO2014/188426 | 11/2014 |

OTHER PUBLICATIONS

Science Museum, "Fast Forward: 20 ways F1 is changing our world-Baby Pod II", uploaded Apr. 7, 2009, accessed online on May 26, 2016 at https://www.youtube.com/watch?v=KyZVhPWbWqo.

Advance Healthcare Technology, "Baby Pod II: Infant Transport Device", pp. 1-6, accessed online on May 26, 2016.

Advance Healthcare Technology, "Baby Pod II: Operating & Maintenance Manual", revised Jan. 2011, pp. 1-14.

Antonucci, et al., The infant incubator in the neonatal intensive care unit: unresolved issues and future developments, J. Perinat. Med. 37(2009), 587-598.

Ferris et al., The design of neonatal incubators: a systems-oriented, human centered approach, J. Perinatology, 2013, 33, S24-S31.

Kitterman et al., Catheterization of umbilical vessels in newborn infants, Pediatric Clinics of North America, vol. 17, No. 4, Nov. 1970, 895-912.

Paley et al., An MR-compatible neonatal incubator, The British Journal of Radiology, 85, 2012, 952-958.

American National Standard, Medical Electrical Equipment—Parts 2-19: Particular requirements for the basic safety and essential performance of infant incubators, Association for the advancement of medical instrumentation, ANSI/AAI/IEC 60601-2-19:2009, pp. 1-19.

Jenkins, S., ScanPod, BabyPod-Products-ScanPod. 2002-2011 Advance Healthcare Technology. ltd., internet website http://babypod.com:80/products/scanpod.php.

Knutson, Allysa Jennie, Acceptable noise levels for neonates in the neonatal intensive care unit, A Capstone Project submitted in partial fulfillment of the requirements for the degree of: Doctor of Audiology, Washington University School of Medicine Program in Audiology and Communication Sciences, May 17, 2013, pp. 1-59.

Liu, Lichuan et al., Development and Applications of Active Noise Control System for Infant Incubators, Proceedings of the 2009 IEEE International Conference on Systems, Man, and Cybernetics San Antonio, TX, USA—Oct. 2009, pp. 1-6.

Mahil et al., Hybrid Swarm Algorithm for the Suppression of Incubator Interference in Premature Infants ECG, Research Journal of Applied Sciences, Engineering and Technology 6(16): 2931-2935, 2013.

Thermaxx Jackets, 5 most common thermal insulation materials, pp. 1-4, internet: https://www.thermaxxjackets.com/5-most-common-thermal-insulation-materials.

Kim et al., Air transparent soundproof window, AIP Advances 4, 117123 (2014), published online, doi: https://aip.scitation.org/doi/full/10.1063/1.4902155.

Marik et al., Neonatal incubators: A toxic sound environment for the preterm infant?, Pediatr Crit Care Med 2012 vol. 13, No. 6, pp. 1-6.

Ranganna et al., Reducing noise on the neonatal unit, Infant 2011, vol. 7, Issue 1, pp. 25-28.

* cited by examiner

Prior Art

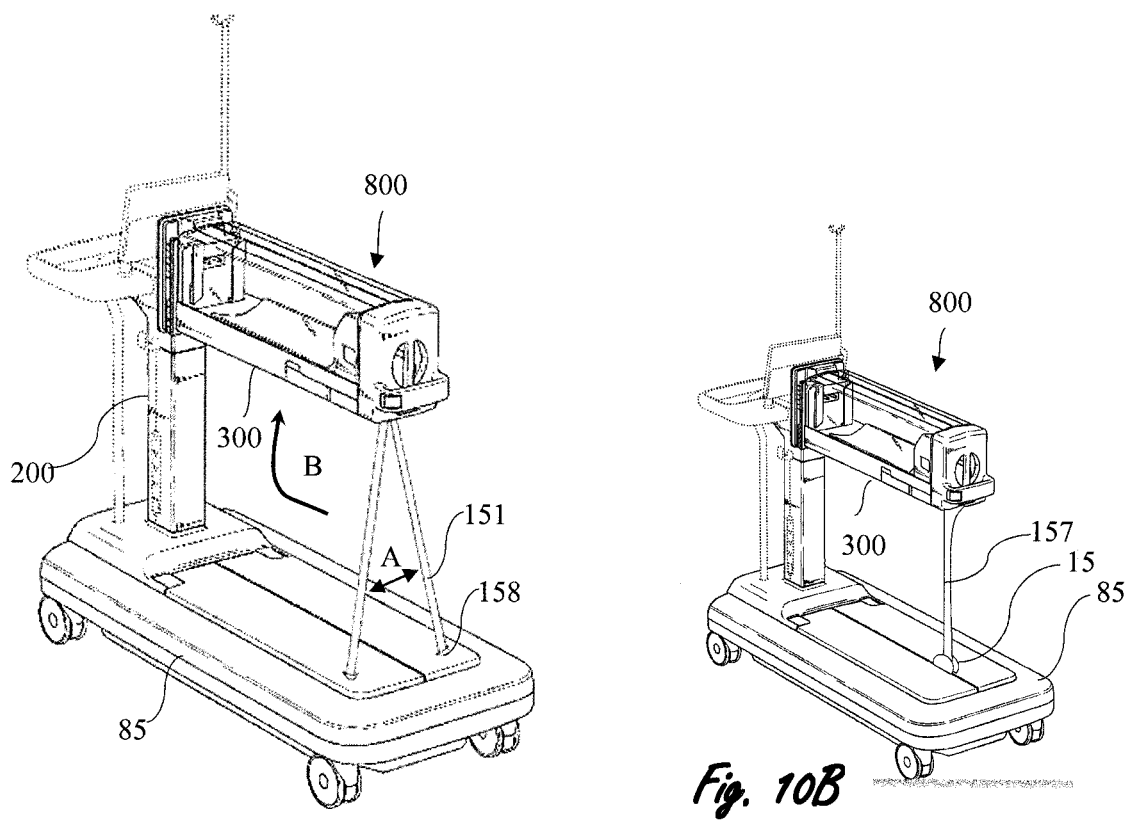
Fig. 10A
Fig. 10B
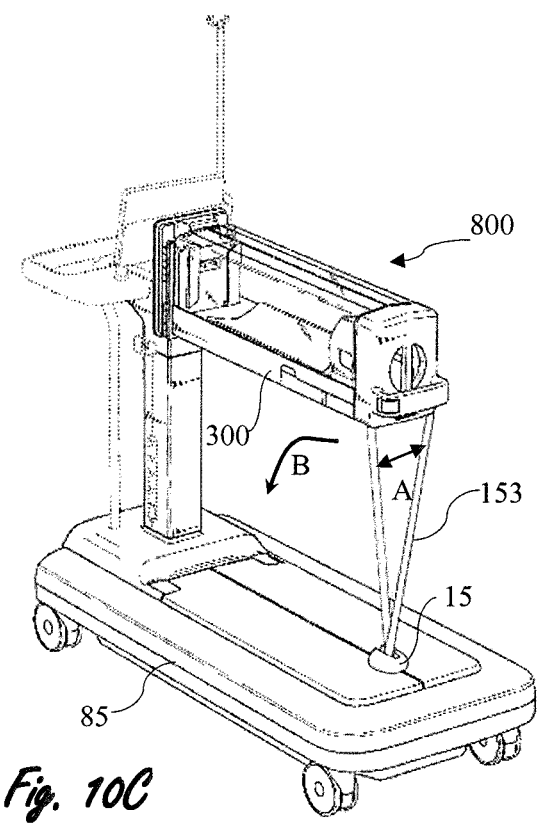
Fig. 10C

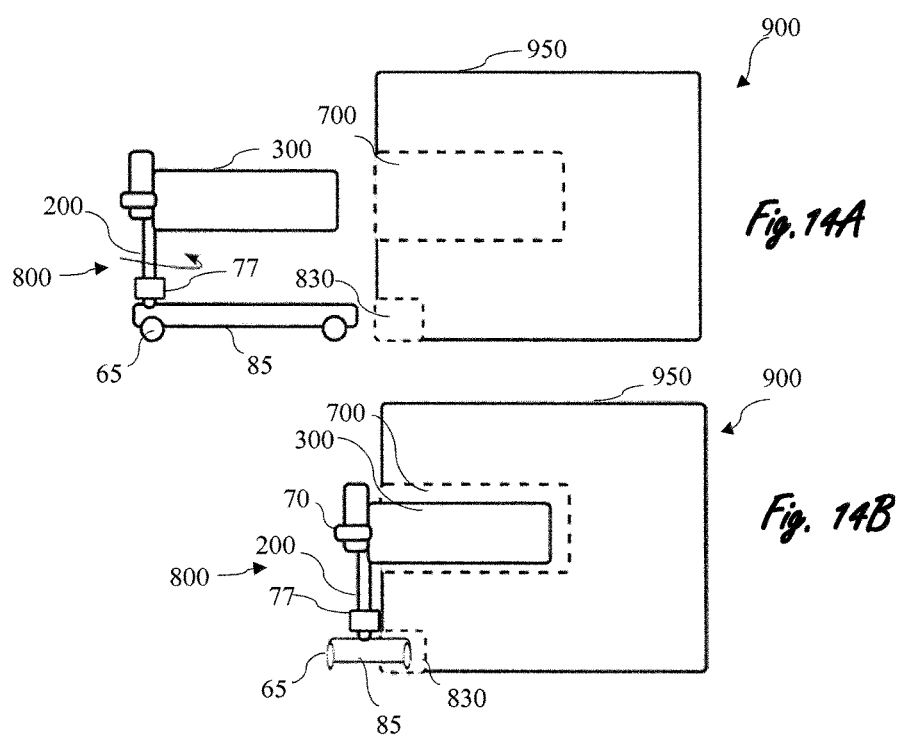

PREMATURE NEONATE LIFE SUPPORT ENVIRONMENTAL CHAMBER FOR USE IN MRI/NMR DEVICES

CROSS REFERENCE TO RELATED APPLICATIONS

This application is a continuation-in-part of U.S. patent application Ser. No. 13/808,476, filed on Jul. 11, 2013, which is a national stage filing of PCT/IL11/00537, filed on Jul. 7, 2011, which claims benefit of and priority to U.S. provisional application No. 61/361,936, filed on Jul. 7, 2010, all of which are incorporated herein by reference in their entirety. This application is also a continuation-in-part of U.S. patent application Ser. No. 14/892,207, filed on Nov. 19, 2015, which is a national stage filing of PCT/IL2014/050450, filed on May 21, 2014, which claims the benefit of and priority to U.S. provisional patent application No. 61/994,901, filed on May 18, 2014, all of which are incorporated herein by reference in their entirety.

FIELD OF THE INVENTION

The present invention relates to equipment for MRI imaging of premature neonates. In particular, it pertains to means and methods for enabling MRI examinations and measurements to be taken of premature neonates without detaching the neonates from life-support systems. The present invention also generally relates to the field of magnetic resonance imaging systems (MRI), and more particularly, to a magnetic resonance imaging system including a cart inserted into a magnetic resonance device. Further the present invention relates to an MRI safe cart, and an MRD fitting to intercept at least a portion of the cart during its operation.

BACKGROUND OF THE INVENTION

A well-known technical problem in the design of an MRI/NMR device is that of the fringing magnetic fields. These fringing magnetic fields can cause interference with nearby devices and lead to safety concerns arising from the possibility of placing magnetic material in propinquity to the MRI/NMR device as well as limiting the proximity of two MRI/NMR devices or other devices. This limitation results in the fact that almost invariably the MRI/NMR device is stored in a special isolated facility. This last problem is of particular concern for cases in which it is required to take MRI imaging examinations and measurements of a premature neonate without transferring the premature neonate between a premature neonate intensive-care ward and an MRI imaging facility, without decoupling and disconnecting the premature neonate from life-support systems.

The following prior art are believed to be relevant to the current status of the art:

U.S. Published Patent Application No. 2007/0232894 to Feenan describes an extendable carriage configured to shuttle between the neonate incubator and the magnetic resonance incubator system.

U.S. Pat. No. 6,611,702 to Rohling et al. describes an enclosure within the MRI device and adapted to maintain a selected environment with couplings to life-support mechanisms. An RF coil is located within the enclosure.

The website currently available at http://www.sciencedaily.com/videos/2005/1211-inside_the_preemie_brain.htm shows an incubator in use with an MRI device in which the premature neonate is transferred to a transportable incubator for examination.

The above-cited references, describe incubator devices in which the patient is removed from an incubator located in a hospital ward and placed within an MRI-incubator prior to the MRI examinations.

U.S. Pat. Nos. 5,800,335 and 7,278,962 to Koch and Lonneker-Lammers, respectively, describe a specialized incubator for use in tomography. These references do not relate to the problem of transferring a neonate from a ward-incubator to an MRI-compatible incubator.

The above-cited references do not provide a system or method enabling a premature neonate to undergo an MRI/NMR examination e.g., in the premature neonate intensive-care ward and require that the premature neonate be detached from the life-supporting systems during transfer to the MRI-compatible incubator. Thus, during placing the patient, such as a neonate, neonate in the prior art incubator, the patient or neonate is detached from the life-support systems, which can endanger the health of the patient.

Therefore, there is a long felt and hitherto unmet need for providing improved incubator devices.

Magnetic Resonance Imaging (MRI) uses high frequency waves and a magnetic field to create three-dimensional sections or layered images of body organs or tissue for medical diagnosis and research. These images greatly improve the ability of doctors to distinguish abnormal from healthy tissues. MRI can also be used to observe and measure dynamic physiological changes inside a patient without cutting into or penetrating the body. Conventional MRI devices consist of a closed tube into which the patient is inserted for the purpose of the examination. To produce an image, an MRI machine uses a powerful magnet to generate a magnetic field. When a patient lies within this field, the nuclei of atoms within the body align themselves with the magnetic field (much as iron filings line up around a magnet). Radio waves are then pulsed through the body, causing the nuclei to change their alignment with respect to the axis of the magnetic lines of force. As they return to their previous state after each pulse, they produce faint, distinctive radio signals; the rate at which they emit signals and the frequency of the signals depend on the type of atom, the temperature, the chemical environment, position, and other factors. These signals are detected by coils around the body and processed by a computer to produce images of internal structures.

When imaging patients, several parameters and precautions must be addressed. Since MRI imaging utilizes a strong magnet, care must be taken to insure that all elements and equipment in the vicinity of the MRI are 'MRI safe', meaning that they are not magnetic, not conductive, and not RF reactive. Many accidents were reported when metallic items were pulled in by the force of the magnetic field and harmed a patient during imaging.

Other risks may be peripheral nerve stimulation, exposure to a loud noise (up to 120 dB), generated by the rapid switching of the magnetic field gradients, or overheating may occur due to absorption of the energy that is utilized to generate the magnetic spin. Another risk involves an unintentional shut-down of a superconducting electromagnet ("quench"), resulting in the rapid boiling of liquid helium from the device. The rapidly expanding helium if released into the scanner room may cause displacement of the oxygen and present a risk of asphyxiation. In order to minimize risks and maintain homogenous conditions, a constant low temperature is kept in the MRI room.

Special care should be taken when MR scanning babies and neonates. New born and ill babies are usually kept in an incubator especially designed for maintaining constant environmental conditions such as temperature and humidity fitting for life supporting the baby. In addition in the incubator, functioning as an intensive care unit, provides the baby with connections to various medical devices and monitors to facilitate and overview breathing, feeding, fluid exchange and cardiac activity. Babies and neonates are also sensitive to excess light, noise, vibration and handling, and so these must be minimized to benefit recovery. Any transfer or movement of the baby may require the transfer or reconnection of attached medical devices, posing an additional stress on the baby. Further, any changes in location of the neonate may expose him to infection from an unprotected environment.

It is needed to take MRI examinations and measurements of a premature neonate without transferring the premature neonate between a premature neonate intensive-care ward and an MRI imaging facility, without decoupling and disconnecting the premature neonate from life-support systems.

In order to maximize efficiency of MR imaging, and minimize potential risk to the patient an obstacle free environment should be maintained in the vicinity of the patient when scanned. Further placing the patient in a specific position in the scanner should be quick and precise. And lastly imaging conditions should be homogenous to allow comparison between different scans and to minimize artifacts or loss of information.

U.S. Pat. No. 8,147,396 B2, filed Nov. 24, 2004 titled: "NEONATE IMAGING SUB SYSTEM", discloses a radiographic imaging subsystem for treating neonates. The subsystem includes a radiographic compatible incubator, a radiographic compatible RF coil, and a radiographic compatible trolley. The above cited reference describes incubator devices in which the patient is removed from an incubator located in a hospital ward and placed within an MRI-incubator prior to the MRI examinations.

The above-cited references does not provide a system enabling a premature neonate to undergo an MRI/NMR examination e.g., in the premature neonate intensive-care ward and require that the premature neonate be detached from the life-supporting systems during transfer to the MRI-compatible incubator. Thus, during placing the patient, such as a neonate, neonate in the prior art incubator, the patient or neonate is detached from the life-support systems, which can endanger the health of the patient. Further the above sited reference does not provide a system of an incubator as a portion of a cart accepted in an MRD bore thereby providing a single step process for imaging a neonate.

Therefore, there is a long felt need for an apparatus facilitating MRI scanning of a baby that maintains environmental conditions and life support equipment connections and monitoring during the scan. Further, this apparatus will limit excess handling, and eliminate the need for decoupling or disconnecting the neonate from life supporting of the baby during MRI imaging and preparation thereof, thereby providing a single step process for imaging a neonate. This system will therefor increase the safety of neonates during MRI scanning and preparations thereof. Further there is a long felt need for a system providing integrated solutions that address the special needs when imaging a patient, while limiting excess handling, eases placement of the patient and prevents exposure of the patient to the external environment conditions.

SUMMARY OF THE INVENTION

One object of the invention is to disclose a premature neonate life support environmental cradle (SEC), adapted by means of shape and size to be accommodated within (i) an incubator for premature neonates; and (ii) a measurement device; the SEC is configured for a first at least one open position for accommodating the neonate whilst the SEC is within the incubator, and a second closed position for confinement of the neonate within a sealed volume of incubator atmosphere within the SEC such that the integrity of the confinement is maintained upon removal of the closed SEC containing the neonate from the incubator.

Another object of the invention is to disclose an MRI-dedicated premature neonate life support environmental cradle (SEC) as defined above, wherein the MRI-dedicated SEC is constructed from materials permeable to magnetic fields; and wherein the measurement device is an MRI device.

Another object of the invention is to disclose a SEC as defined above, wherein the SEC further comprising an adaptor for connection to a closed life support system for the neonate.

Another object of the invention is to disclose a SEC as defined above, wherein the SEC further comprising one or more hand access ports and at least two flexible non-resilient lightweight sealing gas-tight flaps (SFs), disposed within the same plane of the port aperture in an overlapping manner, entirely enclosing the port aperture for handling the neonate.

Another object of the invention is to disclose a SEC as defined above, wherein the SEC wherein the SEC is characterized by an at least partially reversibly collapsible or deployable structure.

Another object of the invention is to disclose a SEC as defined above, wherein the at least partially reversibly collapsible structure is constructed from a plurality of curved or polygonal flaps or sections adapted by means of size and shape to construct a continuous envelope having an open bore accommodating the neonate.

Another object of the invention is to disclose premature neonate life support incubator (SEI) adapted by means of shape and size to be accommodated within a measurement device; the SEI is made of materials that do not interfere with the measurement; the SEI is configured for a closed position for confinement of the neonate within a sealed volume of the SEI such that the integrity of the confinement is maintained upon transportation between the SEI containing the neonate and the measurement device.

Another object of the invention is to disclose an MRI-dedicated premature neonate life support incubator (MRI-SEI) adapted by means of shape and size to be accommodated within an MRI device; the MRI-SEI is made of magnetically permeable materials; the MRI-SEI is configured for a closed position for confinement of the neonate within a sealed volume of the MRI-SEI such that the integrity of the confinement is maintained upon both (i) transportation of the MRI-SEI containing the neonate to the MRI device and back, and (ii) during the measurement.

Another object of the invention is to disclose a method of taking measurements of a premature neonate without exposing the same to an environment outside its incubator; the method comprising steps of obtaining a premature neonate life support environmental cradle (SEC), providing the SEC by means of shape and size to be accommodated within (i) an incubator for premature neonates; and (ii) a measurement device; placing the SEC within the incubator; opening the SEC within the incubator; accommodating the neonate within the SEC in its at least one open position; before carrying out the measurements, closing the SEC within the incubator thereby confining within the SEC (i) a volume of incubator atmosphere and (ii) the neonate; exiting the SEC in its closed position from the incubator; and transferring the SEC containing the neonate to the measurement device and carrying out the measurements; without exposing the neonate to an external environment; wherein the step of transferring the neonate within the confined SEC is executed without exposing the neonate to an external environment.

Another object of the invention is to disclose the method defined above, wherein the method is especially adapted for taking MRI measurements of a premature neonate without exposing the same to an environment outside its incubator; wherein the step of obtaining a the SEC includes a step of constructing the SEC from materials permeable to magnetic fields; and the step of containing the neonate to the measurement device includes selecting the measurement device to be an MRI device.

Another object of the invention is to disclose a method of taking measurements of a premature neonate without exposing the same to an environment outside his incubator; the method comprising steps of obtaining a premature neonate life support incubator (SEI) adapted by means of shape and size to be accommodated within a measurement device; and constructing the SEI with materials that do not interfere with the measurement; configuring the SEI for a closed position for confinement of the neonate within a sealed volume of the SEI; accommodating the neonate within the SEI; before carrying out the measurements, transferring the SEI containing the neonate to the measurement device and carrying out the measurements; without exposing the neonate to an external environment. Thus, the integrity of the confinement is maintained upon both transportation of the SEI containing the neonate to the measurement device and back and along the measurement Another object of the invention is to disclose the method as defined above, especially adapted for taking MRI measurements of a premature neonate without exposing the same to an environment outside his incubator; wherein the step of obtaining a the SEC including a step of constructing the SEC from materials permeable to magnetic fields; and the step of carrying out the measurements including selecting the measurement device to be an MRI device.

Another object of the invention is to disclose a method of life support of a premature neonate during MRD measurements; the method comprising the steps of providing a neonate incubator permeable to magnetic fields; providing a premature support environmental chamber configured to contain the neonate incubator and having at least one of the life support services conventionally supplied to same, such that the neonate incubator is continuously provided with same; placing premature neonate into the incubator; and operating at least one life support service to the premature neonate; transferring the incubator containing the premature neonate into the SEC; wherein the step of transferring is made without decoupling the at least one life support service and further wherein the SEC operates from within a portable MRD device.

Another object of the invention is to disclose a premature neonate life-support environmental chamber (SEC) for MRI measurements comprising an MRI-compatible life-saving cubicle for supplying at least one life-support service to a premature neonate having an adaptable geometrical shape for insertion into an MRI device and comprising at least one magnetically permeable material, and a life-support coupling system for coupling the MRI-compatible life-saving cubicle to the at least one life-support system having an adaptable geometrical shape for insertion into the MRI device and comprising: a coupling/decoupling mechanism, and at least one magnetically permeable material, wherein the MRI-compatible life-saving cubicle remains coupled to the life-support system during placing the premature neonate in the MRI-compatible life-saving cubicle.

Another object of the invention is to disclose the device as defined above, wherein the at least one life-support service is selected from the group consisting of air, water, gas and fluid exchange, drug delivery, perfusions, waste removal, transfusions, anesthetic gas and any combination thereof.

Another object of the invention is to disclose a method for performing MRI measurements in a premature neonate life-support environmental chamber (SEC) comprising: providing an MRI device for performing the MRI measurements on a premature neonate; placing the premature neonate in an MRI-compatible life-saving cubicle; coupling the MRI-compatible cubicle to at least one life-support system; inserting the coupled-MRI-compatible life-saving cubicle into the MRI device, performing MRI measurements on the premature neonate, wherein concomitantly with the inserting the coupled-MRI-compatible cubicle into the MRI device, the life-support system remains coupled to the MRI-compatible cubicle providing the premature neonate with continuous at least one life-support service.

Another object of the invention is to disclose the method as defined above, wherein the MRI-compatible life-saving cubicle comprises magnetically permeable materials.

A method of supplying at least life-support service to a premature neonate during MRI imaging measurements comprising: providing a premature neonate environmental chamber (SEC) comprising an MRD device for MRI imaging of the premature neonate, and a premature neonate incubator having magnetically permeable walls; placing the premature neonate in the incubator; coupling the incubator to at least one of the life-support system for providing the at least life-support service to the premature neonate during the MRD imaging the premature neonate; operating at least one life-support service to the premature neonate; inserting the incubator accommodating the premature neonate into the SEC; wherein the inserting is performed while the incubator remains coupled to the at least one life-support system.

Magnetically permeable materials include, inter alia, materials, such as a polymethacrylate substance, such as polymethyl methacrylate (PMMA), Plexiglas and Perspex.

The life-support systems typically provide the following environmental properties to the neonate while placed in the incubator of the present invention, such as oxygen, air temperature and humidity, gas and fluid exchange, drug delivery, perfusions, waste removal, transfusions, anesthetic gas and any other necessary fluids and substances.

The present invention provides a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD, and further wherein at least a portion of the base is reversibly housed within at least one recess.

It is another object of the current invention to disclose the MRS defined in any of the above, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

It is another object of the current invention to disclose the MRS defined in any of the above, wherein the cart incubator is connected to the cart by a maneuverable connection enabling movement selected from a group consisting of: rotational, linear horizontal, linear vertical, tilting, oscillating movement, and any combination thereof.

It is another object of the current invention to disclose the MRS defined in any of the above, wherein the incubator is reversibly connected to the cart.

It is another object of the current invention to disclose the MRS defined in any of the above, wherein the cart is configured to sealingly enclose the MRD open bore when at least a portion thereof is housed within the MRD.

It is another object of the current invention to disclose the MRS defined in any of the above, wherein at least a portion of the MRS comprises a material selected from a group consisting of: MRI-safe material, sterilizable material, at least a partially transparent material, and any combination thereof.

It is another object of the current invention to disclose the MRS defined in any of the above, wherein the cart comprises at least one support, connecting the incubator to a selected from a group consisting of: the pillar, a wall, a transport device, the MRD, a storage unit, a floor and any combination thereof.

It is another object of the current invention to disclose the MRS defined in any of the above, wherein the cart pillar is reversibly connected to an element selected from a group consisting of: the cart upper tray, the cart base, at least one support, a least one storage unit, and any combination thereof.

It is another object of the current invention to disclose the MRS defined in any of the above, wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose the MRS defined in any of the above, wherein at least one of the following is held true: (a) the column is configured to be normally deployed; (b) the column is collapsible upon application of horizontal force in an axis parallel to the open bore; (c) the column is at least partially reversibly collapsible into or onto an element selected from a group consisting of: the base, the upper tray, the pillar, or any combination thereof, when the cart is at least partially intercepted within the MRD; and, (d) the column is made of MRI-safe material.

It is another object of the current invention to disclose the MRS defined in any of the above, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

It is another object of the current invention to disclose the MRS defined in any of the above, wherein the at least one column end is reversibly connectable to at least two locations selected from a group consisting of: the cart base, the cart upper tray, the cart pillar, a storage unit, a wall, a transport device, and any combination thereof.

It is another object of the current invention to disclose the MRS defined in any of the above, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

It is another object of the current invention to disclose the MRS defined in any of the above, wherein the column is at least partially reversibly collapsible into or onto an element selected from a group consisting of: the base, the upper tray, the pillar, when force is applied on the column.

It is another object of the current invention to disclose the MRS defined in any of the above, wherein the column comprises a telescopic or folding mechanism, thereby enabling different length of the column.

It is another object of the current invention to disclose the MRS defined in any of the above, wherein a selected from a group consisting of: the column, the MRD, the cart and any combination thereof, comprises at least one latching mechanism configured to hold at least one first position of the column.

It is another object of the current invention to disclose the MRS defined in any of the above, wherein the cart base is of a fork like shape, having a recess sized and fitted to house the at least a portion of the MRD.

It is another object of the current invention to disclose the MRS defined in any of the above, wherein the cart's base comprises at least one protrusion sized and shaped to be inserted at least partially into the MRD's at least one recess or under the MRD.

It is another object of the current invention to disclose the MRS defined in any of the above, wherein the at least one recess is selected from a group consisting of: parallel to the open bore, perpendicular to the open bore, in an angle to the open bore, and any combination thereof.

It is another object of the current invention to disclose the MRS defined in any of the above, wherein the recess is sized and shaped as a mold of at least a portion of the cart.

It is another object of the current invention to disclose the MRS defined in any of the above, wherein the recess comprises a rail or track along which the base is at least partially housed.

It is another object of the current invention to disclose the MRS defined in any of the above, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

It is another object of the current invention to disclose the MRS defined in any of the above, wherein the MRD comprises a selected from a group consisting of: a sliding mechanism, a rail, a guide, and any combination thereof configured to slide the cart at least partially into the MRD.

It is another object of the current invention to disclose the MRS defined in any of the above, wherein the MRD, the cart, or both comprise an emergency release mechanism, to extract the neonate accommodated within.

It is another object of the current invention to disclose the MRS defined in any of the above, wherein the cart, the MRD or both, comprises a plurality of medical equipment, medical equipment placing, or both.

It is another object of the current invention to disclose the MRS defined in any of the above, wherein the cart, the MRD or both, comprises at least one handle.

It is another object of the current invention to disclose the MRS defined in any of the above, wherein the pillar is telescopic configured to provide an adjustable height of the patient's bed.

It is another object of the current invention to disclose the MRS defined in any of the above, wherein the pillar is connected to the base, the incubator or both, by a mechanism configured to provide rotating movement of the incubator relative to the base.

It is another object of the current invention to disclose the MRS defined in any of the above, wherein the pillar is at least partially hollow and comprises a conduit sized and shaped for the passage of medical equipment tubing.

It is another object of the current invention to disclose the MRS defined in any of the above, wherein the pillar is further connected to at least one storage tray, at least one storage unit or both.

It is another object of the current invention to disclose the MRS defined in any of the above, wherein the cart, the MRD or both comprise a user interface.

It is another object of the current invention to disclose the MRS defined in any of the above, wherein the cart user interface is configured to control the MRD operating system.

It is another object of the current invention to disclose the MRS defined in any of the above, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

The present invention provides a magnetic resonance device (MRD), useful for imaging a patient, at least partially contained in an envelope comprising an open bore, and at least one recess in the circumference of the envelope, wherein the MRD is configured to fit at least partially an MRI safe cart, made of MM-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within the at least one recess.

It is another object of the current invention to disclose the MRD defined in any of the above, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

It is another object of the current invention to disclose the MRD defined in any of the above, wherein the cart incubator is connected to the cart by a maneuverable connection enabling movement selected from a group consisting of: rotational, linear horizontal, linear vertical, tilting, oscillating movement, and any combination thereof.

It is another object of the current invention to disclose the MRD defined in any of the above, wherein the incubator is reversibly connected to the cart.

It is another object of the current invention to disclose the MRD defined in any of the above, wherein the cart is configured to sealingly enclose the MRD open bore when at least a portion thereof is housed within the MRD.

It is another object of the current invention to disclose the MRD defined in any of the above, wherein at least a portion of the MRS comprises a material selected from a group consisting of: MRI-safe material, sterilizable material, at least a partially transparent material, and any combination thereof.

It is another object of the current invention to disclose the MRD defined in any of the above, wherein the cart comprises at least one support, connecting the incubator to a selected from a group consisting of: the pillar, a wall, a transport device, the MRD, a storage unit, a floor and any combination thereof.

It is another object of the current invention to disclose the MRD defined in any of the above, wherein the cart pillar is reversibly connected to an element selected from a group consisting of: the cart upper tray, the cart base, at least one support, a least one storage unit, and any combination thereof.

It is another object of the current invention to disclose the MRD defined in any of the above, wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose the MRD defined in any of the above, wherein at least one of the following is held true: (a) the column is configured to be normally deployed; (b) the column is collapsible upon application of horizontal force in an axis parallel to the open bore; (c) the column is at least partially reversibly collapsible into or onto an element selected from a group consisting of: the base, the upper tray, the pillar, or any combination thereof, when the cart is at least partially intercepted within the MRD; and, (d) the column is made of MRI-safe material.

It is another object of the current invention to disclose the MRD defined in any of the above, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

It is another object of the current invention to disclose the MRD defined in any of the above, wherein the at least one column end is reversibly connectable to at least two locations selected from a group consisting of: the cart base, the cart upper tray, the cart pillar, a storage unit, a wall, a transport device, and any combination thereof.

It is another object of the current invention to disclose the MRD defined in any of the above, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

It is another object of the current invention to disclose the MRD defined in any of the above, wherein the column is at least partially reversibly collapsible into or onto an element selected from a group consisting of: the base, the upper tray, the pillar, when the cart is at least partially intercepted within the MRD.

It is another object of the current invention to disclose the MRD defined in any of the above, wherein the column comprises a telescopic or folding mechanism, thereby enabling different length of the column.

It is another object of the current invention to disclose the MRD defined in any of the above, wherein a selected from a group consisting of: the column, the MRD, the cart and any combination thereof, comprises at least one latching mechanism configured to hold at least one first position of the column.

It is another object of the current invention to disclose the MRD defined in any of the above, wherein the cart base is of a fork like shape, having a recess sized and fitted to house the at least a portion of the MRD.

It is another object of the current invention to disclose the MRD defined in any of the above, wherein the cart's base comprises at least one protrusion sized and shaped to be inserted at least partially into the MRD's at least one recess or under the MRD.

It is another object of the current invention to disclose the MRD defined in any of the above, wherein the at least one recess is selected from a group consisting of: parallel to the open bore, perpendicular to the open bore, in an angle to the open bore, and any combination thereof.

It is another object of the current invention to disclose the MRD defined in any of the above, wherein the recess is sized and shaped as a mold of at least a portion of the cart.

It is another object of the current invention to disclose the MRD defined in any of the above, wherein the recess comprises a rail or track along which the base is at least partially housed.

It is another object of the current invention to disclose the MRD defined in any of the above, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

It is another object of the current invention to disclose the MRD defined in any of the above, wherein the MRD comprises a selected from a group consisting of: a sliding mechanism, a rail, a guide, and any combination thereof configured to slide the cart at least partially into the MRD.

It is another object of the current invention to disclose the MRD defined in any of the above, wherein the MRD, the cart, or both comprise an emergency release mechanism, to extract the neonate accommodated within.

It is another object of the current invention to disclose the MRD defined in any of the above, wherein the cart, the MRD or both, comprises a plurality of medical equipment, medical equipment placing, or both.

It is another object of the current invention to disclose the MRD defined in any of the above, wherein the cart, the MRD or both, comprises at least one handle.

It is another object of the current invention to disclose the MRD defined in any of the above, wherein the pillar is telescopic configured to provide an adjustable height of the patient's bed.

It is another object of the current invention to disclose the MRD defined in any of the above, wherein the pillar is connected to the base, the incubator or both, by a mechanism configured to provide rotating movement of the incubator relative to the base.

It is another object of the current invention to disclose the MRD defined in any of the above, wherein the pillar is at least partially hollow and comprises a conduit sized and shaped for the passage of medical equipment tubing.

It is another object of the current invention to disclose the MRD defined in any of the above, wherein the pillar is further connected to at least one storage tray, at least one storage unit or both.

It is another object of the current invention to disclose the MRD defined in any of the above, wherein the cart, the MRD or both comprise a user interface.

It is another object of the current invention to disclose the MRD defined in any of the above, wherein the cart user interface is configured to control the MRD operating system.

It is another object of the current invention to disclose the MRD defined in any of the above, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

The present invention provides an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD, and further wherein at least a portion of the cart's base is reversibly housed within at least one recess.

It is another object of the current invention to disclose the MRI-safe cart defined in any of the above, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

It is another object of the current invention to disclose the MRI-safe cart defined in any of the above, wherein the cart incubator is connected to the cart by a maneuverable connection enabling movement selected from a group consisting of: rotational, linear horizontal, linear vertical, tilting, oscillating movement, and any combination thereof.

It is another object of the current invention to disclose the MRI-safe cart defined in any of the above, wherein the incubator is reversibly connected to the cart.

It is another object of the current invention to disclose the MRI-safe cart defined in any of the above, wherein the cart is configured to sealingly enclose the MRD open bore when at least a portion thereof is housed within the MRD.

It is another object of the current invention to disclose the MRI-safe cart defined in any of the above, wherein at least a portion of the MRS comprises a material selected from a group consisting of: MRI-safe material, sterilizable material, at least a partially transparent material, and any combination thereof.

It is another object of the current invention to disclose the MRI-safe cart defined in any of the above, wherein the cart comprises at least one support, connecting the incubator to a selected from a group consisting of: the pillar, a wall, a transport device, the MRD, a storage unit, a floor and any combination thereof.

It is another object of the current invention to disclose the MRI-safe cart defined in any of the above, wherein the cart pillar is reversibly connected to an element selected from a group consisting of: the cart upper tray, the cart base, at least one support, a least one storage unit, and any combination thereof.

It is another object of the current invention to disclose the MRI-safe cart defined in any of the above, wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose the MRI-safe cart defined in any of the above, wherein at least one of the following is held true: (a) the column is configured to be normally deployed; (b) the column is collapsible upon application of horizontal force in an axis parallel to the open bore; (c) the column is at least partially reversibly collapsible into or onto an element selected from a group consisting of: the base, the upper tray, the pillar, or any combination thereof, when the cart is at least partially intercepted within the MRD; and, (d) the column is made of MRI-safe material.

It is another object of the current invention to disclose the MRI-safe cart defined in any of the above, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

It is another object of the current invention to disclose the MRI-safe cart defined in any of the above, wherein the at least one column end is reversibly connectable to at least two locations selected from a group consisting of: the cart base, the cart upper tray, the cart pillar, a storage unit, a wall, a transport device, and any combination thereof.

It is another object of the current invention to disclose the MRI-safe cart defined in any of the above, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

It is another object of the current invention to disclose the MRI-safe cart defined in any of the above, wherein the column is at least partially reversibly collapsible into or onto an element selected from a group consisting of: the base, the upper tray, the pillar, when force is applied on the column.

It is another object of the current invention to disclose the MRI-safe cart defined in any of the above, wherein the column comprises a telescopic or folding mechanism, thereby enabling different length of the column.

It is another object of the current invention to disclose the MRI-safe cart defined in any of the above, wherein a selected from a group consisting of: the column, the MRD, the cart and any combination thereof, comprises at least one latching mechanism configured to hold at least one first position of the column.

It is another object of the current invention to disclose the MRI-safe cart defined in any of the above, wherein the cart base is of a fork like shape, having a recess sized and fitted to house the at least a portion of the MRD.

It is another object of the current invention to disclose the MRI-safe cart defined in any of the above, wherein the cart's base comprises at least one protrusion sized and shaped to be inserted at least partially into the MRD's at least one recess or under the MRD.

It is another object of the current invention to disclose the MRI-safe cart defined in any of the above, wherein the at least one recess is selected from a group consisting of: parallel to the open bore, perpendicular to the open bore, in an angle to the open bore, and any combination thereof.

It is another object of the current invention to disclose the MRI-safe cart defined in any of the above, wherein the recess is sized and shaped as a mold of at least a portion of the cart.

It is another object of the current invention to disclose the MRI-safe cart defined in any of the above, wherein the recess comprises a rail or track along which the base is at least partially housed.

It is another object of the current invention to disclose the MRI-safe cart defined in any of the above, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

It is another object of the current invention to disclose the MRI-safe cart defined in any of the above, wherein the MRD comprises a selected from a group consisting of: a sliding mechanism, a rail, a guide, and any combination thereof configured to slide the cart at least partially into the MRD.

It is another object of the current invention to disclose the MRI-safe cart defined in any of the above, wherein the MRD, the cart, or both comprise an emergency release mechanism, to extract the neonate accommodated within.

It is another object of the current invention to disclose the MRI-safe cart defined in any of the above, wherein the cart, the MRD or both, comprises a plurality of medical equipment, medical equipment placing, or both.

It is another object of the current invention to disclose the MRI-safe cart defined in any of the above, wherein the cart, the MRD or both, comprises at least one handle.

It is another object of the current invention to disclose the MRI-safe cart defined in any of the above, wherein the pillar is telescopic configured to provide an adjustable height of the patient's bed.

It is another object of the current invention to disclose the MRI-safe cart defined in any of the above, wherein the pillar is connected to the base, the incubator or both, by a mechanism configured to provide rotating movement of the incubator relative to the base.

It is another object of the current invention to disclose the MRI-safe cart defined in any of the above, wherein the pillar is at least partially hollow and comprises a conduit sized and shaped for the passage of medical equipment tubing.

It is another object of the current invention to disclose the MRI-safe cart defined in any of the above, wherein the pillar is further connected to at least one storage tray, at least one storage unit or both.

It is another object of the current invention to disclose the MRI-safe cart defined in any of the above, wherein the cart, the MRD or both comprise a user interface.

It is another object of the current invention to disclose the MRI-safe cart defined in any of the above, wherein the cart user interface is configured to control the MRD operating system.

It is another object of the current invention to disclose the MRI-safe cart defined in any of the above, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

The present invention provides a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose the reversibly collapsible column defined in any of the above, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

It is another object of the current invention to disclose the reversibly collapsible column defined in any of the above, wherein the cart incubator is connected to the cart by a maneuverable connection enabling movement selected from a group consisting of: rotational, linear horizontal, linear vertical, tilting, oscillating movement, and any combination thereof.

It is another object of the current invention to disclose the reversibly collapsible column defined in any of the above, wherein the incubator is reversibly connected to the cart.

It is another object of the current invention to disclose the reversibly collapsible column defined in any of the above, wherein the cart is configured to sealingly enclose the MRD open bore when at least a portion thereof is housed within the MRD.

It is another object of the current invention to disclose the reversibly collapsible column defined in any of the above, wherein at least a portion of the MRS comprises a material selected from a group consisting of: MRI-safe material, sterilizable material, at least a partially transparent material, and any combination thereof.

It is another object of the current invention to disclose the reversibly collapsible column defined in any of the above, wherein the cart comprises at least one support, connecting the incubator to a selected from a group consisting of: the pillar, a wall, a transport device, the MRD, a storage unit, a floor and any combination thereof.

It is another object of the current invention to disclose the reversibly collapsible column defined in any of the above, wherein the cart pillar is reversibly connected to an element selected from a group consisting of: the cart upper tray, the cart base, at least one support, a least one storage unit, and any combination thereof.

It is another object of the current invention to disclose the reversibly collapsible column defined in any of the above, wherein at least one of the following is held true: (a) the column is configured to be normally deployed; (b) the column is collapsible upon application of horizontal force in an axis parallel to the open bore; (c) the column is at least partially reversibly collapsible into or onto an element selected from a group consisting of: the base, the upper tray, the pillar, or any combination thereof, when the cart is at least partially intercepted within the MRD; and, (d) the column is made of MRI-safe material.

It is another object of the current invention to disclose the reversibly collapsible column defined in any of the above, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

It is another object of the current invention to disclose the reversibly collapsible column defined in any of the above, wherein the at least one column end is reversibly connectable to at least two locations selected from a group consisting of: the cart base, the cart upper tray, the cart pillar, a storage unit, a wall, a transport device, and any combination thereof.

It is another object of the current invention to disclose the reversibly collapsible column defined in any of the above, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

It is another object of the current invention to disclose the reversibly collapsible column defined in any of the above, wherein the column is at least partially reversibly collapsible into or onto an element selected from a group consisting of: the base, the upper tray, the pillar, when force is applied on the column.

It is another object of the current invention to disclose the reversibly collapsible column defined in any of the above, wherein the column comprises a telescopic or folding mechanism, thereby enabling different length of the column.

It is another object of the current invention to disclose the reversibly collapsible column defined in any of the above, wherein a selected from a group consisting of: the column, the MRD, the cart and any combination thereof, comprises at least one latching mechanism configured to hold at least one first position of the column.

It is another object of the current invention to disclose the reversibly collapsible column defined in any of the above, wherein the cart base is of a fork like shape, having a recess sized and fitted to house the at least a portion of the MRD.

It is another object of the current invention to disclose the reversibly collapsible column defined in any of the above, wherein the cart's base comprises at least one protrusion sized and shaped to be inserted at least partially into the MRD's at least one recess or under the MRD.

It is another object of the current invention to disclose the reversibly collapsible column defined in any of the above, wherein the at least one recess is selected from a group consisting of: parallel to the open bore, perpendicular to the open bore, in an angle to the open bore, and any combination thereof.

It is another object of the current invention to disclose the reversibly collapsible column defined in any of the above, wherein the recess is sized and shaped as a mold of at least a portion of the cart.

It is another object of the current invention to disclose the reversibly collapsible column defined in any of the above, wherein the recess comprises a rail or track along which the base is at least partially housed.

It is another object of the current invention to disclose the reversibly collapsible column defined in any of the above, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

It is another object of the current invention to disclose the reversibly collapsible column defined in any of the above, wherein the MRD comprises a selected from a group consisting of: a sliding mechanism, a rail, a guide, and any combination thereof configured to slide the cart at least partially into the MRD.

It is another object of the current invention to disclose the reversibly collapsible column defined in any of the above, wherein the MRD, the cart, or both comprise an emergency release mechanism, to extract the neonate accommodated within.

It is another object of the current invention to disclose the reversibly collapsible column defined in any of the above, wherein the cart, the MRD or both, comprises a plurality of medical equipment, medical equipment placing, or both.

It is another object of the current invention to disclose the reversibly collapsible column defined in any of the above, wherein the cart, the MRD or both, comprises at least one handle.

It is another object of the current invention to disclose the reversibly collapsible column defined in any of the above, wherein the pillar is telescopic configured to provide an adjustable height of the patient's bed.

It is another object of the current invention to disclose the reversibly collapsible column defined in any of the above, wherein the pillar is connected to the base, the incubator or both, by a mechanism configured to provide rotating movement of the incubator relative to the base.

It is another object of the current invention to disclose the reversibly collapsible column defined in any of the above, wherein the pillar is at least partially hollow and comprises a conduit sized and shaped for the passage of medical equipment tubing.

It is another object of the current invention to disclose the reversibly collapsible column defined in any of the above, wherein the pillar is further connected to at least one storage tray, at least one storage unit or both.

It is another object of the current invention to disclose the reversibly collapsible column defined in any of the above, wherein the cart, the MRD or both comprise a user interface.

It is another object of the current invention to disclose the reversibly collapsible column defined in any of the above, wherein the cart user interface is configured to control the MRD operating system.

It is another object of the current invention to disclose the reversibly collapsible column defined in any of the above, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; and, further wherein the cart is configured to sealingly enclose the MRD open bore when at least a portion thereof is housed within the MRD.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; and further wherein the MRD comprises a selected from a group consisting of: a sliding mechanism, a rail, a guide, and any combination thereof configured to slide the cart at least partially into the MRD.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; and, further wherein the cart base is of a fork like shape, having a recess sized and fitted to house at least a portion of the MRD.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; and, further wherein the cart's base comprises at least one protrusion sized and shaped to be inserted at least partially into the MRD's at least one recess or under the MRD.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; further wherein further the cart is configured to sealingly enclose the MRD open bore when at least a portion thereof is housed within the MRD; further wherein the cart base is of a fork like shape, having a recess sized and fitted to house at least a portion of the MRD; and, further wherein the cart's base comprises at least one protrusion sized and shaped to be inserted at least partially into the MRD's at least one recess or under the MRD.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; and, further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is configured to be normally deployed; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the column is made of MRI-safe material.

It is another object of the current invention to disclose a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD; further wherein at least a portion of the base is reversibly housed within at least one recess; further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is configured to be normally deployed; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the cart's base comprises at least one protrusion sized and shaped to be inserted at least partially into the MRD's at least one recess or under the MRD.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; and, further wherein the cart is configured to sealingly enclose the MRD open bore when at least a portion thereof is housed within the MRD.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; and, further wherein the cart base is of a fork like shape, having a recess sized and fitted to house at least a portion of the MRD.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; and, further wherein the cart's base comprises at least one protrusion sized and shaped to be inserted at least partially into the MRD's at least one recess or under the MRD.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; further wherein further the cart is configured to sealingly enclose the MRD open bore when at least a portion thereof is housed within the MRD; further wherein the cart base is of a fork like shape, having a recess sized and fitted to house at least a portion of the MRD; and, further wherein the cart's base comprises at least one protrusion sized and shaped to be inserted at least partially into the MRD's at least one recess or under the MRD.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; further wherein at least a portion of the base is reversibly housed within at least one recess; and, further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is configured to be normally deployed; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the column is made of MRI-safe material.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; and further wherein the MRD comprises a selected from a group consisting of: a sliding mechanism, a rail, a guide, and any combination thereof configured to slide the cart at least partially into the MRD.

It is another object of the current invention to disclose a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess; further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is configured to be normally deployed; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the cart's base comprises at least one protrusion sized and shaped to be inserted at least partially into the MRD's at least one recess or under the MRD.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; and, further wherein the cart is configured to sealingly enclose the MRD open bore when at least a portion thereof is housed within the MRD.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; and further wherein the cart, comprise a user interface configured to control the MRD operating system.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; and, further wherein the cart base is of a fork like shape, having a recess sized and fitted to house at least a portion of the MRD.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD, and further wherein at least a portion of the cart's base is reversibly housed within at least one recess; and, further wherein the cart's base comprises at least one protrusion sized and shaped to be inserted at least partially into the MRD's at least one recess or under the MRD.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; further wherein further the cart is configured to sealingly enclose the MRD open bore when at least a portion thereof is housed within the MRD; further wherein the cart base is of a fork like shape, having a recess sized and fitted to house at least a portion of the MRD; and, further wherein the cart's base comprises at least one protrusion sized and shaped to be inserted at least partially into the MRD's at least one recess or under the MRD.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; further wherein at least a portion of the base is reversibly housed within at least one recess; and, further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof further wherein the column is configured to be normally deployed; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the column is made of MRI-safe material.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; and further wherein the MRD comprises a selected from a group consisting of: a sliding mechanism, a rail, a guide, and any combination thereof configured to slide the cart at least partially into the MRD.

It is another object of the current invention to disclose an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD; further wherein at least a portion of the cart's base is reversibly housed within at least one recess; further wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is configured to be normally deployed; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the cart's base comprises at least one protrusion sized and shaped to be inserted at least partially into the MRD's at least one recess or under the MRD.

It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; and, further wherein the cart is configured to sealingly enclose the MRD open bore when at least a portion thereof is housed within the MRD.

It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; and, further wherein the cart base is of a fork like shape, having a recess sized and fitted to house at least a portion of the MRD.

It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; and, further wherein the cart's base comprises at least one protrusion sized and shaped to be inserted at least partially into the MRD's at least one recess or under the MRD.

It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein further the cart is configured to sealingly enclose the MRD open bore when at least a portion thereof is housed within the MRD; further wherein the cart base is of a fork like shape, having a recess sized and fitted to house at least a portion of the MRD; and, further wherein the cart's base comprises at least one protrusion sized and shaped to be inserted at least partially into the MRD's at least one recess or under the MRD.

It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein at least a portion of the base is reversibly housed within at least one recess; and, It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; and, further wherein the column is made of MRI-safe material.

It is another object of the current invention to disclose a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof; further wherein the column is collapsible upon application of horizontal force in an axis parallel to the open bore; further wherein the column is at least partially reversibly collapsible into or onto an element selected from a group consisting of: the base, the upper tray, the pillar, or any combination thereof, when the cart is at least partially intercepted within the MRD; further wherein the column is made of MRI-safe material; further wherein the column is configured to be normally deployed; and, further wherein the pillar is telescopic configured to provide an adjustable height of the patient's bed.

BRIEF DESCRIPTION OF THE DRAWINGS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

In order to understand the invention and to see how it may be implemented in practice, a few preferred embodiments will now be described, by way of non-limiting example only, with reference to the accompanying drawings, in which:

FIGS. 1 and 3 present an out-of-scale illustration (perspective view) of a SEC according to some embodiments of the invention;

FIG. 10A is a schematic illustration of a cart, in a perspective view, in which a column is of a fork like shape, collapsible toward the cart upper tray;

FIG. 10B is a schematic illustration of a cart, in a perspective view, in which a column is of a non-geometric shape, collapsible toward the cart base;

FIG. 10C is a schematic illustration of a cart, in a perspective view, in which a column is of a fork like shape, collapsible toward the cart base;

FIG. 14A is a schematic illustration of an MRS, in a side view, showing a cart having a rotational pillar, and an MRD having an open bore and a recess;

FIG. 14B is a schematic illustration of an MRS is a schematic illustration of an MRS, in a side view, showing a cart having a rotational pillar, at least partially inserted into a at least a portion of an MRD open bore and a recess;

DETAILED DESCRIPTION OF A PREFERRED EMBODIMENT OF THE PRESENT INVENTION

Figure 1:
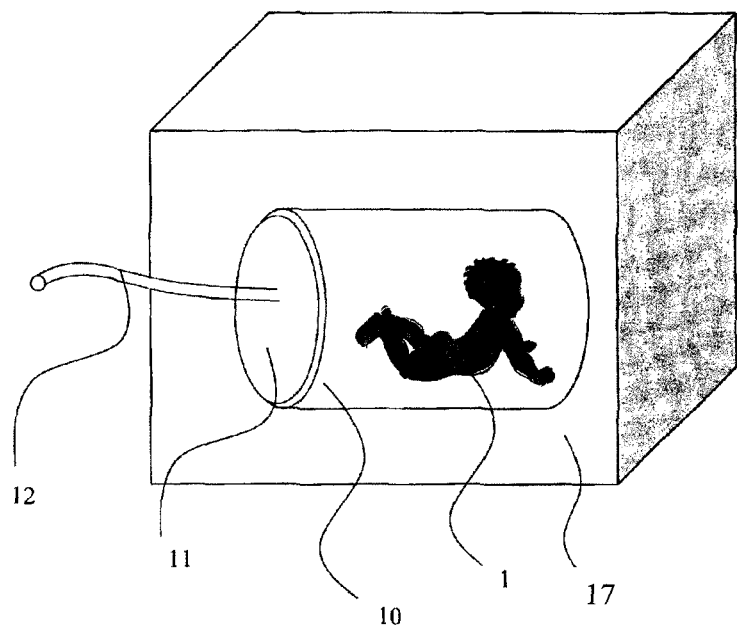

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a premature neonate life support environmental chamber and methods using the same.

The present invention provides a premature neonate life Support Environmental Chamber (hereinafter 'SEC'), permeable to magnetic fields for use in a portable MRI/NMR device, such as an MRD device. This environmental chamber SEC is adapted to accommodate any neonate incubator permeable to magnetic fields. Hence, the SEC is configured such that the SEC and the incubator include a closed life support system for the neonate.

The essence of the present invention is to provide a system including an MRI safe cart, and a magnetic resonance device having an open bore fitting to accept at least a portion of the cart, the cart's upper tray is a life supporting incubator fitted for accommodating a neonate in a care taking facility, sized and shaped to be at least partially accepted within the MRD bore, thereby providing a single step housing of the neonate, accommodated within the cart, at least partially within the MRD bore. Further, the system provides life supporting environment for a patient while imaging and preparations thereof.

In addition, the present invention provides a transportable MRI-safe cart comprising a life supporting incubator sized and shaped for at least partial housing within an open bore of a magnetic resonance device. Further, the present invention provides an MRD having an open bore sized and shaped to at least partially house an MRI-safe cart. The essence of the present invention is further to provide a foldable or collapsible column interconnecting the upper tray of the cart to another element such as the cart base, having a normally deployed configuration stabilizing the cart, and a collapsed position following the application of horizontal force.

The system of the present invention will eliminate the need to extract the patient from a life supporting environment for the purpose of imaging. This will increase the safety of patients during MRI and preparations thereof, and reduce excess handling of the patient.

The term 'anesthetic gas' refers hereinafter to any gas selected from a group consisting of Nitrous oxide ($N_2O$), Halothane, Enflurane, Isoflurane, Sevoflurane, Desflurane and Xenon, water, oxygen or any combination thereof.

The term 'magnetic resonance imaging device' (MRD), specifically applies hereinafter to any Magnetic Resonance Imaging (MM) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. Additionally or alternatively, the MRD is self-fastening cage surrounding a magnetic resonance device as depicted in U.S. Pat. No. 7,719,279 B2, filed 27 May 2008 titled: "SELF-FASTENING CAGE SURROUNDING A MAGNETIC RESONANCE DEVICE AND METHODS THEREOF", of which is hereby incorporated by reference in its entirety. The MRD disclosed in the present invention is any magnetic resonance scanner known to a person skilled in the art of imaging. Without wishing to be bound by theory, the major components of an MRI scanner are: the main magnet, which polarizes the sample, and the RF system, which excites the sample and detects the resulting NMR signal. In order to localize the MR signal and produce a three dimensional image, a gradient system is used. Additionally or alternatively, the whole system is controlled by one or more computers. In order to be able to perform magnetic resonance imaging with high resolution, providing a high quality image (i.e., resolution and contrast) the magnetic field used must be extremely stable and uniform. In order to achieve such uniformity, elements correcting the inhomogeneousness of the main magnetic field are added such as coils, magnetic parts, or all other means enabling correction of the imperfections of the principal field are added in order to obtain a homogeneous total field in the zone of interest.

Without wishing to be bound by theory, the magnet is the main component of the MRI scanner, and its field strength is measured in teslas (T). The magnet field strength for clinical and research use is in the range 0.1- and 21 T (up to 9.4 for human use). Another important aspect is the precision of the magnet, creating magnetic lines, with as little fluctuation as possible. The magnet is generally one of the following: a permanent magnet, made from ferromagnetic materials (such as magnetic alloys and rare earth elements); a resistive electromagnet, that requires considerable electrical energy during operation; or a superconducting electromagnet, for example a niobium-titanium alloy is cooled by liquid helium to become a super conductor.

Without wishing to be bound by theory, magnetic field strength is an important factor in determining image quality. Higher magnetic fields increase signal-to-noise ratio, permitting higher resolution or faster scanning. All samples placed in a magnetic field distort the magnetic field especially at tissue-air boundaries. To restore field homogeneity a set of shim coils is sometimes included in the scanner. These are resistive coils, usually at room temperature, capable of producing field corrections. As mentioned, a gradient coil will create an additional, linearly varying magnetic field that adds or subtracts from the main magnetic field. This additional magnetic field will have components in all 3 directions, viz. x, y and z;

Without wishing to be bound by theory, the radio frequency (RF) transmission system consists of an RF synthesizer, power amplifier and transmitting coil. That coil is usually built into the body of the scanner. These electromagnetic fields are in the RF range of tens of megahertz. The RF synthesizer produces a sine wave of the desired frequency. The Pulse programmer shapes the RF pulses. The RF amplifier increases the pulses power from milli Watts to killo Watts.

While it is possible to scan using the integrated coil for RF transmission and MR signal reception, if a small region is being imaged, then better image quality (i.e. higher signal-to-noise ratio) is obtained by using a close-fitting smaller coil. A variety of coils are available which fit closely around parts of the body. Additionally or alternatively the MRS system comprises an installable RF coil assembly in the cart, the MRD or both. The assembled RF coil in the cart is as depicted in IL Pat. Appl. 226488, filed 21 May 13, titled "A cradle for neonates", of which is hereby incorporated herein by reference in its entirety.

Without wishing to be bound by theory, the patient is positioned within an open bore (700) at least partially surrounded by a magnet on a patient designated table/placing. The patient table position and angle can be manually controlled or computer controlled. The MRD can be surrounded by an RF shield. This shield could also surround the magnet. The shield provides a barrier from MRD generated EMI to reach the external environment and prevents RF signals generated in the external environment from such as television, elevators, etc. from affecting the MRD.

Another important part of the scanner is the imager computer. It controls all components on the imager e.g. the radio frequency source and the pulse programmer. The computer also controls the gradient pulse programmer which sets the shape and amplitude of each of the three gradient fields. The gradient amplifier increases the power of the gradient pulses to a level sufficient to drive the gradient coils. A computer is also utilized to implement the data received into a viewable picture. Additionally or alternatively, the MRD harbors a user interface for allowing the handler to observe, monitor and/or control different parameters of the MRD operation such as scanning, alarm systems detecting RF signals, metallic objects, temperature, movement, sound levels, vibrations and etc. All the data can be collected by designated sensors connected to the MRD, cart or both. Further information can also be collected from sensors connected to the patient, such as cardio sensors, respiratory sensors, temperature, brain activity, vibration, blood pressure, blood oxygenation, and etc. Additionally or alternatively the user interface harbors a display, indicators (sensible, auditable, visual), and operating buttons or means of communication with the CPU such as touch screen, mouse, keyboard, voice command and etc.

A plurality of the components of an MRD are at least partially encased in an envelope, forming a three dimensional shape. This shape can be any polygon, sphere, cylinder, geometrical, none geometrical, compound shape, curved shape, etc. Following this envelope has an open bore (700) longitudinally on its Z-axis, and additionally or alternatively, have at least one recess (850).

Additionally or alternatively, this recess can be located on the front wall of the MRD parallel to the opening of the open bore, on either side (860) of the envelope, under the MRD, or any location in the circumference of the MRD envelope. The recess is sized and shaped to accept at least a portion of the cart. The MRD open bore and the recess are sized and shaped to house at least a portion of an MRI-safe cart. Additionally or alternatively, the open bore is sized and shaped to house at least a portion of the cart upper tray. Additionally or alternatively, the recess is sized and shaped to accept at least a portion of the cart base. Additionally or alternatively, the open bore, recess or both contain a sliding mechanism for assisting in the insertion of at least a portion of the cart, or specifically an incubator, or cart upper tray, a transport incubator, a deployable incubator. Further, the envelope defining the open bore can additionally or alternatively comprise a placement or conduit for the passage of medical equipment tubing. Further this passage is configured to be RF shielding. In one embodiment of the present application the MRD comprises a front wall, having a bore opening sized and shaped to accommodate an incubator or a patient.

The term "cart" interchangeably refers hereinafter to any transport device or any small vehicle pushed or pulled by manually, automatically or both. A cart usually comprises mobility providing elements such as one or a plurality of a wheel, roller, sliding blade, rotating belt, etc. Further, the cart can be such as rickshaw, nick, wagon, barrow, buggy, dolly, carriage, float, cab, dray, gig, gurney, handcart, palanquin, pushcart, tumbrel, wheelbarrow, curricle, etc.

The term "column" refers hereinafter to a support, rod, tripod, stand, mount, frame, easel, stool, pedestal, quadrated, tetrapod, quintuple legged, footing, hold, post, rib, reinforcement, etc. further this column is comprised of a single piece or multiple at least partially connected pieces.

The term "pillar" refers hereinafter to any structure interconnecting the cart's base to the cart upper tray, providing physical support to the cart's upper tray. This can be in a substantially perpendicular position relative to the cart's base, or in any other angled position. Further this structure can be hollow, frame like, solid, ladder like, symmetrical, none symmetrical, comprised of multiple pieces or one piece, etc. This structure can be connected to the cart's base in one or more locations, and connected to the cart upper tray in one or more locations. This structure could further be connected to a carts handle, life support equipment, a storage unit, a user interface, a computer, an MRI closure assembly, etc.

The term "external environment" refers hereinafter to the external space outside of an MRD.

As used herein, the term "neonate" refers to any object or living creature inserted in whole or in part within an incubator.

As used herein, the term "plurality" refers in a non-limiting manner to any integer equal or greater than 1.

The term 'about' can apply hereinafter to a measure being ±25% of the defined value or refers hereinafter to 20% more or less than the defied value.

The term "baby" or "patient" or "neonate" interchangeably refers herein after to a term selected from a group of: neonate, newborn, baby, infant, toddler, child, adolescent, adult, elderly, patient, individual, subject, inmate, sufferer, outpatient, case, client, etc.; further this term refers to person, animal, or sample, as a whole or a portion thereof.

The term "transparent material" interchangeably refers hereinafter to materials such as, polymethyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further in some embodiments at least a portion of this material is imbedded with non-transparent materials for means of strength and/or conductivity such as metallic wires.

The term "connected" in reference to the cart, incubator, or MRD parts and connecting elements or components thereof, interchangeably refers hereinafter to any contact, relation, association, integration, interconnection, joining, inserting, sewing, welding, interweaving, placing, nesting, layering, placing akin, linkage, unity, alliance, bracketed, combination, coupling, banding, bonding, affiliation, fitting, pairing, attachment, hooking, hinging, welding, adhering, fusion, fixing, tying, sewing, embedding, weaving, etc., of cart, incubator, or MRD, parts and connecting elements or components thereof, to each other and to a third party.

The term "emergency release mechanism", interchangeably refers hereinafter to a mechanism used in immediate need of extracting a patient from the MRD bore that allows in one step the dislocation of at least a portion of the cart or incubator providing access to the patient.

The term "MRI-safe", interchangeably refers hereinafter to any device, part, element, component or implant that is completely non-magnetic, non-electrically conductive, and non-RF reactive, eliminating all of the primary potential threats during an MRI procedure.

The term "incubator" interchangeably refers hereinafter to a special unit specializing in the care of ill or premature newborn infants. This includes a stationary incubator, a moveable incubator, a transport incubator, a disposable incubator, a healthcare facility incubator, portable incubator, an intensive care incubator, an incubator intended for home use, an incubator for imaging a neonate, a treatment incubator, a modular incubator, an isolating incubator and any combination thereof. The neonatal incubator is a box-like enclosure in which an infant can be kept in a controlled environment for observation and care. The incubator usually includes observation means to the accommodated neonate, and openings for the passage of life support equipment, and the handler's hands. At least partially enclosed environment formed within the incubator is at least partially isolated from the external environment conditions such as noise, vibration, drift, temperature, light, gas concentrations, humidity, microorganisms, etc., and/or regulated to reach life supporting parameters defined by medical personal. The incubator can contain, or be connected to life supporting equipment. The internal environment can be controlled by environment control systems such as temperature regulating, ventilating, humidifying, lighting, moving, noise reduction systems, vibration reducing systems, etc. An incubator is, in an embodiment, a deployable incubator as depicted in U.S. Provisional Pat. Appl. 61/940,514, filed Feb. 17, 2014, titled "AN INCUBATOR DEPLOYABLE MULTI-FUNCTIONAL PANEL", of which is hereby incorporated by reference herein in its entirety. An incubator is, in an embodiment, a transport incubator as depicted in U.S. Provisional Pat. Appl. 61/899,233, filed Nov. 3, 2013, titled "A PATIENT TRANSPORT INCUBATOR", of which is hereby incorporated by reference herein in its entirety. Additionally or alternatively, the incubator is designed according to the accepted standards: IEC 601 2 19 Amendment I Medical Electrical Equipment—Part 2: Particular Requirements for Safety of Baby Incubators; IEC 60601-2-20:2009 Medical Electrical Equipment—Part 2: Particular requirements for the basic safety and essential performance of infant transport incubators; and/or ISO 10993-1: 1992 Biological Evaluation of Medical Devices—Part 1: Evaluation and Testing.

In the embodiments of the present invention the term "incubator" can be hereby replaced with any portion of the cart configured to accommodate the neonate, patient or sample to be imaged, such as an upper tray, an incubator, a life supporting incubator, a deployable incubator, a transport incubator, a thermo isolating incubator, a patient bed, a treatment table, a gurney, a tray, a patient placement, a patient chair, a noise isolating patient placement, a vibration isolating patient placement, a light buffering patient placement, a stretcher, a carrying bed, a countertop, and etc.

The term "restraining means" or "means for maintaining the position of the neonate" interchangeably refers hereinafter to any object designed and configured to hold the body position of the neonate, so as to restrict movement of the neonate. This can range from a substantially loose restraining mean limiting only the fall of the neonate from the apparatus or device he/she is connected to (e.g. the incubator, or any cart upper tray), to an almost completely restrictive mean providing complete immobilization of the neonate. Other options are various combinations of immobilizing at least one body part or limb of the neonate. It is important that these means are loose enough in their strictest form to enable breathing and blood flow of the patient neonate. The means are such as straps, immobilization suit, hugger, belt, restraint, flaps, cage, cushions and supports, ergonomic placement, concave shaped sponge like support, bars, and etc. Additionally or alternatively, these means are configured to have an open position in which a neonate can be inserted into, extracted from, or accessed fully, and a closed position immobilizing the patient. Additionally or alternatively these means can include a buckle, switch, snap, loop, latch, and any kind of an opening or closing mechanism.

The term "hinge" interchangeably refers hereinafter to any maneuverable connection for rotational motion between the current invention parts, portions and modules, such as a flexible mechanism or material, joint, hook, thread, axis, juncture, fold, bend, elbow, knee, corner, fork, axis, pole, ball and socket, condyloid joint, mechanical device, fold hinge, joint, bearing, barrel hinge, pivot hinges, butt/mortise hinges, case hinges, continuous hinges, piano hinges, concealed hinges, cup hinge, euro hinge, butterfly hinges, parliament hinges, dovetail hinges, flag hinges, flag hinge, strap hinges, H hinges, HL hinges, counter-flap hinge, flush hinge, coach hinge, rising butt hinge, double action spring hinge, tee hinge, friction hinge, security hinge, cranked hinge, lift-off hinge, self-closing hinge, butt hinge, butler tray hinge, card table hinge, drop leaf table hinge, floating hinge, living hinge, and any combination thereof.

The term "pivot pin" interchangeably refers hereinafter to any maneuverable connection for rotational motion between the current invention parts, portions and modules at least partially around a pivot point.

The term "track", interchangeably refers hereinafter to such as a track, guide, path, groove, rail, line, route, duct, channel, passage, course, trail, lineament, lane, road, seam, length, axis, tract, pathway, course, highway, roadway, alley, artery, avenue, boulevard, clearing, cut, drag, thoroughfare, trajectory, walk, track way, belt, swath, glider, circuit, stretch, runway, caterpillar track, half-track, flat track, soft close track, pivoted sliding track, adjustable track, etc. Further this track maybe a physical or a virtual motion path along which a maneuverable portion is moved.

The term "sliding mechanism", interchangeably refers hereinafter to a mechanism in with a body is movable in a sliding motion along a track. A portion of the movable body is mounted on, suspended from, inserted to, threaded to, interweaved with, integrated to, fitted to, following, etc. a track. In reference to a physical track, the connection of the moveable portion to the track is directly by geometrical shape fit of on part with the other and/or via a third element such as wheels, rack wheels, ball bearings, rollers, rolling discs, lubricant, location guide, belts, pulleys etc. In reference to a virtual motion track, the movable portion is connected to a sliding motion providing mechanism such as telescopic arms, folding arms, arms, angled arms, etc. connected at a pivotal point, allowing for sliding movement along a predefined virtual path. In addition this sliding mechanism may enable straight sliding, curved sliding, folding slide, sliding around a corner, rolling door sliding, etc.

The term "normally deployed" in reference to any of the cart parts, pillar, support, column, interchangeably refers herein after to a description of the state, or position of an element connected in a maneuverable connection (in for example a hinge with a spring loaded system). A normally deployed state is configured so that the moveable mechanism is in a relaxed or resting position when the element is deployed. The position of the element will only change after application of force (for example mechanical force), and will always return to its relaxed deployed position when the application of force is removed. In an embodiment the column has at least one end connected reversibly, and at least one end connected maneuverably, thereby the column can collapse when detaching from the reversibly connected end, and turn or collapse along the maneuverable connection point. In an embodiment, when the column is maneuverably connected to for example the base, the cart upper tray, the pillar, a storage device mounted on the cart and etc. The default position of the column, when deployed, is to stand in a substantially perpendicular to the base, or in any position or vector that carries at least some of the weight of the cart upper tray, or at least partially stabilizes it. Upon application of horizontal force the column collapses around a pivot point at the maneuverable connection point. The column can collapse for example toward the cart base, the cart pillar, a storage device mounted on the cart, towards the device it is connected to, a transport device, and etc. were it can be either at least partially embedded into the base, embedded into a designated placement, collapse on top of the base, or any angle in-between the primary perpendicular position to a horizontal position. In a preferred embodiment, the column has at least one end connected to the cart upper tray (e.g. incubator), this connection could be either reversible or maneuverable. In order to enable maneuverability, one end of the column is connected maneuverably and one end is connected reversibly. In an embodiment, the column is reversibly connected on both ends.

The term "handler" interchangeably refers herein after to any person that is in contact with the incubator such as medical personal, maintenance personal, parent, chaperon and technician.

The term "opening mechanism" or "closing mechanism" interchangeably refers hereinafter to a device designed to transform input forces and movement into such as opening or closing the incubator, movement of the cart towards the MRD, movement of the cart within the MRD, thereby closing the open bore, movement of the collapsible column from a deployed (open) state to a folded, collapsed state (closed). This device may be automatic or manual. Additionally or alternatively, the mechanism is comprises a soft closing device, a push to open device, a connection to hydraulic arms, telescopic arms, a track or rail, oil pressure movement buffering device, a magnetic connection, a lock or cam to stop movement, etc.

The term "automatic" in respect to the movement of a part, a portion and/or a module of the incubator, cart or MRD interchangeably refers herein after to a pre-defined movement having a start location and an end location. This movement could be derived from an engine, a self-sliding movement when a latching mechanism is released, pneumatic mechanism (compressed from the self-sliding movement), hydraulic cylinder, using a gear shift system, etc. Further this movement can be predefined to a specific movement or be steered and manipulated during the action of moving.

The term "manual" in respect to the movement of a part, a portion and/or a module of the incubator, cart or MRD interchangeably refers herein after to any application of force by the handler aimed at maneuvering at least a portion of the incubator or MFP. This force is generated by an action such as pushing, pulling, lifting, levering, turning, twisting, hitting, lowering, etc.

The term "sensor" interchangeably refers hereinafter to any device that receives a signal or stimulus (heat, pressure, light, motion, sound, humidity etc.) and responds to it in a distinctive manner. This manner can be such as inducing the action/inaction of other devices, inducing the action/inaction of indicators (visual, auditable or sensible), inducing the display of the input received by the sensor, inducing the data storage/analysis of input in a central processing unit, etc.

The term "visual indicators" interchangeably refers hereinafter to a representation of light in the visible light range of about 380 nanometers to about 740 nm. More generally the terms refer to any light within the visible range that will be noticeable by the user of the invention (light, flashing light, flickering light, blinking light, change of spectrum of colors of light etc.).

The term "audible indicators" interchangeably refers hereinafter to a representation of sound, typically as an electrical voltage. Audible indicators have frequencies in the audio frequency range of roughly 20 to 20,000 Hz (the limits of human hearing). Audible indicators are either synthesized directly, or originate at a transducer such as a microphone, musical instrument pickup, phonograph cartridge, or tape head.

The term "sensible indicators" interchangeably refers hereinafter to a physical movement of at least a portion of the user interface, which is noticeable to the user (shaking, vibrating, quivering, etc.).

The term "ergonomic" interchangeably refers hereinafter to the design of the incubator to minimize discomfort of the neonate, handler or both. The incubator is designed in a manner that fits the neonate's body and its cognitive needs and abilities. More specifically this term relates to the placement within the inner volume of the incubator to be fitting by means of size, shape, surface properties, sound transmission, light transmission, etc., to be appropriate for maximizing the well-being of the neonate. This term further relates to the human interface of the incubator designed for the handler, parts such as the user interface, open and close mechanisms, overall size and shape, handles, accessibility to the neonate, connections to other equipment, etc., are all designed in a manner that takes into consideration human factors.

The term "life supporting equipment" interchangeably refers hereinafter to any element that provides an environmental condition, a medical condition or monitoring of an environmental or medical condition thereof that assists in sustaining the life of a neonate or bettering their physical and physiological wellbeing. This element can be: (a) any medical equipment: all devices, tubes, connectors, wires, liquid carriers, needles, sensors, monitors, etc., that are used by medical personal in association with the patient. This equipment is such as bilirubin light, an IV (intravenous) pump, oxygen supplementation systems by head hood or nasal cannula, continuous positive airway pressure system, a feeding tube, an umbilical artery catheter, a fluid transport device, hemofiltration system, hemodialysis system, MRI contras solution injection, imaging the neonate etc.; (b) medical measurement and observation systems (including sensors and/or monitors) of temperature, respiration, cardiac function, oxygenation, brain activity such as ECG (electrocardiography) monitor, blood pressure monitor, cardio-respiratory monitor, pulse oximeter; and (c) environmental control systems such as ventilator, air conditioner, humidifier, temperature regulator, climate control systems, noise muffling device, vibration muffling device, etc. and any combination thereof.

The term "medical equipment tubing" interchangeably refers hereinafter to all tubes, cables, connectors, wires, liquid carriers, gas carriers, electrical wires, monitoring cables, viewing cables, data cables, etc., that is used in connection to life support equipment, medical equipment or physical environment maintenance or monitoring.

The term "placement" interchangeably refers hereinafter to a predefined location for placing one or more Item. This is achieved by a mean such as a clip, anchor, catch, clasp, strip, nest, socket, tray, dent, duct, channel, bridge, clamp, harness, concave shape, crater, gap, pocket, recess, grip, belt, catch, snap, fastener, hook, hold, support, buckle, latch, lock, hasp, affixer, binder, joiner, band, ring, string, tie, link, chain, fastener, draw latch, lock, bolt, grip, bar, bond, clasp, connection, fixture, buckle, pin, peg, grapnel, band, pin, insertion, label designation etc.

The term "user interface" interchangeably refers hereinafter to at least one defined area in which the user (patient or handler) interacts with the cart, incubator or MRD. This area harbors elements such as: passage for medical equipment, display, CPU, alarm system, monitoring system, power supply, open mechanism, close mechanism, visual indicators, auditory indicators, sensible indicators, handles, placements, etc. The user interface is designed for the handler, neonate or both.

The term "latching mechanism" interchangeably refers hereinafter to a mechanism such as: fastener, draw latch, latch, lock, belt, bolt, grip, bar, bond, clamp, clasp, connection, fixture, link, hook, hasp, buckle, brake, harness, clip, snap, pin, peg, grapnel, lock, brake mechanism, pin insertion, etc., that is able to lock the configuration of a maneuverable part in respect to another part.

The term "environmental control means" interchangeably refers hereinafter to means to manage and regulate the physical conditions of a predefined area. The physical conditions are such as temperature, radiation, sound, light, ventilation, gas concentration, humidity, movement, texture and softness of materials, etc. These means are either passive (such as isolating materials, refractive materials, filtering materials, etc.), active (such as temperature regulating system, ventilation system, lighting system, sound muffling, sound transmitting, vibration shock absorbers, humidifying, moving, tilting, rocking).

The term "temperature regulating system" interchangeably refers hereinafter to a system that controls the temperature either by heating or by cooling or both. More specifically the term relates to an air conditioned system, an infrared heater, a water/oil-heated radiator, a coiled heater, an open coil air heater, a round open coil air heater, a convection heater, straight or formed tubular heaters, a quartz tube air heater, a capacitor-type heater, a Pelletier module, a refrigerator, vent, etc.

The term "lighting system" interchangeably refers hereinafter to a system that provides lighting to the MBP, to the incubator, to the handler, and any combination thereof. The lighting system can provide a different light spectrum in different locations for example the inner volume of the incubator and the outer environment. Further, this lighting system can be maneuvered manually or automatically to act as spot lights to a specific direction. This system can be configured to have at least two modes, relating to the opened or closed configurations of the incubator. The lighting can be variable in its lighting spectrum wave length (300-1100 nm), the infrared wave length (700 nm-1 mm), the UV wave length (400 nm and 10 nm), and luminous intensity (lm/sr).

The term "power supply" interchangeably refers hereinafter to a source of power such as electrical power generated from internally supplied DC, externally supplied AC or DC, or both.

The term "CPU", central processing unit, interchangeably refers hereinafter to the hardware within a computer that carries out the instructions of a computer program by performing the basic arithmetical, logical, and input/output operations of the system.

The term "modular" interchangeably refers hereinafter to an incubator or panel thereof, which is subdivided into smaller parts (modules) that can be independently created and then used in different embodiments and configurations to drive multiple functionalities.

The term "wheel" interchangeably refers hereinafter to any element providing movement of the cart such as a wheel, roller, drum, disk, cycle, bearing, hoop, ring, belt, sphere, ball, circuit, sliding blade, gyration, caster, ratchet, spoke wheel, being raised by electromagnetic energy, dragging with runners, sled, (or without, travois), being raised by air pressure, caterpillar tracks, pedrail wheels, spheres, alloy wheel, axle, bicycle wheel, caster, pressed steel wheel, hubless wheel, magnetic levitation, mansell wheel, mecanum wheel, omni wheel, rotating locomotion, steering wheel, tire, wire wheels.

The term "compound shape" interchangeably refers hereinafter to any shape that is a result of a combination of at least two shapes.

The term "recess" interchangeably refers hereinafter to any sunken area of the MRD envelope circumference, such as a recess, decayed area, crater, armpit, atrium, basin, chamber, dent, depression, gap, hole, hollow, pit, pocket, sinus, socket, vacuity, conduit, channel, caved area, den, nook, indentation, etc.

The term "storage unit" interchangeably refers hereinafter to a piece of furniture for storing something, this includes any mean designed to house various objects. The storage unit can be such as a cabinet, locker, tray, shelf, container, bottle, rack, case, closet, box, bag, basket, etc.

The term "storage apparatus" interchangeably refers hereinafter to a construct designated to place the present invention, present invention parts, or modules, when not imaged. Usually a storage apparatus can be used when the cart is not accommodated with a patient, and in need of space saving storage, additionally or alternatively the storage device can be used when the cart is accommodated by a patient, in this example the storage device will be placed in a ward of a care taking facility, and will supply an anchor for the cart and accommodated patient. The storage apparatus can further comprise permanent connections to life supporting systems or monitors.

The term "transport device" interchangeably refers hereinafter to a device designated for moving the present invention, the present invention parts, and/or the present invention modules from one location to another location. This can be such as an ambulance, a track, lorry, van, car, golf cart, forklift, cart, carriage, vehicle, wagon, helicopter, airplane, elevator, cable car, escalator, boat, ship, lift, train, trailer, mobile home, caravan, and etc.

The term "electromagnetic interference" interchangeably refers hereinafter to electromagnetic interference (EMI), and radio-frequency interference (RFI), derived from electromagnetic radiation, electromagnetic induction, magnetism, electrostatic fields etc., that affect any electrical circuit, or imaging device such as MRD, NMR, ESR, NQR, CT, US, etc. This interference is derived from any source natural or artificial such as earth magnetic field, atmospheric noise, moving masses of metal, electrical lines, subways, cellular communication equipment, electrical devices, TV and radio stations, elevators, etc. This interference may interrupt, obstruct, degrade, limit, result in false data, etc., the effective performance of the circuit or device.

The term "electromagnetic shielding" refers hereinafter to a practice or device aimed at reducing the electromagnetic field in a space by blocking the field with barriers made of conductive or magnetic materials. The shielding can reduce the effect of radio waves, electromagnetic fields and electrostatic fields. Shielding is typically applied to isolate devices from the external environment, and to cables to isolate wires from the environment through which the cable runs.

The term "RF shielding" refers hereinafter to electromagnetic shielding that blocks radio frequency electromagnetic radiation.

The term "RF filter" interchangeably refers hereinafter to components designed to filter signals in the MHz to GHz frequency ranges. This frequency range is the range used by most broadcast radio, television, wireless communication. These components exert some kind of filtering on the signals transmitted or received. The filters could be active or passive such as waffle-iron filter, mechanical RF filter, etc. RF filters are usually placed when there is need to pass an electrical wire in or out of an MRD enclosure to ensure that the EMI does not couple on the conductive wiring. These filters could be of passive components such as a combination of inductors and capacitors.

The term "RF attenuation properties" interchangeably refers hereinafter to properties that do not allow passage though of defined RF waves. This could be achieved by means such as waveguides designed to attenuate RF, RF filters, attenuating material, etc.

The term "MRI-safe" interchangeably refers herein to any material that, when used in the MR environment, will present no additional risk to the patient and not significantly affect the quality of the diagnostic information. The material is completely non-magnetic, non-electrically conductive, and non-RF reactive, eliminating all of the primary potential threats during an MRI procedure.

The term "care taking facility" interchangeably refers herein to place or institution such as a hospital, an intensive care unit, a nursing home, a home, a rehabilitation center, a day care, a hospital ward, a clinic, a research center, or any place where the patient is residing and receiving care.

The term "treatment table" interchangeably refers herein to any apparatus, device or furniture such as an operating table, a medical treatment table, a technical maintenance apparatus, a designated location in a care taking facility ward, a hygiene apparatus, a patient hygiene apparatus, an imaging table, a physical therapy apparatus, and etc.

Reference is now made to FIG. 1 which discloses in an illustrative manner a premature neonate life support environmental cradle (SEC, 10), adapted by means of shape and size to be accommodated within (i) an incubator (17) for premature neonates (1); and (ii) a measurement device (not shown). The SEC, according to one embodiment of the invention, further comprises an adaptor (11) for connection to a closed life support system (12) for the neonate. The support is one or more member of a group consisting of anesthetic gas, air conditioning, water, food supply, medicines, infusions, electronics, cables to various medical devices etc.

Figures 2A, 2B:
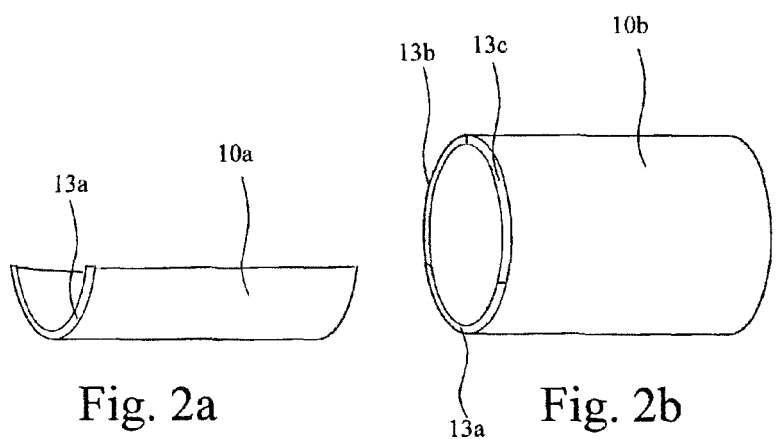
FIGS. 2a and 2b illustrates a SEC in a first at least one open position and a second closed position for accommodating a neonate whilst the SEC is within an incubator, according to some embodiments of the invention.

Reference is now made to FIGS. 2a and 2b which illustrates a SEC which is configured for a first at least one open position (FIG. 2a. 10a) for accommodating the neonate whilst the SEC is within the incubator, and a second closed position (FIG. 2b. 10b) for confinement of the neonate within a sealed volume of incubator atmosphere within the SEC such that the integrity of the confinement is maintained upon removal of the closed SEC containing the neonate from the incubator. This confinement may be constructed to be either fluid tight, air tight etc.

According to one embodiment of the invention, this at least partially reversibly collapsible or deployable structure (10a-10b) is constructed from a plurality of curved or polygonal flaps or sections adapted by means of size and shape to form a continuous envelope having an open bore accommodating the neonate. Here, one flap (13a) forms the cradle and two other flaps (13b and 13c) form the walls.

Figure 3A:
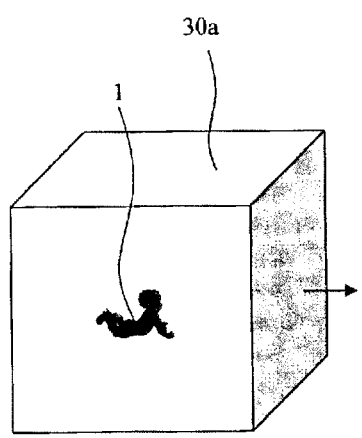
FIGS. 3a and 3b present a prior art two-step procedure.
Figure 3B:
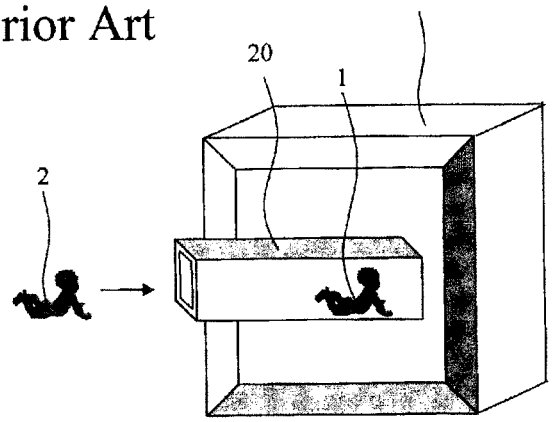

Reference is now made to FIGS. 3a-3b, which present the prior art: a neonate (1) is accommodated within an incubator (10b). Before taking the measurement, e.g., an MRI measurement by means of an MRI (200) positioned in a remote location, the neonate is evacuated from its incubator, and may even be separated from the support system for a short period of time, and then the neonate positioned within an MRI device. In some cases, a specially designed MRI-incubator (20) is used, to support and fix the neonate while taking the measurement. After the measurement is ended, the neonate is evacuated from the measurement device, and again, exposed to the ambient dangerous environment before returning to his incubator. This two-step procedure is thus dangerous for the neonate.

Figure 4:
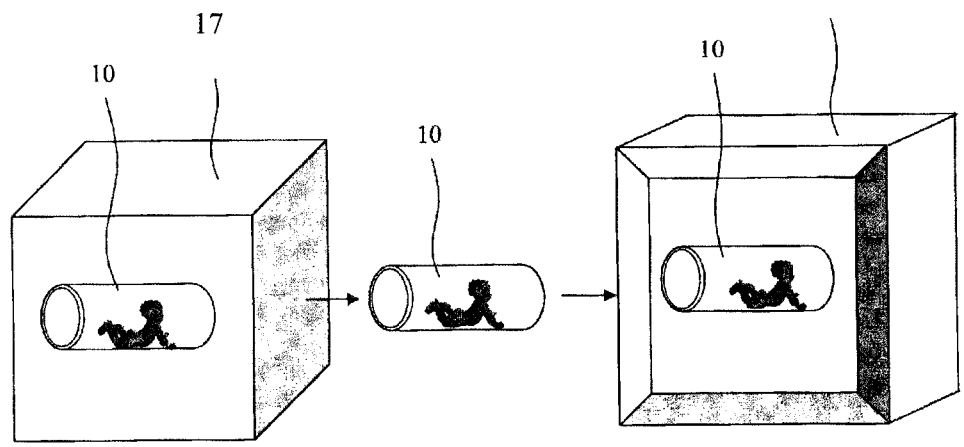
FIG. 4 presents an out-of-scale a one-step procedure according to one embodiment of the invention.

Reference is now made to FIG. 4 which demonstrate the single-step procedure of the present invention, in which medical examinations and measurements are performed using a measurement device without detaching the neonate from the life-support systems, which would endanger his life: The neonate is regularly positioned in an open position SEC within an incubator 17. Before the measurement, the SEC is configured in its closed position (10). Now the neonate, still in connection to the life support systems (not shown), is safely transported within the SEC 10 to a measurement device (17), here an MRI device. SEC 10 is made of materials permeable to magnetism, thus the neonate is fixed and supported in his safe environment. The return of the neonate to its incubator is similarly easy and safe.

FIG. 4 also schematically presents a method of taking measurements of a premature neonate without exposing the same to an environment outside its incubator. This method comprises steps of obtaining a premature neonate life support environmental cradle (SEC, 10), providing the SEC by means of shape and size to be accommodated within (i) an incubator (17) for premature neonates; and (ii) a measurement device (17); placing SEC 10 within incubator 17; opening SEC 10 within incubator 17; accommodating a neonate within the SEC in its at least one open position; before carrying out the measurements, closing SEC 10 within the incubator thereby confining within SEC (i) a volume of incubator 10 atmosphere and (ii) the neonate; exiting SEC 10 in its closed position from incubator 17; and transferring SEC 10 containing the neonate to measurement device (e.g., an MRI device 17) and carrying out the measurements without exposing the neonate to an external environment.

Figure 5:
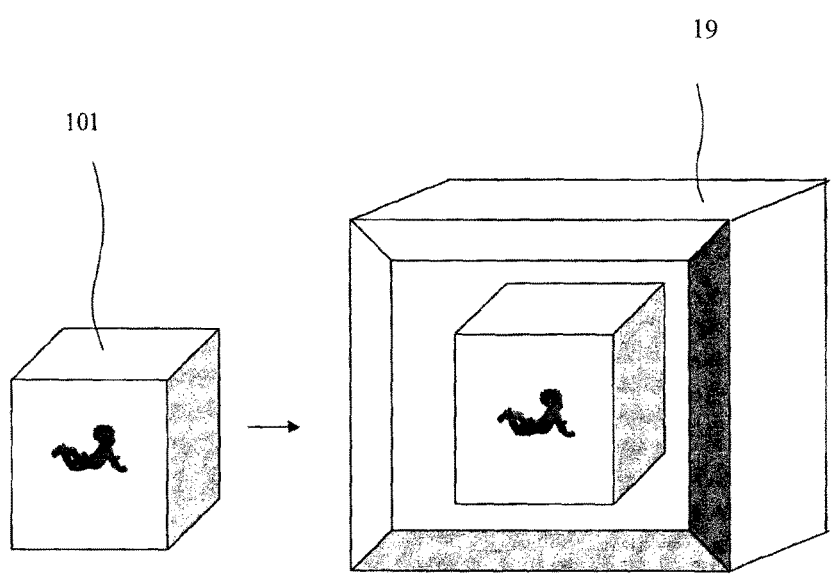
FIG. 5 presents an out-of-scale another one-step procedure and a SEI device according to one embodiment of the invention.

Reference is now made to FIG. 5 which illustrates an MRI-dedicated premature neonate life support incubator (MRI-SEI, 101) according to yet another embodiment of the invention. MRI-SEI (101) is made of magnetically permeable materials. The MRI-SEI is configured for a closed position for confinement of a neonate within a sealed volume of the MRI-SEI such that the integrity of the confinement is maintained upon both (i) transportation of the MRI-SEI containing the neonate to the MRI device (17) and back, and (ii) during the measurement.

FIG. 5 also schematically presents a method of taking measurements of a premature neonate without exposing the same to an environment outside its incubator. The method comprises steps of obtaining the premature neonate life support incubator (SEI, here also 101) adapted by means of shape and size to be accommodated within a measurement device (here also 17); and constructing the SEI with materials that do not interfere with the measurement; configuring the SEI for a closed position for confinement of the neonate within a sealed volume of the SEI; accommodating the neonate within the SEI; before carrying out the measurements, transferring the SEI containing the neonate to the measurement device and carrying out the measurements; without exposing the neonate to an external environment; such that the integrity of the confinement is maintained upon both transportation of the SEI containing the neonate to the measurement device and back and along the measurement.

Figure 6A:
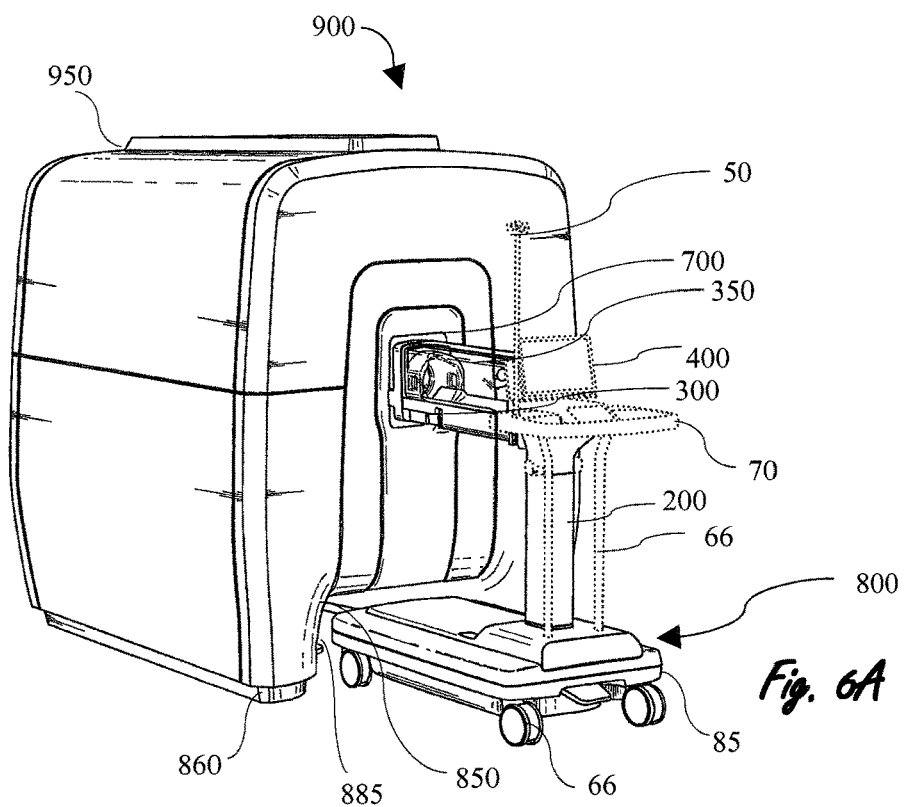
FIG. 6A is a schematic illustration of an MRS having an MRD and an MRI safe cart at least partially insertable within, in a perspective view.

Reference is now made to FIG. 6A schematically illustrating, in an out of scale manner, an embodiment of the invention. An MRS system (900) comprising an MRD (950). At least a portion of an MRD is at least partially encased in an envelope, forming a three dimensional shape. This shape can be any polygon, sphere, cylinder, geometrical, none geometrical, compound shape, curved shape, etc. Following this envelope has an open bore (700) longitudinally on its Z-axis, and additionally or alternatively, have at least one recess (850). Additionally or alternatively, this recess can be located on the front wall of the MRD parallel to the opening of the open bore, on either side (860) of the envelope, under the MRD, or any location in the circumference of the MRD envelope. The recess is sized and shaped to accept at least a portion of the cart. The MRD open bore and the recess are sized and shaped to house at least a portion of an MRI-safe cart. Additionally or alternatively, the open bore is sized and shaped to house at least a portion of the cart upper tray. Additionally or alternatively, the recess is sized and shaped to accept at least a portion of the cart base. Additionally or alternatively, the open bore, recess or both contain a sliding mechanism for assisting in the insertion of at least a portion of the cart, or specifically an incubator, or cart upper tray, a transport incubator, a deployable incubator. Further, the envelope defining the open bore can additionally or alternatively comprise a placement or conduit for the passage of medical equipment tubing. Further this passage is configured to be RF shielding. In one embodiment of the present application the MRD comprises a front wall, having a bore opening sized and shaped to accommodate an incubator or a patient.

Still referring to FIG. 6A, an MRI-safe cart (800) having at least a portion of MRI-safe material, in which a substantially horizontal base (85), and at least one substantially horizontal upper tray embodied as an incubator (300), sized and shaped to accommodate a patient, interconnected by at least one substantially perpendicular pillar (200); the base is of a shape such as rectangular, circular, oval, skeletal, polygonal, compound shape, etc. At least a portion of the cart (800) is sized and shaped to be at least partially housed within the MRD open bore (700), at least one recess (850), or both. Further the base of the cart can be housed at least partially under the MRD, within a recess, at least partially around the MRD, and any combination thereof.

Still referring to FIG. 6A, the present invention provides a cart (800) having a base part (85), an upper tray (300), sized and shaped to accommodate a patient in a life supporting environment, such as an incubator, a deployed incubator, a transport incubator, a treatment table, an operating table, etc., and a pillar (200) interconnecting them. Additionally or alternatively, the base (85) is a lower trolley platform, for maneuvering the cart. Additionally or alternatively, the cart base contains a motion enabling mechanism such as wheels (65), rollers, caterpillar motion device, sliding mechanism, etc. Additionally or alternatively, the cart base contains a placement for medical equipment, an engine, a storage unit, life supporting equipment, etc. Additionally or alternatively, the cart base is of a solid piece, a skeletal structure, a mesh, a frame, etc. The interconnecting pillar is a support configured to mount at least the upper tray or the cart. Additionally or alternatively, the pillar (200) is connected by a maneuverable connection in at least one of its connection points to the cart, providing movement of the pillar around a pivot point, on a sliding mechanism, a hinge, along a joint turn, a rail, a telescopic mechanism enabling different length of the column, etc. Further, the pillar can be connected to the upper tray by means of a joint or hinge allowing movement of the upper tray. Additionally or alternatively, the upper tray is reversibly detachable from the cart. The incubator includes an envelope at least partially surrounding an internal environment. Additionally or alternatively, this envelope contains at least one opening such as at least portion of the envelope connected by a hinge or a joint. Additionally or alternatively, this opening is configured to provide full or partial access to the neonate.

In the embodiments of the present invention the incubator comprises at least one wall that separates the inner volume of the incubator from external surroundings. Additionally or alternatively, the incubator is configured to be fastened to the cart, or as an integral part of it. The incubator-cart system is adapted to accommodate the neonate during MR imaging and can be used as a standard baby incubator in a hospital ward during a routine treatment.

Additionally or alternatively, the upper tray/incubator comprises an ergonomic patient bed, or patient placement, a patient restraint etc. Additionally or alternatively, the cart or any of its parts is ergonomically designed for the handler such as ergonomic handles, operating mechanisms, grips and etc.

Additionally or alternatively, the incubator comprises medical equipment and environmental control systems. Additionally or alternatively, these systems comprise a user interface connected to a control mechanism such as a CPU, to control these systems operation. Further these systems can comprise feedback sensors, or sensors to monitor the patient's condition and the environment status.

Additionally or alternatively, the incubator comprises access ports for nursing care, for the passage of life supporting tubing, life supporting equipment, medical devices, etc. These ports can be designed to hold the tubing and sensors in a fixed position such that they do not move relative to the neonate. In some embodiments of the present invention this can be done by any technique known in the art such as by non-limiting example incorporating rubber grommets or tubing clamps inside the ports. In other embodiments of the present invention the tubing and sensor ports can be designed to have iris configuration.

Additionally or alternatively, the incubator comprises means for securing the position of the patient within, such as straps, hugger, belt, harness, flaps, padding, and etc.

Additionally or alternatively the incubator is designed so that the patient is not exposed to the environmental conditions, but maintained in life supporting conditions. This could be achieved by the incubator comprising life supporting equipment. Further the patient located in an enclosed environment within the incubator so that he is not exposed to infection form the external environment.

In some embodiments of the present invention the incubator comprises an emergency release mechanism to extract the patient within.

In some embodiments of the present invention the incubator panel that closes the bore can comprise high magnetic permeability materials selected from the group consisting of Permalloy, Mu-Metal, ferromagnetic metal with nanocrystalline grain structure. The incubator can serve as a cover for the bore opening when the incubator is inserted inside the MRD. Thus the incubator effectively isolates the magnetic field of the main magnet and prevents from the ferromagnetic objects to be drawn inside the bore. Additionally or alternatively, the cart comprises a panel that closes the MRD bore while imaging; the panel comprises strong physical shielding properties to protect the patient from projectile objects pulled in by the magnet.

According to another embodiment of the invention, an MRI safe cart as defined above is disclosed, comprising a conduit sized and shaped to permit passage of medical equipment tubing from within the MRD open bore to the external environment; the conduit is configured to be of RF shielding properties; wherein at least a portion of the conduit is made of electromagnetic conductive material.

According to another embodiment of the invention, an MRI safe cart as defined above is disclosed, wherein the conduit is interconnected to the cart at least a portion of the perimeter between the cart and the MRD bore aperture.

According to another embodiment of the invention, an MRI safe cart as defined above is disclosed, wherein the conduit comprises an open face toward the MRD external environment, along its longitudinal axis, thereby enabling removal of medical equipment, without detaching it from any of the equipment ends.

According to another embodiment of the invention, an MRI safe cart as defined above is disclosed, wherein the conduit is configured to attenuate electromagnetic interference by means selected from a group of: waveguide, RF filter, waveguide filter, attenuating material, and any combination thereof.

According to another embodiment of the invention, an MRI safe cart as defined above is disclosed, wherein the conduit is configured by means of shape, size and material to attenuate the passage of frequencies selected from a group consisting of: 0-1000 MHz, 0-500 MHz, 0-200 MHz and any combination thereof.

According to another embodiment of the present invention, an MRI safe cart as defined above is disclosed, wherein the cart comprises an RF shielding conduit, as depicted in U.S. Provisional Pat. Appl. 61/905,221, filed Nov. 17, 2013, titled "MM-INCUBATOR'S CLOSURE ASSEMBLY", of which is hereby incorporated by reference herein in its entirety.

According to another embodiment of the present invention, an MRI safe cart as defined above is disclosed, wherein the MRD comprises a self-fastening cage surrounding a magnetic resonance device, as depicted in U.S. Pat. No. 7,719,279 B2, filed May 27, 2008 titled: "SELF-FASTENING CAGE SURROUNDING A MAGNETIC RESONANCE DEVICE AND METHODS THEREOF", of which is hereby incorporated by reference in its entirety.

Still referring to FIG. 6A, further embodied in the present invention is at least one additional support (66). This support may be of a shape of a rod, plank, shaft, frame, geometrical, non-geometrical, flexible, none flexible shape. The support (66) described in FIG. 6A, is a support connecting the handle (70) to the cart base (85). Additionally or alternatively, a collapsible support column/rod is connected to the upper tray, further connecting the upper tray to the base (85), the pillar (200), at least a portion of the MRD, a transport device such as an ambulance, a wall, a medical instrument, an element in an operating room, a treatment area, etc. Additionally or alternatively, the collapsible support column is connected by a maneuverable connection in at least one of its connection points to the cart, providing movement of the column around a pivot point, on a sliding mechanism, a hinge, along a joint turn, a rail, a telescopic mechanism enabling different length of the column, etc. Additionally or alternatively, the collapsible support column is detachably connected at its upper end to a lower side of the mounting on one side and to the upper end of the base on its other side. Thus, the column prevents torque being applied to the incubator when the fastened incubator is being transported on the cart. The column is adapted to be connected by a spring at its lower part to the platform. Thus the column is configured to be reversibly collapsible when the incubator is being inserted inside the MRD bore opening. The reversibly collapsible rod/column is adapted to be operatively connected to the trolley by means such as a spring mechanism, a hydraulic mechanism, a telescopic mechanism, an oil pressure mechanism, etc.; spring selected from the group consisting of tension spring, extension spring, compression spring, torsion spring, constant spring, variable spring, coil spring, flat spring, machined spring, cantilever spring, volute spring, balance spring, leaf spring, v-spring, belleville spring, constant-force spring, gas spring, mainspring, negator spring, progressive rate coil springs, rubber band, wave spring. In the embodiments of the present invention the column's cross section can have various polygonal shapes. In other embodiments of the present invention the trolley platform comprises moving parts selected from the group consisting of wheels, rollers and caterpillars. In some embodiments of the present invention the rod can be configured to be automatically, semi-automatically or manually reversibly collapsible when the incubator is being inserted inside the MRD. Furthermore the column can be also automatically, semi-automatically or manually detachable from the lower side of the mounting when the incubator is being inserted inside the MRD.

In some embodiments of the present invention a front part of the platform can comprise a yoke having two forward extending legs configured to embrace the MRD (950) from the side of the front wall, or in a designated recess (860), when the fastened incubator is being inserted into the bore opening.

Still referring to FIG. 6A, the cart can hold a user interface including a selected from a group consisting of a screen (400), a CPU, indicators, connecting sensors, an alarm system, keyboard, touch screen, mouse, data communication port, voice activation, a viewing system for viewing the neonate, and any combination thereof. Additionally or alternatively the cart comprises sensors that are configured to sense temperature, vibration, humidity, RF signals, sound levels, medical condition of the neonate, and structural integrity of the cart, incubator, MRD or any embedded system. Additionally or alternatively the sensors are connected to a CPU, indicators (visual, sensible, auditable), and/or an alarm system.

Figure 6B:
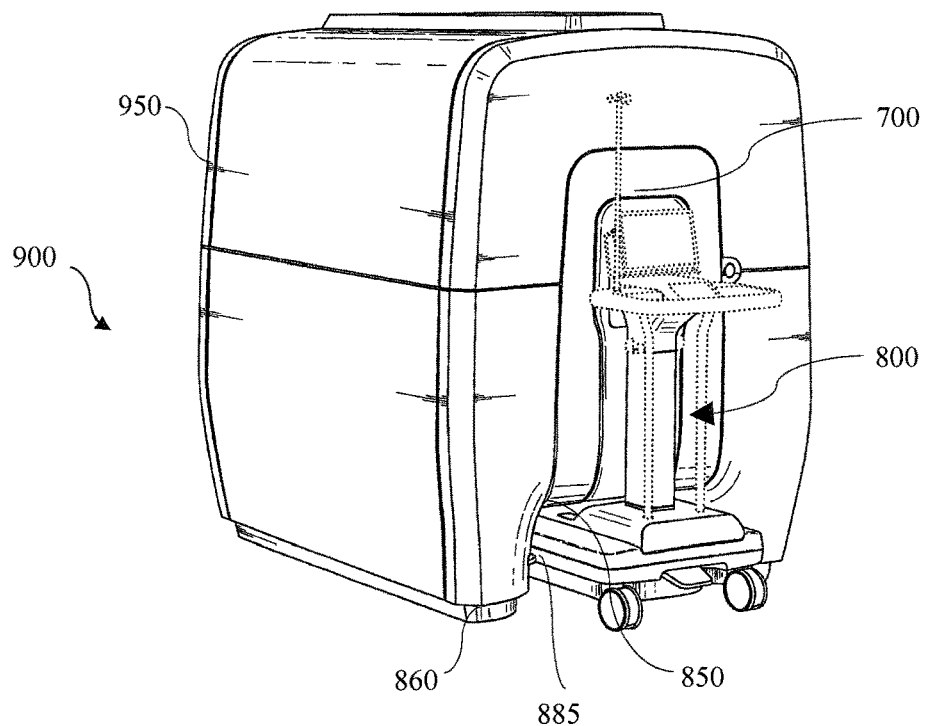
FIG. 6B is a schematic illustration of an MRS having an MRD and an MRI safe cart at least partially insertable within, in a perspective view.

Reference is now made to FIG. 6B schematically illustrating, in an out of scale manner, an embodiment of the invention. An MRS (900) having an MRD (950), in which an open bore (700) along it longitudinal Z-axis, a recess (850) in its lower part, having a sliding mechanism (855), and an inserted MRI-safe cart (800), sized and shaped so the upper tray harboring an incubator or sized and shaped to be an incubator, is at least partially intercepted or housed within the open bore, and at least a portion of the base is partially intercepted or housed within the recess.

According to one embodiment of the present invention, a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD, and further wherein at least a portion of the base is reversibly housed within at least one recess.

According to another embodiment of the invention, an MRS as defined above is disclosed, wherein the MRD comprises a self-fastening cage surrounding a magnetic resonance device.

According to another embodiment of the invention, an MRS as defined above is disclosed, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a light buffering patient placement, a stretcher, a carrying bed, an ergonomic patient placement, a patient restraint, and any combination thereof.

According to another embodiment of the invention, an MRS as defined above is disclosed, wherein the cart incubator is connected to the cart by a maneuverable connection enabling movement selected from a group consisting of: rotational, linear horizontal, linear vertical, tilting, oscillating movement, and any combination thereof.

According to another embodiment of the invention, an MRS as defined above is disclosed, wherein the incubator is reversibly connected to the cart.

According to another embodiment of the invention, an MRS as defined above is disclosed, wherein the cart comprises an MRI-incubator's closure assembly.

According to another embodiment of the invention, an MRS as defined above is disclosed, wherein the cart is configured to sealingly enclose the MRD open bore when at least a portion thereof is housed within the MRD.

According to another embodiment of the invention, an MRS as defined above is disclosed, wherein at least a portion of the MRS comprises a material selected from a group consisting of: MRI-safe material, sterilizable material, at least a partially transparent material, and any combination thereof.

According to another embodiment of the invention, an MRS as defined above is disclosed, wherein the cart, the MRD or both, comprises a plurality of life supporting equipment, medical equipment placement, or both.

According to another embodiment of the invention, an MRS as defined above is disclosed, wherein the cart pillar is maneuverably connected to the cart incubator, the cart base, or both.

According to another embodiment of the invention, an MRS as defined above is disclosed, wherein the cart comprises at least one support, connecting the incubator to a selected from a group consisting of: the pillar, a wall, a transport device, the MRD, a storage unit, a floor and any combination thereof.

According to another embodiment of the invention, an MRS as defined above is disclosed, wherein the cart pillar is reversibly connected to an element selected from a group consisting of: the cart upper tray, the cart base, at least one support, a least one storage unit, and any combination thereof.

According to another embodiment of the invention, an MRS as defined above is disclosed, wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

According to another embodiment of the invention, an MRS as defined above is disclosed, wherein the column is configured to be normally deployed.

According to another embodiment of the invention, an MRS as defined above is disclosed, wherein the column is collapsible upon application of horizontal force in the axis parallel to the open bore.

According to another embodiment of the invention, an MRS as defined above is disclosed, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

According to another embodiment of the invention, an MRS as defined above is disclosed, wherein the at least one column end is reversibly connectable to at least two locations selected from a group consisting of: the cart base, the cart upper tray, the cart pillar, a storage unit, a wall, a transport device, and any combination thereof.

According to another embodiment of the invention, an MRS as defined above is disclosed, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

According to another embodiment of the invention, an MRS as defined above is disclosed, wherein the column is at least partially reversibly collapsible into or onto an element selected from a group consisting of: the base, the upper tray, the pillar, when the cart is at least partially intercepted within the MRD.

According to another embodiment of the invention, an MRS as defined above is disclosed, wherein the column is at least partially reversibly collapsible into or onto an element selected from a group consisting of: the base, the upper tray, the pillar, when force is applied on the column.

According to another embodiment of the invention, an MRS as defined above is disclosed, wherein the column is at least partially embedded within a selected from a group consisting of: the base, the upper tray, the pillar, or any combination thereof, when in folded or collapsible positions.

According to another embodiment of the invention, an MRS as defined above is disclosed, wherein the column comprises a telescopic or folding mechanism, thereby enabling different length of the column.

According to another embodiment of the invention, an MRS as defined above is disclosed, wherein the at least apportion of the column is made of a material selected from a group consisting of: MRI-safe material, recyclable material, sterilizable material, fire retardant material, and any combination thereof.

According to another embodiment of the invention, an MRS as defined above is disclosed, wherein the column is of a shape selected from a group consisting of: rod, cylinder, multifaceted shape, rectangular, geometric, non-geometric, curved, compound shape, fork-like, and any combination thereof.

According to another embodiment of the invention, an MRS as defined above is disclosed, wherein the column maintains stability of the upper tray in a horizontal or reclined position.

According to another embodiment of the invention, an MRS as defined above is disclosed, wherein a selected from a group consisting of: the column, the MRD, the cart and any combination thereof, comprises at least one latching mechanism configured to hold at least one first position of the column.

According to another embodiment of the invention, an MRS as defined above is disclosed, wherein the cart base is of a fork like shape, having a recess sized and fitted to house the at least a portion of the MRD.

According to another embodiment of the invention, an MRS as defined above is disclosed, wherein the cart's base comprises at least one protrusion sized and shaped to be inserted at least partially into or under the MRD.

According to another embodiment of the invention, an MRS as defined above is disclosed, wherein the MRD comprises an envelope at least partially encasing the MRD, and at least one recess in the circumference of the envelope sized and shaped to accept at least a portion of the cart.

According to another embodiment of the invention, an MRS as defined above is disclosed, wherein the at least one recess is selected from a group consisting of: parallel to the open bore, perpendicular to the open bore, in an angle to the open bore, and any combination thereof.

According to another embodiment of the invention, an MRS as defined above is disclosed, wherein the recess is sized and shaped as a mold of at least a portion of the cart.

According to another embodiment of the invention, an MRS as defined above is disclosed, wherein the recess comprises a rail or track along which the base is at least partially housed.

According to another embodiment of the invention, an MRS as defined above is disclosed, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

According to another embodiment of the invention, an MRS as defined above is disclosed, wherein the MRD comprises a selected from a group consisting of: a sliding mechanism, a rail, a guide, and any combination thereof configured to slide the cart at least partially into the MRD.

According to another embodiment of the invention, an MRS as defined above is disclosed, wherein the track comprises wheels or rollers.

According to another embodiment of the invention, an MRS as defined above is disclosed, wherein the movement of the cart into the MRD is controlled by a mechanism selected from a group consisting of: manual, automatic or any combination thereof.

According to another embodiment of the invention, an MRS as defined above is disclosed, wherein the MRD, the cart, or both comprise an emergency release mechanism, to extract the neonate accommodated within.

According to another embodiment of the invention, an MRS as defined above is disclosed, wherein the MRD, the cart or both comprise a lighting system.

According to another embodiment of the invention, an MRS as defined above is disclosed, wherein the cart comprises an RF shielding conduit sized and shaped for the passage of medical equipment tubing.

According to another embodiment of the invention, an MRS as defined above is disclosed, wherein the cart, the MRD or both, comprises a plurality of medical equipment, medical equipment placing, or both.

According to another embodiment of the invention, an MRS as defined above is disclosed, an MRS as defined above is disclosed, wherein the cart, the MRD or both, comprises an RF detection mechanism.

According to another embodiment of the invention, an MRS as defined above is disclosed, wherein the cart, the MRD or both, comprises at least one handle.

According to another embodiment of the invention, an MRS as defined above is disclosed, wherein at least a portion of the cart is foldable thereby minimizing storage space.

According to another embodiment of the invention, an MRS as defined above is disclosed, wherein at least a portion of the cart is constructed of modular reversibly connecting pieces.

According to another embodiment of the invention, an MRS as defined above is disclosed, wherein the pillar is sized and shaped to provide structural support to the incubator situated in a substantially horizontal plain parallel to the base.

According to another embodiment of the invention, an MRS as defined above is disclosed, wherein the pillar is reversibly connected to an element selected from a group consisting of the incubator, the base, at least one support, a least one storage unit and any combination thereof.

According to another embodiment of the invention, an MRS as defined above is disclosed, wherein the pillar is of a fork like shape having at least two connecting points to the upper tray, the base or both.

According to another embodiment of the invention, an MRS as defined above is disclosed, wherein the pillar is of a shape selected from a group consisting of cylindered, quadrangular, geometrical, none geometrical, multifaceted shape, smooth-lined shape, compound shape comprised of multiple pieces, and any combination thereof.

According to another embodiment of the invention, an MRS as defined above is disclosed, wherein the pillar is telescopic configured to provide an adjustable height of the patient's bed.

According to another embodiment of the invention, an MRS as defined above is disclosed, wherein the pillar is connected to the base, the upper tray or both, by a rotating mechanism.

According to another embodiment of the invention, an MRS as defined above is disclosed, wherein the pillar is rotated together with the upper tray or with the base.

According to another embodiment of the invention, an MRS as defined above is disclosed, wherein the pillar is at least partially hollow and comprises a conduit sized and shaped for the passage of medical equipment tubing.

According to another embodiment of the invention, an MRS as defined above is disclosed, wherein the pillar is further connected to at least one storage tray, at least one storage unit or both.

According to another embodiment of the invention, an MRS as defined above is disclosed, wherein the cart's base comprises at least one wheel.

According to another embodiment of the invention, an MRS as defined above is disclosed, wherein the cart comprises a motion stopping mechanism, e.g. wheel brakes.

According to another embodiment of the invention, an MRS as defined above is disclosed, wherein the cart's base is substantially of a shape selected from a group consisting of: rectangle, oval, round, triangular, geometric, none geometric, multifaceted, having smooth rounded edges, compound shape, a hollow frame, a shape frame and any combination thereof.

According to another embodiment of the invention, an MRS as defined above is disclosed, wherein the upper tray or incubator is substantially of a shape selected from a group consisting of: rectangle, a cube, a sphere, box, egg like, oval, round, triangular, geometric, none geometric, multifaceted, having smooth rounded edges, compound shape, a hollow frame, a shape frame and any combination thereof.

According to another embodiment of the invention, an MRS as defined above is disclosed, wherein the cart, the MRD or both comprise a user interface.

According to another embodiment of the invention, an MRS as defined above is disclosed, wherein the cart, the MRD or both comprising a CPU connected to a user interface.

According to another embodiment of the invention, an MRS as defined above is disclosed, wherein the cart user interface is configured to control the MRD operating system.

According to another embodiment of the invention, an MRS as defined above is disclosed, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

According to another embodiment of the invention, an MRS as defined above is disclosed, wherein the sensor is connected to a selected from a group consisting of: a sensible indicator, a visual indicator, an auditable indicator, a CPU, a user interface, a control panel, According to another embodiment of the invention, an MRS as defined above is disclosed, wherein the cart comprises an installable RF coil assembly.

According to another embodiment of the invention, an MRS as defined above is disclosed, wherein the cart comprising a comprising at least one RF shielding conduit, connected to the cart; sized and shaped to allow passage of medical equipment tubing from the MRD bore to the external environment; further wherein the conduit is characterized by a length (l) and a width (w) l:w ratio is greater than a predefined value n, thereby providing RF shielding; where the numerical value of n is selected from a group consisting of: $2.5<n<6$, $4<n<6$, $4<n<9$ and any combination thereof.

According to another embodiment of the invention, an MRS as defined above is disclosed, wherein the MRD open bore is of a shape selected from a group consisting of: cylindered, quadrangular, geometrical, none geometrical, multifaceted shape, smooth-lined shape, and any combination thereof.

Figure 7:
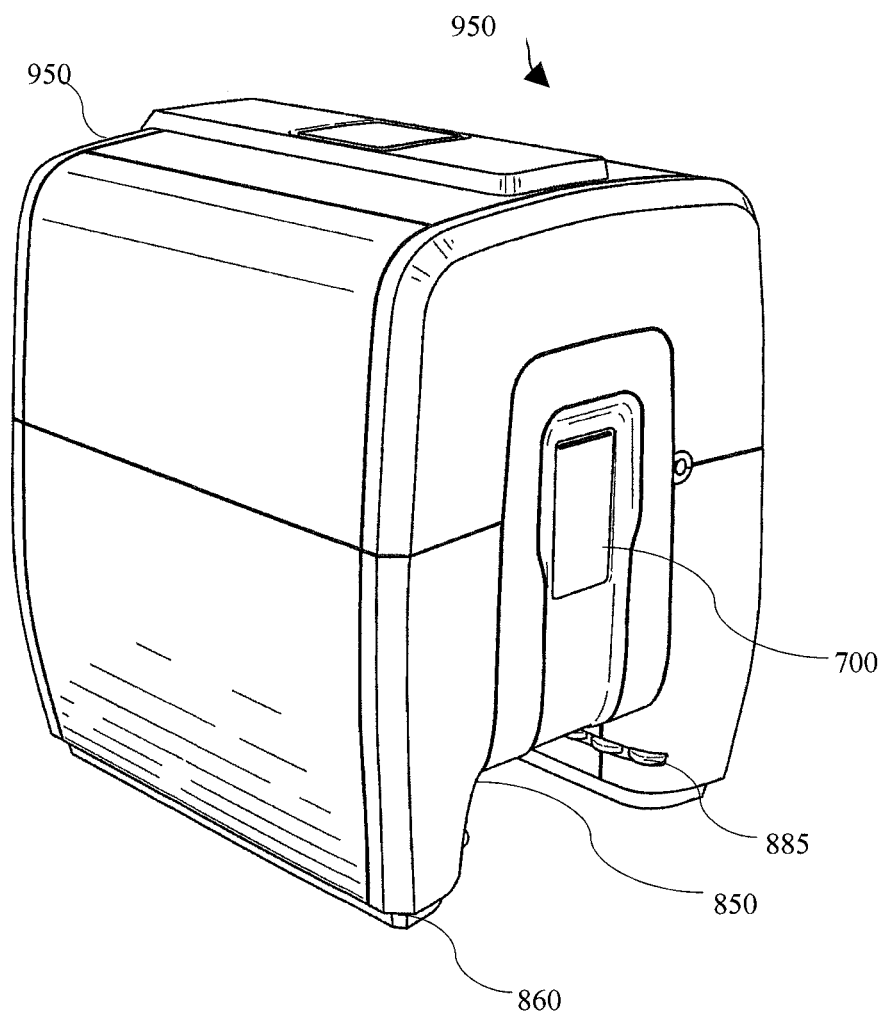
FIG. 7 is a schematic illustration of an MRD in a perspective view.

Reference is now made to FIG. 7 schematically illustrating, in an out of scale manner, an embodiment of the invention. An MRD (950) in a perspective view. The MRD (950) having an envelope encasing the MRD components, in which an open bore (700) therethrough in the longitudinal Z axis, at least a partially parallel recess (850), and another recess on the side (860). Within at least one of the cavities (850) is a sliding mechanism, which eases the insertion of an MRI safe cart sized and shaped to at least partially fit within at least portion of the open bore (700) and at least a portion of the recess. At least a portion of the MRD comprises a selected from a group consisting of: at least a partially transparent material, conductive material, sealing material, MRI safe material, isolating material, RF attenuating materials, and any combination thereof.

According to one embodiment of the invention, a magnetic resonance device (MRD), useful for imaging a patient, at least partially contained in an envelope comprising an open bore, and at least one recess in the circumference of the envelope, wherein the MRD is configured to fit at least partially an MRI safe cart, made of MRI-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within the at least one recess.

According to another embodiment of the invention, an MRD as defined above is disclosed, wherein the MRD comprises a self-fastening cage surrounding a magnetic resonance device.

According to another embodiment of the invention, an MRD as defined above is disclosed, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

According to another embodiment of the invention, an MRD as defined above is disclosed, wherein the cart incubator is connected to the cart by a maneuverable connection enabling movement selected from a group consisting of: rotational, linear horizontal, linear vertical, tilting, oscillating movement, and any combination thereof.

According to another embodiment of the invention, an MRD as defined above is disclosed, wherein the incubator is reversibly connected to the cart.

According to another embodiment of the invention, an MRD as defined above is disclosed, wherein the cart comprises an MRI-incubator's closure assembly.

According to another embodiment of the invention, an MRD as defined above is disclosed, wherein the cart is configured to sealingly enclose the MRD open bore when at least a portion thereof is housed within the MRD.

According to another embodiment of the invention, an MRD as defined above is disclosed, wherein at least a portion of the MRS comprises a material selected from a group consisting of: MRI-safe material, sterilizable material, at least a partially transparent material, and any combination thereof.

According to another embodiment of the invention, an MRD as defined above is disclosed, wherein the cart, the MRD or both, comprises a plurality of life supporting equipment, medical equipment placement, or both.

According to another embodiment of the invention, an MRD as defined above is disclosed, wherein the cart pillar is maneuverably connected to the cart incubator, the cart base, or both.

According to another embodiment of the invention, an MRD as defined above is disclosed, wherein the cart comprises at least one support, connecting the incubator to a selected from a group consisting of: the pillar, a wall, a transport device, the MRD, a storage unit, a floor and any combination thereof.

According to another embodiment of the invention, an MRD as defined above is disclosed, wherein the cart pillar is reversibly connected to an element selected from a group consisting of: the cart upper tray, the cart base, at least one support, a least one storage unit, and any combination thereof.

According to another embodiment of the invention, an MRD as defined above is disclosed, wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof. According to another embodiment of the invention, an MRD as defined above is disclosed, wherein the column is configured to be normally deployed.

According to another embodiment of the invention, an MRD as defined above is disclosed, wherein the column is collapsible upon application of horizontal force in the axis parallel to the open bore.

According to another embodiment of the invention, an MRD as defined above is disclosed, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

According to another embodiment of the invention, an MRD as defined above is disclosed, wherein the at least one column end is reversibly connectable to at least two locations selected from a group consisting of: the cart base, the cart upper tray, the cart pillar, a storage unit, a wall, a transport device, and any combination thereof.

According to another embodiment of the invention, an MRD as defined above is disclosed, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

According to another embodiment of the invention, an MRD as defined above is disclosed, wherein the column is at least partially reversibly collapsible into or onto an element selected from a group consisting of: the base, the upper tray, the pillar, when the cart is at least partially intercepted within the MRD.

According to another embodiment of the invention, an MRD as defined above is disclosed, wherein the column is at least partially reversibly collapsible into or onto an element selected from a group consisting of: the base, the upper tray, the pillar, when force is applied on the column.

According to another embodiment of the invention, an MRD as defined above is disclosed, wherein the column is at least partially embedded within a selected from a group consisting of: the base, the upper tray, the pillar, or any combination thereof, when in folded or collapsible positions.

According to another embodiment of the invention, an MRD as defined above is disclosed, wherein the column comprises a telescopic or folding mechanism, thereby enabling different length of the column.

According to another embodiment of the invention, an MRD as defined above is disclosed, wherein the at least apportion of the column is made of a material selected from a group consisting of: MRI-safe material, recyclable material, sterilizable material, fire retardant material, and any combination thereof.

According to another embodiment of the invention, an MRD as defined above is disclosed, wherein the column is of a shape selected from a group consisting of: rod, cylinder, multifaceted shape, rectangular, geometric, non-geometric, curved, compound shape, fork-like, and any combination thereof.

According to another embodiment of the invention, an MRD as defined above is disclosed, wherein the column maintains stability of the upper tray in a horizontal or reclined position.

According to another embodiment of the invention, an MRD as defined above is disclosed, wherein a selected from a group consisting of: the column, the MRD, the cart and any combination thereof, comprises at least one latching mechanism configured to hold at least one first position of the column.

According to another embodiment of the invention, an MRD as defined above is disclosed, wherein the cart base is of a fork like shape, having a recess sized and fitted to house the at least a portion of the MRD.

According to another embodiment of the invention, an MRD as defined above is disclosed, wherein the cart's base comprises at least one protrusion sized and shaped to be inserted at least partially into or under the MRD.

According to another embodiment of the invention, an MRD as defined above is disclosed, wherein the MRD comprises an envelope at least partially encasing the MRD, and at least one recess in the circumference of the envelope sized and shaped to accept at least a portion of the cart.

According to another embodiment of the invention, an MRD as defined above is disclosed, wherein the at least one recess is selected from a group consisting of: parallel to the open bore, perpendicular to the open bore, in an angle to the open bore, and any combination thereof.

According to another embodiment of the invention, an MRD as defined above is disclosed, wherein the recess is sized and shaped as a mold of at least a portion of the cart.

According to another embodiment of the invention, an MRD as defined above is disclosed, wherein the recess comprises a rail or track along which the base is at least partially housed.

According to another embodiment of the invention, an MRD as defined above is disclosed, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

According to another embodiment of the invention, an MRD as defined above is disclosed, wherein the MRD comprises a selected from a group consisting of: a sliding mechanism, a rail, a guide, and any combination thereof configured to slide the cart at least partially into the MRD.

According to another embodiment of the invention, an MRD as defined above is disclosed, wherein the track comprises wheels or rollers.

According to another embodiment of the invention, an MRD as defined above is disclosed, wherein the movement of the cart into the MRD is controlled by a mechanism selected from a group consisting of: manual, automatic or any combination thereof.

According to another embodiment of the invention, an MRD as defined above is disclosed, wherein the MRD, the cart, or both comprise an emergency release mechanism, to extract the neonate accommodated within.

According to another embodiment of the invention, an MRD as defined above is disclosed, wherein the MRD, the cart or both comprise a lighting system.

According to another embodiment of the invention, an MRD as defined above is disclosed, wherein the cart comprises an RF shielding conduit sized and shaped for the passage of medical equipment tubing.

According to another embodiment of the invention, an MRD as defined above is disclosed, wherein the cart, the MRD or both, comprises a plurality of medical equipment, medical equipment placing, or both.

According to another embodiment of the invention, an MRD as defined above is disclosed, wherein the cart, the MRD or both, comprises an RF detection mechanism.

According to another embodiment of the invention, an MRD as defined above is disclosed, wherein the cart, the MRD or both, comprises at least one handle.

According to another embodiment of the invention, an MRD as defined above is disclosed, wherein at least a portion of the cart is foldable thereby minimizing storage space.

According to another embodiment of the invention, an MRD as defined above is disclosed, wherein at least a portion of the cart is constructed of modular reversibly connecting pieces.

According to another embodiment of the invention, an MRD as defined above is disclosed, wherein the pillar is sized and shaped to provide structural support to the incubator situated in a substantially horizontal plain parallel to the base.

According to another embodiment of the invention, an MRD as defined above is disclosed, wherein the pillar is reversibly connected to an element selected from a group consisting of the incubator, the base, at least one support, a least one storage unit and any combination thereof.

According to another embodiment of the invention, an MRD as defined above is disclosed, wherein the pillar is of a fork like shape having at least two connecting points to the upper tray, the base or both.

According to another embodiment of the invention, an MRD as defined above is disclosed, wherein the pillar is of a shape selected from a group consisting of cylindered, quadrangular, geometrical, none geometrical, multifaceted shape, smooth-lined shape, compound shape comprised of multiple pieces, and any combination thereof.

According to another embodiment of the invention, an MRD as defined above is disclosed, wherein the pillar is telescopic configured to provide an adjustable height of the patient's bed.

According to another embodiment of the invention, an MRD as defined above is disclosed, wherein the pillar is connected to the base, the upper tray or both, by a rotating mechanism.

According to another embodiment of the invention, an MRD as defined above is disclosed, wherein the pillar is rotated together with the upper tray or with the base.

According to another embodiment of the invention, an MRD as defined above is disclosed, wherein the pillar is at least partially hollow and comprises a conduit sized and shaped for the passage of medical equipment tubing.

According to another embodiment of the invention, an MRD as defined above is disclosed, wherein the pillar is further connected to at least one storage tray, at least one storage unit or both.

According to another embodiment of the invention, an MRD as defined above is disclosed, wherein the cart's base comprises at least one wheel.

According to another embodiment of the invention, an MRD as defined above is disclosed, wherein the cart comprises a motion stopping mechanism, e.g. wheel brakes.

According to another embodiment of the invention, an MRD as defined above is disclosed, wherein the cart's base is substantially of a shape selected from a group consisting of: rectangle, oval, round, triangular, geometric, none geometric, multifaceted, having smooth rounded edges, compound shape, a hollow frame, a shape frame and any combination thereof.

According to another embodiment of the invention, an MRD as defined above is disclosed, wherein the upper tray or incubator is substantially of a shape selected from a group consisting of: rectangle, a cube, a sphere, box, egg like, oval, round, triangular, geometric, none geometric, multifaceted, having smooth rounded edges, compound shape, a hollow frame, a shape frame and any combination thereof.

According to another embodiment of the invention, an MRD as defined above is disclosed, wherein the cart, the MRD or both comprise a user interface.

According to another embodiment of the invention, an MRD as defined above is disclosed, wherein the cart, the MRD or both comprising a CPU connected to a user interface.

According to another embodiment of the invention, an MRD as defined above is disclosed, wherein the cart user interface is configured to control the MRD operating system.

According to another embodiment of the invention, an MRD as defined above is disclosed, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

According to another embodiment of the invention, an MRD as defined above is disclosed, wherein the sensor is connected to a selected from a group consisting of: a sensible indicator, a visual indicator, an auditable indicator, a CPU, a user interface, a control panel, According to another embodiment of the invention, an MRD as defined above is disclosed, wherein the cart comprises an installable RF coil assembly.

According to another embodiment of the invention, an MRD as defined above is disclosed, wherein the cart comprising a comprising at least one RF shielding conduit, connected to the cart; sized and shaped to allow passage of medical equipment tubing from the MRD bore to the external environment; further wherein the conduit is characterized by a length (l) and a width (w) l:w ratio is greater than a predefined value n, thereby providing RF shielding; where the numerical value of n is selected from a group consisting of: 2.5<n<6, 4<n<6, 4<n<9 and any combination thereof.

According to another embodiment of the invention, an MRD as defined above is disclosed, wherein the MRD open bore is of a shape selected from a group consisting of: cylindered, quadrangular, geometrical, none geometrical, multifaceted shape, smooth-lined shape, and any combination thereof.

Figure 8A:
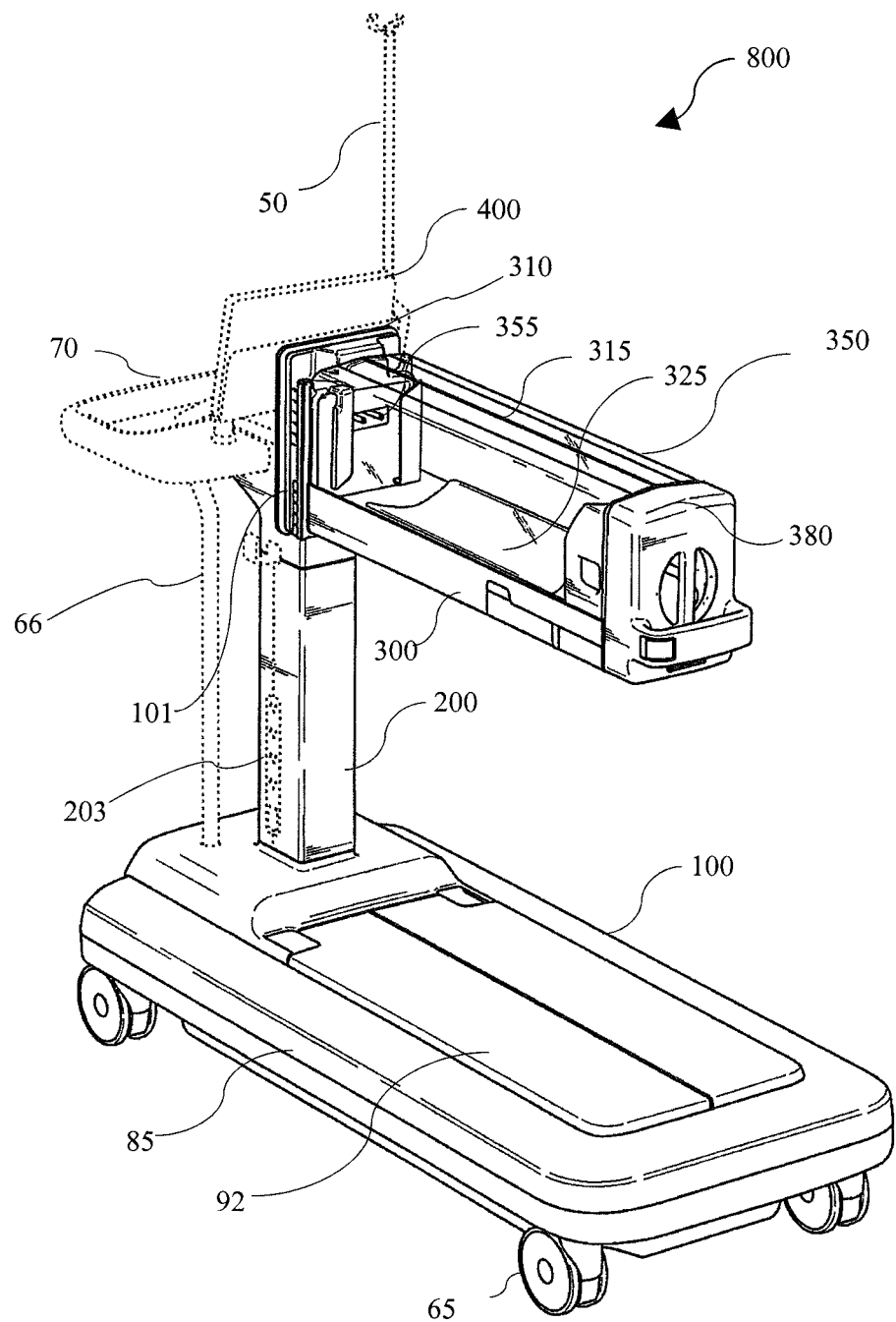
FIG. 8A is a schematic illustration of an MRI safe cart in a perspective view.

Reference is now made to FIG. 8A schematically illustrating, in an out of scale manner, an embodiment of the invention. An MRI safe cart (800) in a perspective view. The cart includes a base (85), embodied as a trolley base, harboring at least one wheel (65). In this embodiment the base comprises reversibly connected flaps (92), providing for example either a shelf in a closed position or enabling insertion of a third party element such as a storage compartment or medical equipment when opened. Further the cart comprises an upper tray (300) embodied as an incubator, having an envelope (350) surrounding an inner volume. Additionally or alternatively, the incubator comprises an installable RF coil assembly (380). Additionally or alternatively the incubator comprises a placement for the patient (325), opening top flaps (315), an opening for insertion of tubing (355), a closure for the MRD (101) constructed having an RF shielding conduit (310), a computer with a user interface (400), placement for medical equipment (50) such as an I.V. infusion bag, a handle (70) or any combination thereof. The substantially horizontal upper tray (300) is interconnected to the base (85) with a substantially perpendicular pillar (200). The pillar can be hollow or full, and of a shape such as rectangular, cylindered, multi-faced, curved, geometric, non-geometric, etc. the pillar can include a placement for tubing, or an electric current connection (or any power supply) (203). The handle can be further stabled by an accessory support (66) interconnecting the computer unit (400) and or the handle (70) to the base (85).

Figure 8B:
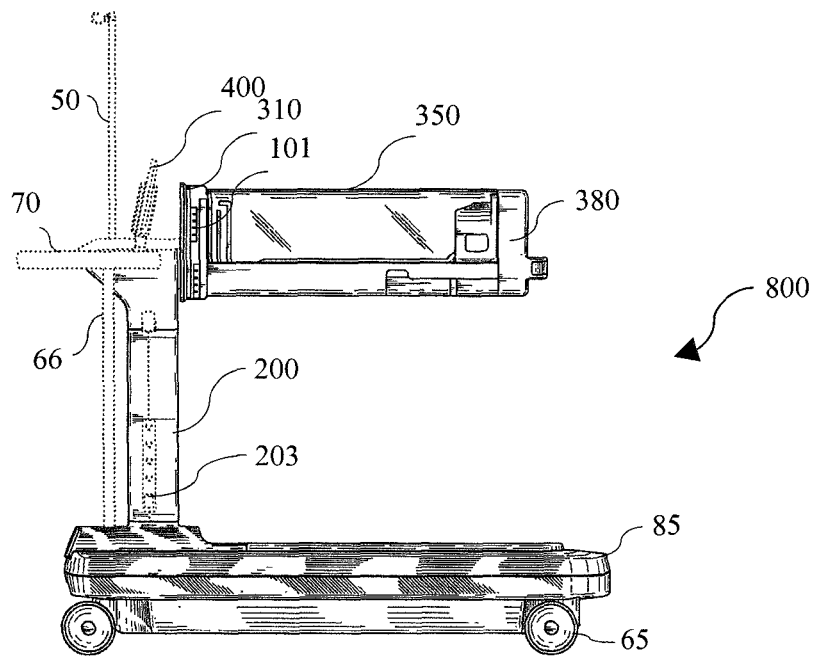
FIG. 8B is a schematic illustration of a cart in a side view.

Reference is now made to FIG. 8B schematically illustrating, in an out of scale manner, an embodiment of the invention. A cart (800) in a side view. A substantially horizontal base (85), connected to a motion enabling element such as a wheel (65), a pillar (200), having a port for electrical and medical tubing (203), connecting the incubator/upper tray (300) to the base having an partially transparent encasing (350), connected to an RF installable coil (380) on one side and a RF shield (101) on the other side, sized and shaped to sealingly enclose the MRD bore when at least a portion of the upper tray is housed within the open bore; Further the RF shield contains a conduit (310) configured to provide an RF shielding pass through for medical tubing. Further his view is showing the handle (70) that can also be embodied as any steering device such as steering wheel. The handle is further supported by a perpendicular rod like element (66) interconnecting the handle (70) with the base (85). The cart further is connected to a CPU having a user interface screen (400). Other optional placements for medical equipment can be the base (85) or the up stretching element (50) for infusion bags and such; this element can be telescopic, reversibly connecting, or maneuverable along a pivot point in the connection to the base (85), handle (70), or other part of the cart (800).

Figures 8C, 8D:
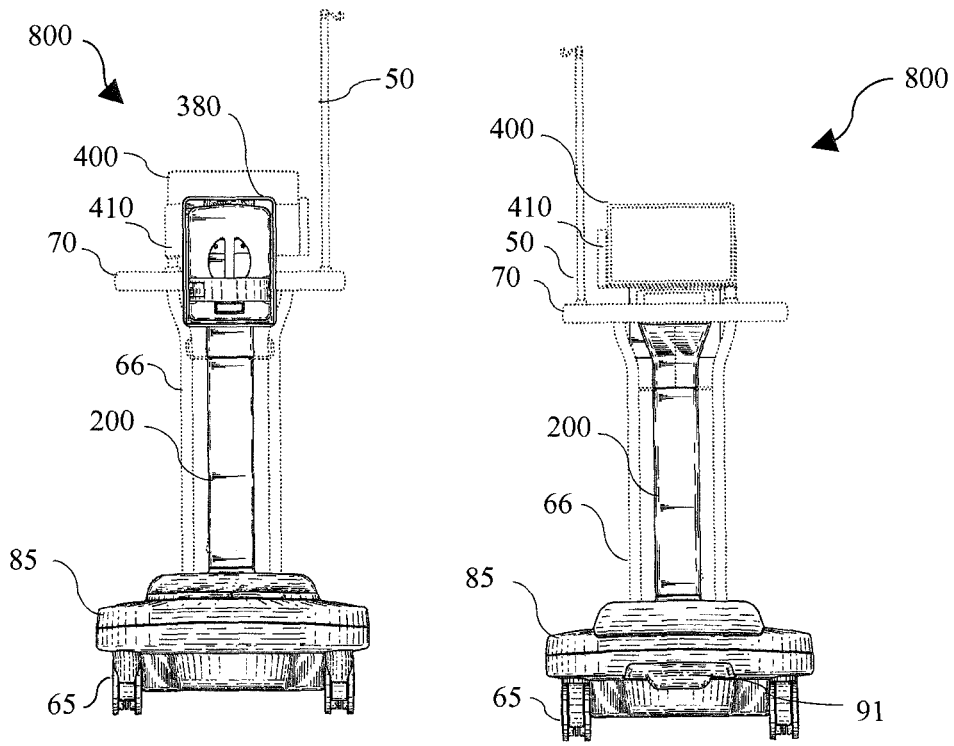
FIG. 8C is a schematic illustration of a cart in a back view.
FIG. 8D is a schematic illustration of a cart in a front view.

Reference is now made to FIG. 8C schematically illustrating, in an out of scale manner, an embodiment of the invention. A cart in a back view. A substantially horizontal base (85), connected to a motion enabling element such as a wheel (65), a pillar (200) interconnecting the base to an upper tray/incubator, connected to an RF installable coil (380). Further his view is showing the handle (70) that can also be embodied as any steering device such as steering wheel. The handle is further supported by a perpendicular rod like element (66) interconnecting the handle (70) with the base (85). The cart further is connected to a CPU (410) having a user interface screen (400). Other optional placements for medical equipment can be the base (85) or the up stretching element (50) for infusion bags and such; this element can be telescopic, reversibly connecting, or maneuverable along a pivot point in the connection to the base (85), handle (70), or other part of the cart (800).

Reference is now made to FIG. 8D schematically illustrating, in an out of scale manner, an embodiment of the invention. A cart in a front view. A substantially horizontal base (85), connected to a motion enabling element such as a wheel (65), interconnected by a pillar (200), to an upper tray integrated at least in part to an incubator. The base further comprises a lever (91) connected to a stopping mechanism of the wheels. Further his view is showing the handle (70) that can also be embodied as any steering device such as steering wheel. The handle is further supported by a perpendicular rod like element (66) interconnecting the handle (70) with the base (85). The cart further is connected to a CPU (410) having a user interface screen (400). Other optional placements for medical equipment can be the base (85) or the up stretching element (50) for infusion bags and such; this element can be telescopic, reversibly connecting, or maneuverable along a pivot point in the connection to the base (85), handle (70), or other part of the cart (800).

Figure 9A:
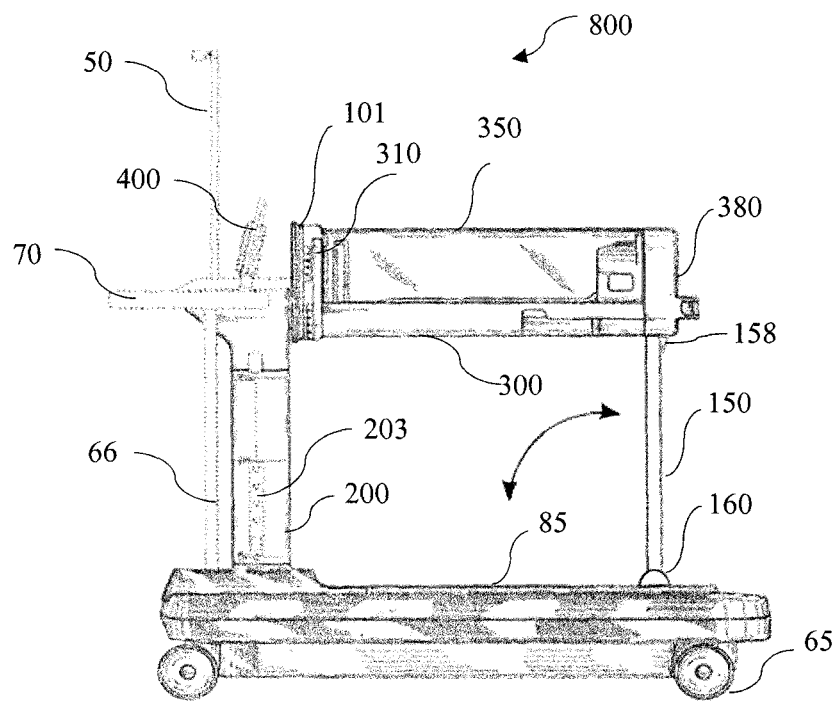
FIG. 9A is a schematic illustration of a cart, in a side view, in which a column is collapsible toward the cart base.

Reference is now made to FIG. 9A schematically illustrating, in an out of scale manner, an embodiment of the invention. A cart (800) in a side view. A substantially horizontal base (85), connected to a motion enabling element such as a wheel (65), interconnected by a pillar (200), having a port for electrical and medical tubing (203), to an upper tray (300) at least partially covered or enveloped by an MRI safe material creating an internal space (350) that can be embodied as an incubator, connected to an RF installable coil (380) on one side and a RF shield (101) on the other side, sized and shaped to sealingly enclose the MRD bore when at least a portion of the upper tray/incubator is housed within the open bore; Further the RF shield contains a conduit (310) configured to provide an RF shielding pass through for medical tubing. Further his view is showing the handle (70) that can also be embodied as any steering device such as steering wheel. The handle is further supported by a perpendicular rod like element (66) interconnecting the handle (70) with the base (85). The cart further is connected to a CPU having a user interface screen (400). Other optional placements for medical equipment can be the base (85) or the up stretching element (50) for infusion bags and such; this element can be telescopic, reversibly connecting, or maneuverable along a pivot point in the connection to the base (85), handle (70), or other part of the cart (800). The cart further comprise a collapsible retractable, reversibly connected column (150). In this embodiment the column is connected to the cart base (85) by a maneuverable connection (160) such as a hinge, providing movement of the column around the connection as a pivot point. The column (150) is configured to be normally deployed, thus in a relaxed position the column (150) is resting in a perpendicular position providing support for the upper tray/incubator (300) by leaning on the base (85). This position is further secured by a latching mechanism or stopping projection (158) connected to the upper tray (300) adjacent to the reversible connection of the column to the upper tray (300). The arrow describes the approximate movement path of the column (150) towards the base (85), when horizontal force is applied. This movement could be a consequence of the forces the front wall of the MRD envelope when applied during insertion of at least a portion of the cart to at least a portion of the MRD open bore and additionally or alternatively to the MRD recess. At the release of the applied force the column returns to a deployed position. Additionally or alternatively, the movement of the column (150) is automatic or manual. Further, the column (150) in a collapsed state is either embedded fully, partly, or not embedded to the plane to which it collapses to.

Figure 9B:
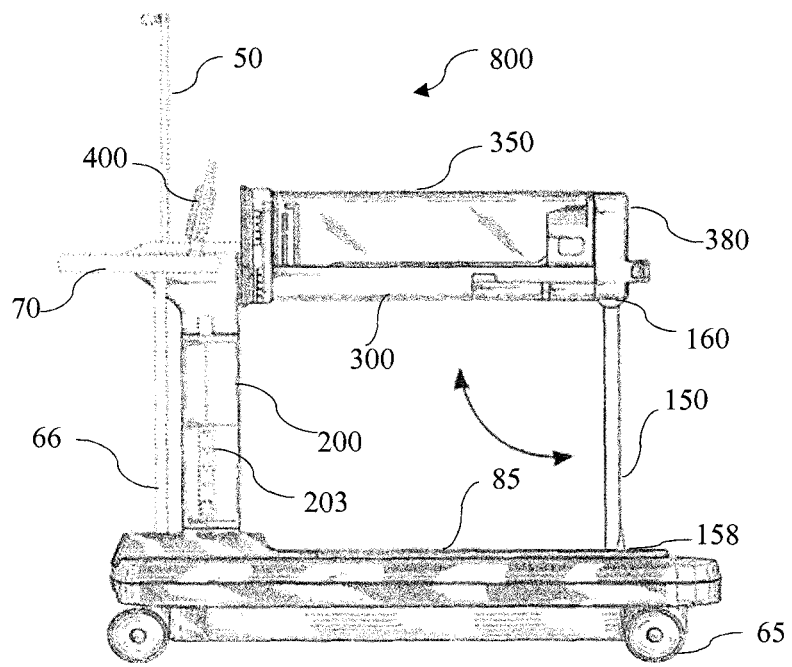
FIG. 9B is a schematic illustration of a cart, in a side view, in which a column is collapsible toward the cart upper tray.

Reference is now made to FIG. 9B schematically illustrating, in an out of scale manner, an embodiment of the invention. A cart (800) in a side view. A substantially horizontal base (85), connected to a motion enabling element such as a wheel (65), interconnected by a pillar (200), having a port for electrical and medical tubing (203), to an upper tray (300) having an envelope creating an enclosed space sized and shaped to accommodate a neonate (350), connected to an RF installable coil (380) on one side and a RF shield (101) on the other side, sized and shaped to sealingly enclose the MRD bore when at least a portion of the upper tray is housed within the open bore; Further the RF shield contains a conduit (310) configured to provide an RF shielding pass through for medical tubing. Further his view is showing the handle (70) that can also be embodied as any steering device such as steering wheel. The handle is further supported by a perpendicular rod like element (66) interconnecting the handle (70) with the base (85). The cart further is connected to a CPU having a user interface screen (400). Other optional placements for medical equipment can be the base (85) or the up stretching element (50) for infusion bags and such; this element can be telescopic, reversibly connecting, or maneuverable along a pivot point in the connection to the base (85), handle (70), or other part of the cart (800). The cart further comprise a collapsible retractable, reversibly connected column (150). In this embodiment the column is connected to the cart upper tray (300) by a maneuverable connection (160) such as a hinge, providing movement of the column around the connection as a pivot point. The column (150) is configured to be normally deployed, thus in a relaxed position the column (150) is resting in a perpendicular position providing support for the upper tray (300) by leaning on the base (85). This position is further secured by a latching mechanism or stopping projection (158) connected to the base adjacent to the reversible connection of the column to the base (85). The arrow describes the approximate movement path of the column (150) towards the upper tray (300), when horizontal force is applied. This movement could be a consequence of the forces the front wall of the MRD envelope when applied during insertion of at least a portion of the cart to at least a portion of the MRD open bore and additionally or alternatively to the MRD recess. At the release of the applied force the column returns to a deployed position. Additionally or alternatively, the movement of the column (150) is automatic or manual. Further, the column (150) in a collapsed state is either embedded fully, partly, or not embedded to the plane to which it collapses to.

Reference is now made to FIG. 10A schematically illustrating, in an out of scale manner, an embodiment of the invention. A cart (800), in a perspective view, in which a column (151) is of a fork like shape, collapsible toward the cart upper tray (300), having stoppers for securing the position of the column in a deployed position (158) for each connection point with the base (85). The arrow A presents an optional movement of the column fork protrusions towards each other, when collapsing in the direction indicated by arrow B.

Reference is now made to FIG. 10D schematically illustrating, in an out of scale manner, an embodiment of the invention. A cart (800), in a perspective view, in which a column (157) is of a non-geometric shape, collapsible toward the cart base (85). Further the column (157) is reversibly connected to the upper tray/incubator (300), while connected by a maneuverable connection (15) to the cart base (85).

Reference is now made to FIG. 10C schematically illustrating, in an out of scale manner, an embodiment of the invention. A cart (800), in a perspective view, in which a column (153) is of a fork like shape, collapsible toward the cart base (85). Further the column (153) is connected by a maneuverable connection such as a pivot point or a hinge to the cart base (85). The arrow A presents an optional movement of the column fork protrusions towards each other, when collapsing in the direction indicated by arrow B.

Figure 11A:
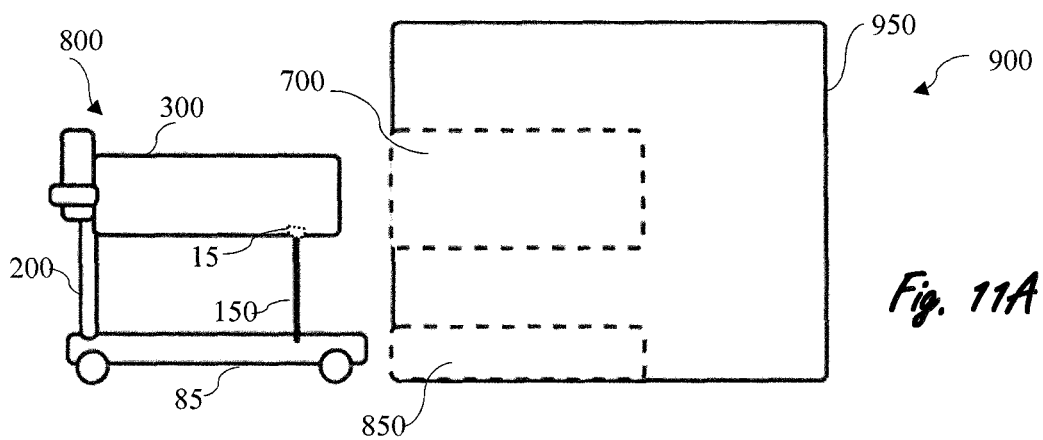
FIG. 11A is a schematic illustration of an MRS, in a side view, showing a cart having a collapsible column, and an MRD having an open bore and a recess.

Reference is now made to FIG. 11A schematically illustrating, in an out of scale manner, an embodiment of the invention. An MRS (900), in a side view, showing a cart (800) having a collapsible column (150), an incubator as an upper tray (300), interconnected and supported to a base (85) by a perpendicular pillar (200); Further the collapsible column (150) is connected by a maneuverable connection (15) to the upper tray/incubator (300); and an MRD (950)

having an open bore (700) and a recess (850). The normally deployed column (150) is in a resting position, interconnecting the base (85) with the upper tray (300).

Figure 11B:
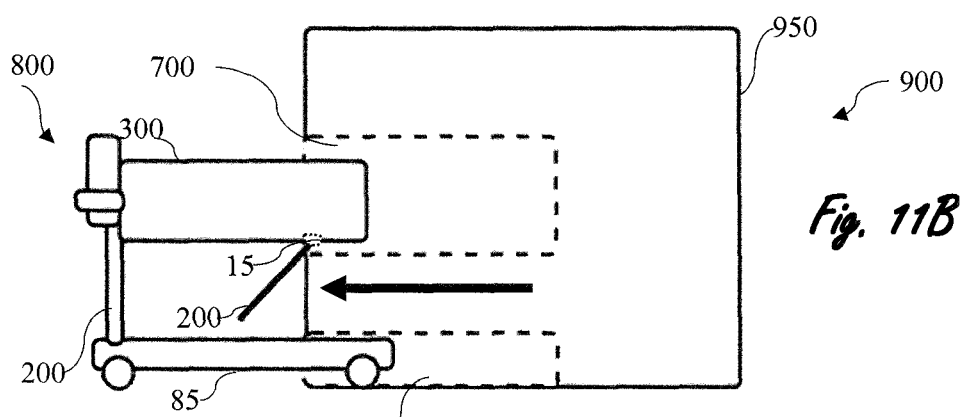
FIG. 11B is a schematic illustration of an MRS, in a side view, showing a cart having a collapsible column, and an MRD having an open bore and a recess.

Reference is now made to FIG. 11B schematically illustrating, in an out of scale manner, an embodiment of the invention. An MRS (900), in a side view, showing a cart (800) having a collapsible column (150), an incubator as an upper tray (300), interconnected and supported to a base (85) by a perpendicular pillar (200); Further the collapsible column (150) is connected by a maneuverable connection (15) to the upper tray embodied as an incubator (300); and an MRD (950) having an open bore (700) and a recess (850). When a horizontal force, as presented by the arrow, is applied to the normally deployed column (150), the column is at least partially collapsible towards the upper tray (300).

Figure 11C:
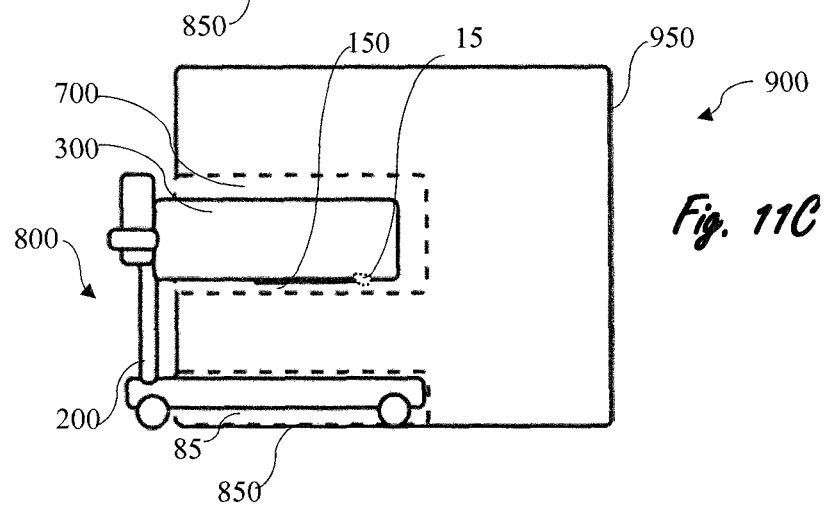
FIG. 11C is a schematic illustration of an MRS, in a side view, showing a cart having a collapsible column inserted at least partially into an MRD having an open bore and a recess.

Reference is now made to FIG. 11C schematically illustrating, in an out of scale manner, an embodiment of the invention. An MRS (900), in a side view, showing a cart (800) inserted at least partially into an MRD (950) open bore (700) and a recess (850), having a collapsible column (150) connected to the upper tray embodied as an incubator (300) by a maneuverable connection (15), partly embedded into the upper tray (300). The upper tray (300) is interconnected to the base (85) by a substantially perpendicular pillar (200).

Figure 12:
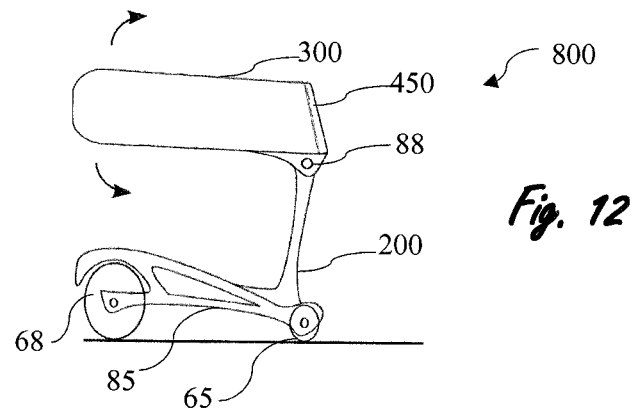
FIG. 12 is a schematic illustration of an MRI safe cart, in a side view, having an incubator upper tray maneuverably connected to the cart pillar.

Reference is now made to FIG. 12 schematically illustrating, in an out of scale manner, an embodiment of the invention. An MM safe cart (800), in a side view, having an incubator as an upper tray (300), in which a user interfaced including a display (450). The upper tray (300) is maneuverably connected (88) to the cart pillar (200). The maneuverable connection provides tilting of the upper tray (300) as indicated by the arrows. The pillar is further connected to a skeletal construction comprising the cart base (85) connected to elements providing movement such as wheels (68, 65).

Figure 13A:
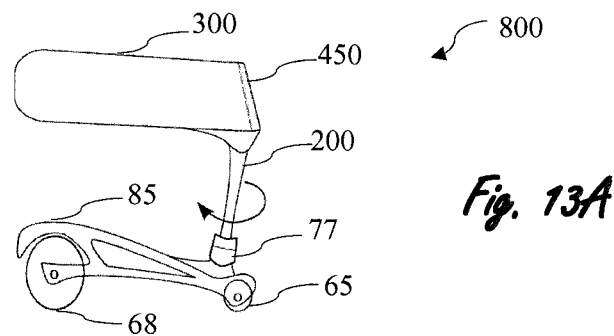
FIG. 13A is a schematic illustration of an MRI safe cart, in a side view, having an incubator upper tray connected to the cart pillar having a maneuverable connection providing rotational movement.

Reference is now made to FIG. 13A schematically illustrating, in an out of scale manner, an embodiment of the invention. An MM safe cart (800), in a side view, having an incubator as an upper tray (300), in which a user interfaced including a display (450). The upper tray (300) is connected to the cart pillar (200). The cart pillar (200) is maneuverably connected (77) to the base (85) providing rotational movement as depicted by the arrows. The base is a skeletal construction comprising elements providing movement such as wheels (68, 65).

Figure 13B:
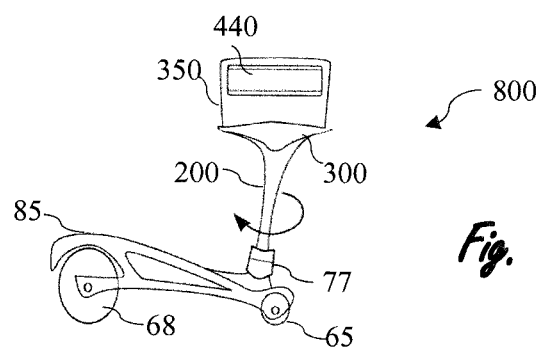
FIG. 13B is a schematic illustration of an MRI safe cart, in a side view, having an incubator upper tray connected to the cart pillar having a maneuverable connection providing rotational movement.

Reference is now made to FIG. 13B schematically illustrating, in an out of scale manner, an embodiment of the invention. An MM safe cart (800), in a side view, having an incubator as an embodiment of an upper tray (300). The incubator is formed by an envelope (350) at least partially surrounding an internal environment. Additionally or alternatively, this envelope contains at least one opening such as at least portion of the envelope connected by a hinge or a joint. Additionally or alternatively, this opening is configured to provide full or partial access to the neonate. Still referring to FIG. 13B, the cart comprises a user interfaced including a display (440). The upper tray (300) is connected to the cart pillar (200). The cart pillar (200) is maneuverably connected (77) to the base (85) providing rotational movement as depicted by the arrows. The base is a skeletal construction comprising elements providing movement such as wheels (68, 65). In this view the incubator is shown after it has been rotated to be with approximately 90 degree angle in reference to the base (85).

Reference is now made to FIG. 14A schematically illustrating, in an out of scale manner, an embodiment of the invention. An MRS (900), in a side view, showing a cart (800) having wheels (65) connected to a base (85), a rotational connected (77) pillar (200) connecting the base (85) to the upper tray (300), and an MRD (950) having an open bore (700) and a recess (830) that extends in approximately 90 degrees to the open bore (700).

Reference is now made to FIG. 14B schematically illustrating, in an out of scale manner, an embodiment of the invention. An MRS (900), in a side view, showing a cart (800) having wheels (65) connected to a base (85), a rotational connected (77) pillar (200) connecting the base (85) to the upper tray (300), and an MRD (950) having an open bore (700) and a recess (830) that extends in approximately 90 degrees to the open bore (700). The cart, at least partially inserted into at least a portion of an MRD open bore and a recess, when the upper tray (300) is rotated by approximately 90 degrees to the base (85).

Figure 15B:
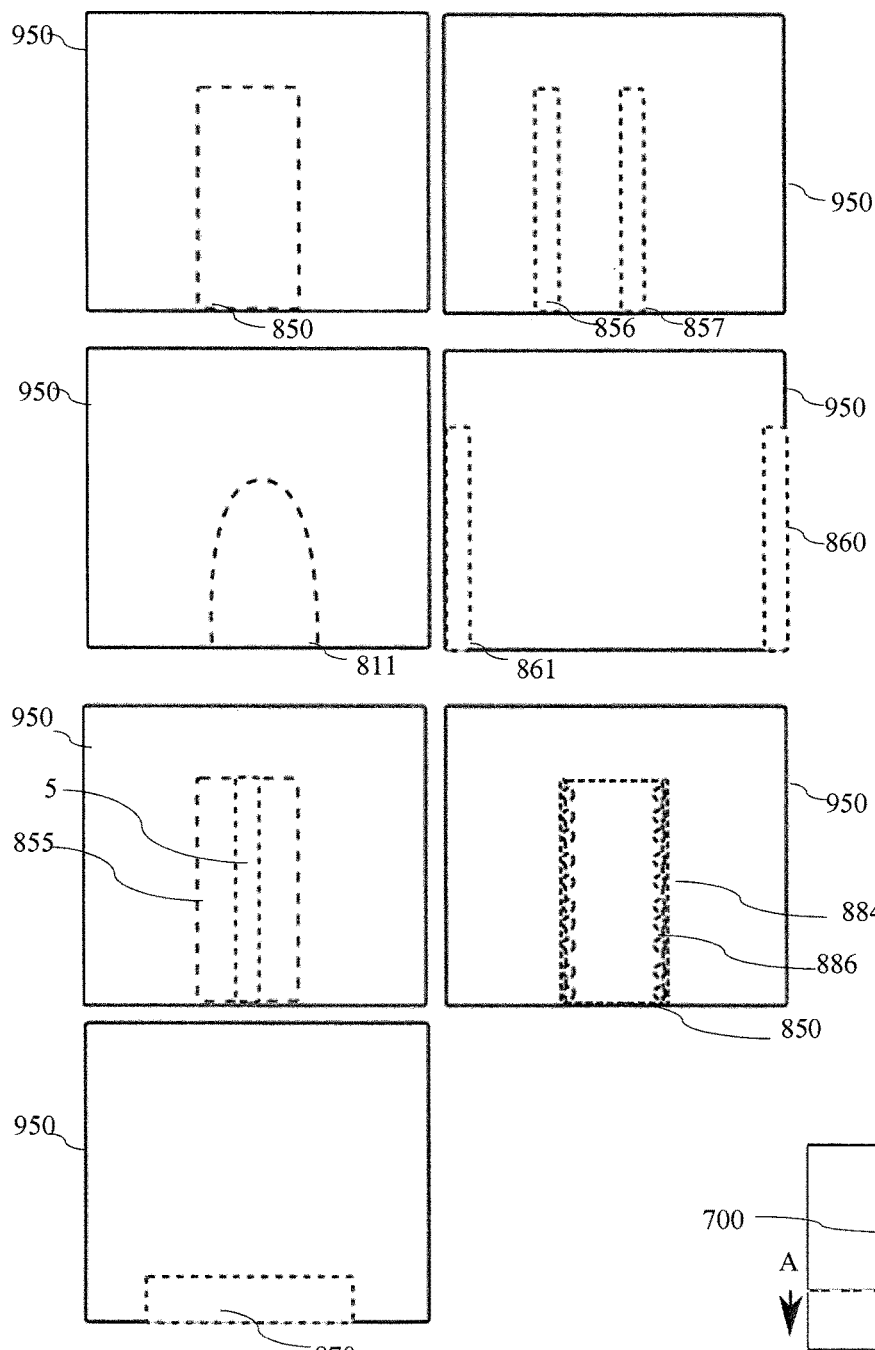
FIG. 15B is a schematic illustration of an MRD section in a top view, showing without limiting to, various embodiments of a recess in an MRD.
Figure 15A:
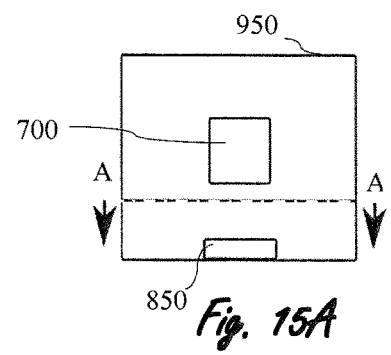
FIG. 15A is a schematic illustration of an MRD in a front view, showing the section cut of the top views in presented in FIG. 10B.

Reference is now made to FIG. 15A schematically illustrating, in an out of scale manner, an embodiment of the invention. An MRD (950) in a front view, having a recess (850) below the open bore (700) showing the section cut A-A of the top views directed downwards as indicated by the arrows, presented in FIG. 15B.

Reference is now made to FIG. 15B schematically illustrating, in an out of scale manner, an embodiment of the invention. An MRD (950) section in a top view, showing without limiting to, various embodiments of a recess (850) in an MRD (950). The recess is such as a curved shape (811), a rectangular shape (850), a single recess (850) a plurality of cavities (856, 857), a plurality of cavities located at the perimeter of the MRD (860,861), a parallel recess to the open bore (855, 850), a non-parallel to the open bore recess (870), a recess comprising a sliding mechanism (884) having rollers (886), a recess (855) comprising a single sliding track (5).

Figure 16:
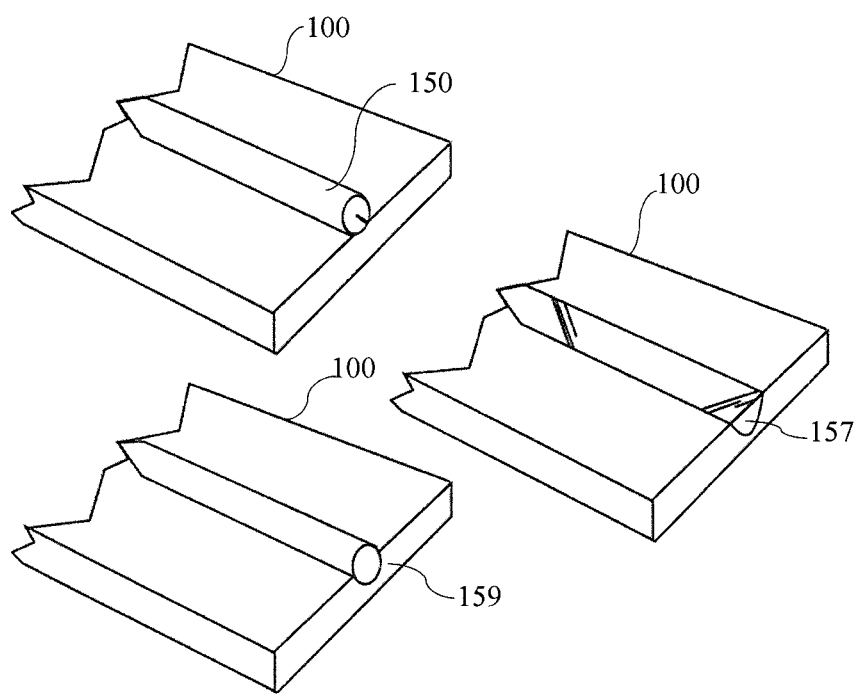
FIG. 16 is a schematic illustration of a column part.

Reference is now made to FIG. 16 schematically illustrating, in an out of scale manner, an embodiment of the invention. A column part (150) placed on top of the plane it tis collapsed to (100); a column part (157) completely embedded into the plane it is collapsing to (100); a column part at least partially embedded into the plane it is collapsing to (100).

Figure 17:
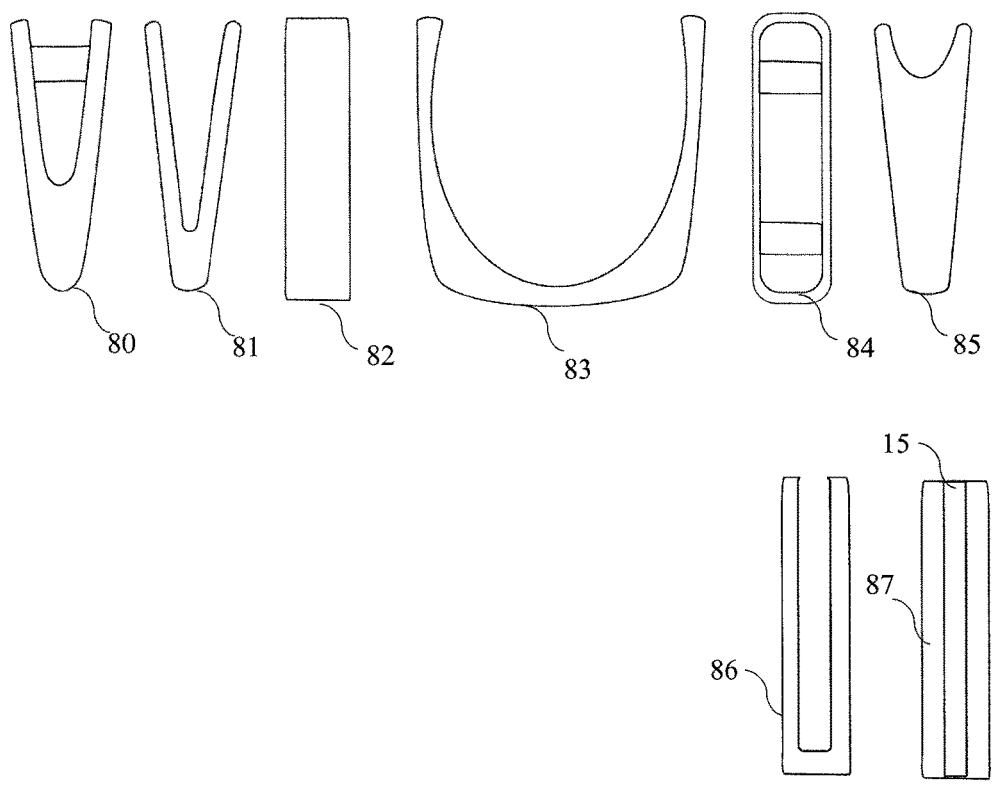
FIG. 17 is a schematic illustration of a cart base, showing without limiting to, various embodiments of the cart base shape.

Reference is now made to FIG. 17 schematically illustrating, in an out of scale manner, an embodiment of the invention. A cart base, showing without limiting to, various embodiments of the cart base shape, such as a skeletal shape (80), a fork like shape (81), a rectangular shape (82), an MRD embracing shape (83), a skeletal rectangular shape (84), a compound shape (85), a shape having more than one protrusion (86), a rectangular shape (87) shape having a top protrusion (15) insertable to a sliding rail.

According to one embodiment of the invention, an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD, and further wherein at least a portion of the cart's base is reversibly housed within at least one recess.

According to another embodiment of the invention, an MRI-safe cart as defined above is disclosed, wherein the MRD comprises a self-fastening cage surrounding a magnetic resonance device.

According to another embodiment of the invention, an MRI-safe cart as defined above is disclosed, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

According to another embodiment of the invention, an MRI-safe cart as defined above is disclosed, wherein the cart incubator is connected to the cart by a maneuverable connection enabling movement selected from a group consisting of: rotational, linear horizontal, linear vertical, tilting, oscillating movement, and any combination thereof.

According to another embodiment of the invention, an MRI-safe cart as defined above is disclosed, wherein the incubator is reversibly connected to the cart.

According to another embodiment of the invention, an MRI-safe cart as defined above is disclosed, wherein the cart comprises an MRI-incubator's closure assembly.

According to another embodiment of the invention, an MRI-safe cart as defined above is disclosed, wherein the cart is configured to sealingly enclose the MRD open bore when at least a portion thereof is housed within the MRD.

According to another embodiment of the invention, an MRI-safe cart as defined above is disclosed, wherein at least a portion of the MRS comprises a material selected from a group consisting of: MRI-safe material, sterilizable material, at least a partially transparent material, and any combination thereof.

According to another embodiment of the invention, an MRI-safe cart as defined above is disclosed, wherein the cart, the MRD or both, comprises a plurality of life supporting equipment, medical equipment placement, or both.

According to another embodiment of the invention, an MRI-safe cart as defined above is disclosed, wherein the cart pillar is maneuverably connected to the cart incubator, the cart base, or both.

According to another embodiment of the invention, an MRI-safe cart as defined above is disclosed, wherein the cart comprises at least one support, connecting the incubator to a selected from a group consisting of: the pillar, a wall, a transport device, the MRD, a storage unit, a floor and any combination thereof.

According to another embodiment of the invention, an MRI-safe cart as defined above is disclosed, wherein the cart pillar is reversibly connected to an element selected from a group consisting of: the cart upper tray, the cart base, at least one support, a least one storage unit, and any combination thereof.

According to another embodiment of the invention, an MRI-safe cart as defined above is disclosed, wherein the cart further comprises a reversibly collapsible column, useful for supporting the incubator, comprising an elongated member having at least two opposite ends, the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and, (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

According to another embodiment of the invention, an MRI-safe cart as defined above is disclosed, wherein the column is configured to be normally deployed.

According to another embodiment of the invention, an MRI-safe cart as defined above is disclosed, wherein the column is collapsible upon application of horizontal force in the axis parallel to the open bore.

According to another embodiment of the invention, an MRI-safe cart as defined above is disclosed, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

According to another embodiment of the invention, an MRI-safe cart as defined above is disclosed, wherein the at least one column end is reversibly connectable to at least two locations selected from a group consisting of: the cart base, the cart upper tray, the cart pillar, a storage unit, a wall, a transport device, and any combination thereof.

According to another embodiment of the invention, an MRI-safe cart as defined above is disclosed, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

According to another embodiment of the invention, an MRI-safe cart as defined above is disclosed, wherein the column is at least partially reversibly collapsible into or onto an element selected from a group consisting of: the base, the upper tray, the pillar, when the cart is at least partially intercepted within the MRD.

According to another embodiment of the invention, an MRI-safe cart as defined above is disclosed, wherein the column is at least partially reversibly collapsible into or onto an element selected from a group consisting of: the base, the upper tray, the pillar, when force is applied on the column.

According to another embodiment of the invention, an MRI-safe cart as defined above is disclosed, wherein the column is at least partially embedded within a selected from a group consisting of: the base, the upper tray, the pillar, or any combination thereof, when in folded or collapsible positions.

According to another embodiment of the invention, an MRI-safe cart as defined above is disclosed, wherein the column comprises a telescopic or folding mechanism, thereby enabling different length of the column.

According to another embodiment of the invention, an MRI-safe cart as defined above is disclosed, wherein the at least apportion of the column is made of a material selected from a group consisting of: MRI-safe material, recyclable material, sterilizable material, fire retardant material, and any combination thereof.

According to another embodiment of the invention, an MRI-safe cart as defined above is disclosed, wherein the column is of a shape selected from a group consisting of:

rod, cylinder, multifaceted shape, rectangular, geometric, non-geometric, curved, compound shape, fork-like, and any combination thereof.

According to another embodiment of the invention, an MRI-safe cart as defined above is disclosed, wherein the column maintains stability of the upper tray in a horizontal or reclined position.

According to another embodiment of the invention, an MRI-safe cart as defined above is disclosed, wherein a selected from a group consisting of: the column, the MRD, the cart and any combination thereof, comprises at least one latching mechanism configured to hold at least one first position of the column.

According to another embodiment of the invention, an MRI-safe cart as defined above is disclosed, wherein the cart base is of a fork like shape, having a recess sized and fitted to house the at least a portion of the MRD.

According to another embodiment of the invention, an MRI-safe cart as defined above is disclosed, wherein the cart's base comprises at least one protrusion sized and shaped to be inserted at least partially into or under the MRD.

According to another embodiment of the invention, an MRI-safe cart as defined above is disclosed, wherein the MRD comprises an envelope at least partially encasing the MRD, and at least one recess in the circumference of the envelope sized and shaped to accept at least a portion of the cart.

According to another embodiment of the invention, an MRI-safe cart as defined above is disclosed, wherein the at least one recess is selected from a group consisting of: parallel to the open bore, perpendicular to the open bore, in an angle to the open bore, and any combination thereof.

According to another embodiment of the invention, an MRI-safe cart as defined above is disclosed, wherein the recess is sized and shaped as a mold of at least a portion of the cart. According to another embodiment of the invention, an MRI-safe cart as defined above is disclosed, wherein the recess comprises a rail or track along which the base is at least partially housed.

According to another embodiment of the invention, an MRI-safe cart as defined above is disclosed, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

According to another embodiment of the invention, an MRI-safe cart as defined above is disclosed, wherein the MRD comprises a selected from a group consisting of: a sliding mechanism, a rail, a guide, and any combination thereof configured to slide the cart at least partially into the MRD.

According to another embodiment of the invention, an MRI-safe cart as defined above is disclosed, wherein the track comprises wheels or rollers.

According to another embodiment of the invention, an MRI-safe cart as defined above is disclosed, wherein the movement of the cart into the MRD is controlled by a mechanism selected from a group consisting of: manual, automatic or any combination thereof.

According to another embodiment of the invention, an MRI-safe cart as defined above is disclosed, wherein the MRD, the cart, or both comprise an emergency release mechanism, to extract the neonate accommodated within.

According to another embodiment of the invention, an MRI-safe cart as defined above is disclosed, wherein the MRD, the cart or both comprise a lighting system.

According to another embodiment of the invention, an MRI-safe cart as defined above is disclosed, wherein the cart comprises an RF shielding conduit sized and shaped for the passage of medical equipment tubing.

According to another embodiment of the invention, an MRI-safe cart as defined above is disclosed, wherein the cart, the MRD or both, comprises a plurality of medical equipment, medical equipment placing, or both.

According to another embodiment of the invention, an MRI-safe cart as defined above is disclosed, wherein the cart, the MRD or both, comprises an RF detection mechanism.

According to another embodiment of the invention, an MRI-safe cart as defined above is disclosed, wherein the cart, the MRD or both, comprises at least one handle.

According to another embodiment of the invention, an MRI-safe cart as defined above is disclosed, wherein at least a portion of the cart is foldable thereby minimizing storage space.

According to another embodiment of the invention, an MRI-safe cart as defined above is disclosed, wherein at least a portion of the cart is constructed of modular reversibly connecting pieces.

According to another embodiment of the invention, an MRI-safe cart as defined above is disclosed, wherein the pillar is sized and shaped to provide structural support to the incubator situated in a substantially horizontal plain parallel to the base.

According to another embodiment of the invention, an MRI-safe cart as defined above is disclosed, wherein the pillar is reversibly connected to an element selected from a group consisting of the incubator, the base, at least one support, a least one storage unit and any combination thereof.

According to another embodiment of the invention, an MRI-safe cart as defined above is disclosed, wherein the pillar is of a fork like shape having at least two connecting points to the upper tray, the base or both.

According to another embodiment of the invention, an MRI-safe cart as defined above is disclosed, wherein the pillar is of a shape selected from a group consisting of cylindered, quadrangular, geometrical, none geometrical, multifaceted shape, smooth-lined shape, compound shape comprised of multiple pieces, and any combination thereof.

According to another embodiment of the invention, an MRI-safe cart as defined above is disclosed, wherein the pillar is telescopic configured to provide an adjustable height of the patient's bed.

According to another embodiment of the invention, an MRI-safe cart as defined above is disclosed, wherein the pillar is connected to the base, the upper tray or both, by a rotating mechanism.

According to another embodiment of the invention, an MRI-safe cart as defined above is disclosed, wherein the pillar is rotated together with the upper tray or with the base.

According to another embodiment of the invention, an MRI-safe cart as defined above is disclosed, wherein the pillar is at least partially hollow and comprises a conduit sized and shaped for the passage of medical equipment tubing.

According to another embodiment of the invention, an MRI-safe cart as defined above is disclosed, wherein the pillar is further connected to at least one storage tray, at least one storage unit or both.

According to another embodiment of the invention, an MRI-safe cart as defined above is disclosed, wherein the cart's base comprises at least one wheel.

According to another embodiment of the invention, an MRI-safe cart as defined above is disclosed, wherein the cart comprises a motion stopping mechanism, e.g. wheel brakes.

According to another embodiment of the invention, an MRI-safe cart as defined above is disclosed, wherein the cart's base is substantially of a shape selected from a group consisting of: rectangle, oval, round, triangular, geometric, none geometric, multifaceted, having smooth rounded edges, compound shape, a hollow frame, a shape frame and any combination thereof.

According to another embodiment of the invention, an MRI-safe cart as defined above is disclosed, wherein the upper tray or incubator is substantially of a shape selected from a group consisting of: rectangle, a cube, a sphere, box, egg like, oval, round, triangular, geometric, none geometric, multifaceted, having smooth rounded edges, compound shape, a hollow frame, a shape frame and any combination thereof.

According to another embodiment of the invention, an MRI-safe cart as defined above is disclosed, wherein the cart, the MRD or both comprise a user interface.

According to another embodiment of the invention, an MRI-safe cart as defined above is disclosed, wherein the cart, the MRD or both comprising a CPU connected to a user interface.

According to another embodiment of the invention, an MRI-safe cart as defined above is disclosed, wherein the cart user interface is configured to control the MRD operating system.

According to another embodiment of the invention, an MRI-safe cart as defined above is disclosed, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

According to another embodiment of the invention, an MRI-safe cart as defined above is disclosed, wherein the sensor is connected to a selected from a group consisting of: a sensible indicator, a visual indicator, an auditable indicator, a CPU, a user interface, a control panel, According to another embodiment of the invention, an MRI-safe cart as defined above is disclosed, wherein the cart comprises an installable RF coil assembly.

According to another embodiment of the invention, an MRI-safe cart as defined above is disclosed, wherein the cart comprising a comprising at least one RF shielding conduit, connected to the cart; sized and shaped to allow passage of medical equipment tubing from the MRD bore to the external environment; further wherein the conduit is characterized by a length (l) and a width (w) l:w ratio is greater than a predefined value n, thereby providing RF shielding; where the numerical value of n is selected from a group consisting of: $2.5 < n < 6$, $4 < n < 6$, $4 < n < 9$ and any combination thereof.

According to another embodiment of the invention, an MRI-safe cart as defined above is disclosed, wherein the MRD open bore is of a shape selected from a group consisting of: cylindered, quadrangular, geometrical, none geometrical, multifaceted shape, smooth-lined shape, and any combination thereof.

According to one embodiment of the invention a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one second end reversibly connected to a selected from a group consisting of: the cart base, the cart pillar, a storage unit, a transport device, a wall, the floor, an imaging apparatus, a treatment table, and any combination thereof; and (b) at least one first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

According to another embodiment of the invention, a reversibly collapsible column as defined above is disclosed, wherein the cart comprises at least one selected from a group consisting of: an incubator, a deployable incubator, a transport incubator, a thermo isolating incubator, a patient bed, a treatment table, a gurney, a tray, a patient placement, a patient chair, a noise isolating patient placement, a vibration isolating patient placement, a stretcher, a carrying bed, an ergonomic patient placement, a patient restraint, and any combination thereof.

According to another embodiment of the invention, a reversibly collapsible column as defined above is disclosed, wherein the cart incubator is connected to the cart by a maneuverable connection enabling movement selected from a group consisting of: rotational, linear horizontal, linear vertical, tilting, oscillating movement, and any combination thereof.

According to another embodiment of the invention, a reversibly collapsible column as defined above is disclosed, wherein the incubator is reversibly connected to the cart.

According to another embodiment of the invention, a reversibly collapsible column as defined above is disclosed, wherein the cart comprises an MRI-incubator's closure assembly.

According to another embodiment of the invention, a reversibly collapsible column as defined above is disclosed, wherein the cart is configured to sealingly enclose the MRD open bore when at least a portion thereof is housed within the MRD.

According to another embodiment of the invention, a reversibly collapsible column as defined above is disclosed, wherein at least a portion of the MRS comprises a material selected from a group consisting of: MRI-safe material, sterilizable material, at least a partially transparent material, and any combination thereof.

According to another embodiment of the invention, a reversibly collapsible column as defined above is disclosed, wherein the cart, the MRD or both, comprises a plurality of life supporting equipment, medical equipment placement, or both.

According to another embodiment of the invention, a reversibly collapsible column as defined above is disclosed, wherein the cart pillar is maneuverably connected to the cart incubator, the cart base, or both.

According to another embodiment of the invention, a reversibly collapsible column as defined above is disclosed, wherein the cart comprises at least one support, connecting the incubator to a selected from a group consisting of: the pillar, a wall, a transport device, the MRD, a storage unit, a floor and any combination thereof.

According to another embodiment of the invention, a reversibly collapsible column as defined above is disclosed, wherein the cart pillar is reversibly connected to an element selected from a group consisting of: the cart upper tray, the cart base, at least one support, a least one storage unit, and any combination thereof.

According to another embodiment of the invention, a reversibly collapsible column as defined above is disclosed, wherein the column is configured to be normally deployed.

According to another embodiment of the invention, a reversibly collapsible column as defined above is disclosed, wherein the column is collapsible upon application of horizontal force in the axis parallel to the open bore.

According to another embodiment of the invention, a reversibly collapsible column as defined above is disclosed, wherein the column is maneuverably connected to the cart by a mechanism select from a group consisting of: a hinge, a bearing, a pivot point, a sliding mechanism, a rail, a telescopic mechanism, a magnetic connection, a flexible material, and any combination thereof.

It is another object of the current invention to disclose the MRS defined in any of the above, wherein the at least one column end is reversibly connectable to at least two locations selected from a group consisting of: the cart base, the cart upper tray, the cart pillar, a storage unit, a wall, a transport device, and any combination thereof.

According to another embodiment of the invention, a reversibly collapsible column as defined above is disclosed, wherein the column at least two reversibly connecting locations are configured to provide the cart incubator with a position selected from a group consisting of: at least one first supporting position, at least one horizontal position, at least one first angled position, at least one first folded position, at least one first collapsed position, and any combination thereof, relative to the first incubator position.

According to another embodiment of the invention, a reversibly collapsible column as defined above is disclosed, wherein the column is at least partially reversibly collapsible into or onto an element selected from a group consisting of: the base, the upper tray, the pillar, when the cart is at least partially intercepted within the MRD.

According to another embodiment of the invention, a reversibly collapsible column as defined above is disclosed, wherein the column is at least partially reversibly collapsible into or onto an element selected from a group consisting of: the base, the upper tray, the pillar, when force is applied on the column.

According to another embodiment of the invention, a reversibly collapsible column as defined above is disclosed, wherein the column is at least partially embedded within a selected from a group consisting of: the base, the upper tray, the pillar, or any combination thereof, when in folded or collapsible positions.

According to another embodiment of the invention, a reversibly collapsible column as defined above is disclosed, wherein the column comprises a telescopic or folding mechanism, thereby enabling different length of the column.

According to another embodiment of the invention, a reversibly collapsible column as defined above is disclosed, wherein the at least apportion of the column is made of a material selected from a group consisting of: MRI-safe material, recyclable material, sterilizable material, fire retardant material, and any combination thereof.

According to another embodiment of the invention, a reversibly collapsible column as defined above is disclosed, wherein the column is of a shape selected from a group consisting of: rod, cylinder, multifaceted shape, rectangular, geometric, non-geometric, curved, compound shape, fork-like, and any combination thereof.

According to another embodiment of the invention, a reversibly collapsible column as defined above is disclosed, wherein the column maintains stability of the upper tray in a horizontal or reclined position.

According to another embodiment of the invention, a reversibly collapsible column as defined above is disclosed, wherein a selected from a group consisting of: the column, the MRD, the cart and any combination thereof, comprises at least one latching mechanism configured to hold at least one first position of the column.

According to another embodiment of the invention, a reversibly collapsible column as defined above is disclosed, wherein the cart base is of a fork like shape, having a recess sized and fitted to house the at least a portion of the MRD.

According to another embodiment of the invention, a reversibly collapsible column as defined above is disclosed, wherein the cart's base comprises at least one protrusion sized and shaped to be inserted at least partially into or under the MRD.

According to another embodiment of the invention, a reversibly collapsible column as defined above is disclosed, wherein the MRD comprises an envelope at least partially encasing the MRD, and at least one recess in the circumference of the envelope sized and shaped to accept at least a portion of the cart.

According to another embodiment of the invention, a reversibly collapsible column as defined above is disclosed, wherein the at least one recess is selected from a group consisting of: parallel to the open bore, perpendicular to the open bore, in an angle to the open bore, and any combination thereof.

According to another embodiment of the invention, a reversibly collapsible column as defined above is disclosed, wherein the recess is sized and shaped as a mold of at least a portion of the cart.

According to another embodiment of the invention, a reversibly collapsible column as defined above is disclosed, wherein the recess comprises a rail or track along which the base is at least partially housed.

According to another embodiment of the invention, a reversibly collapsible column as defined above is disclosed, comprising at least one latching mechanism securing the cart in an at least one position selected from a group consisting of: at least partially housed position within the MRD, at least partly housed position in a storage device, at least partially housed in a treatment apparatus, in a stand-alone position and any combination thereof.

According to another embodiment of the invention, a reversibly collapsible column as defined above is disclosed, wherein the MRD comprises a selected from a group consisting of: a sliding mechanism, a rail, a guide, and any combination thereof configured to slide the cart at least partially into the MRD.

According to another embodiment of the invention, a reversibly collapsible column as defined above is disclosed, wherein the track comprises wheels or rollers.

According to another embodiment of the invention, a reversibly collapsible column as defined above is disclosed, wherein the movement of the cart into the MRD is controlled by a mechanism selected from a group consisting of: manual, automatic or any combination thereof.

According to another embodiment of the invention, a reversibly collapsible column as defined above is disclosed, wherein the MRD, the cart, or both comprise an emergency release mechanism, to extract the neonate accommodated within.

According to another embodiment of the invention, a reversibly collapsible column as defined above is disclosed, wherein the MRD, the cart or both comprise a lighting system.

According to another embodiment of the invention, a reversibly collapsible column as defined above is disclosed, wherein the cart comprises an RF shielding conduit sized and shaped for the passage of medical equipment tubing.

According to another embodiment of the invention, a reversibly collapsible column as defined above is disclosed, wherein the cart, the MRD or both, comprises a plurality of medical equipment, medical equipment placing, or both.

According to another embodiment of the invention, a reversibly collapsible column as defined above is disclosed, wherein the cart, the MRD or both, comprises an RF detection mechanism.

According to another embodiment of the invention, a reversibly collapsible column as defined above is disclosed, wherein the cart, the MRD or both, comprises at least one handle.

According to another embodiment of the invention, a reversibly collapsible column as defined above is disclosed, wherein at least a portion of the cart is foldable thereby minimizing storage space.

According to another embodiment of the invention, a reversibly collapsible column as defined above is disclosed, wherein at least a portion of the cart is constructed of modular reversibly connecting pieces.

According to another embodiment of the invention, a reversibly collapsible column as defined above is disclosed, wherein the pillar is sized and shaped to provide structural support to the incubator situated in a substantially horizontal plain parallel to the base.

According to another embodiment of the invention, a reversibly collapsible column as defined above is disclosed, wherein the pillar is reversibly connected to an element selected from a group consisting of the incubator, the base, at least one support, a least one storage unit and any combination thereof.

According to another embodiment of the invention, a reversibly collapsible column as defined above is disclosed, wherein the pillar is of a fork like shape having at least two connecting points to the upper tray, the base or both.

According to another embodiment of the invention, a reversibly collapsible column as defined above is disclosed, wherein the pillar is of a shape selected from a group consisting of cylindered, quadrangular, geometrical, none geometrical, multifaceted shape, smooth-lined shape, compound shape comprised of multiple pieces, and any combination thereof.

According to another embodiment of the invention, a reversibly collapsible column as defined above is disclosed, wherein the pillar is telescopic configured to provide an adjustable height of the patient's bed.

According to another embodiment of the invention, a reversibly collapsible column as defined above is disclosed, wherein the pillar is connected to the base, the upper tray or both, by a rotating mechanism.

According to another embodiment of the invention, a reversibly collapsible column as defined above is disclosed, wherein the pillar is rotated together with the upper tray or with the base.

According to another embodiment of the invention, a reversibly collapsible column as defined above is disclosed, wherein the pillar is at least partially hollow and comprises a conduit sized and shaped for the passage of medical equipment tubing.

According to another embodiment of the invention, a reversibly collapsible column as defined above is disclosed, wherein the pillar is further connected to at least one storage tray, at least one storage unit or both.

According to another embodiment of the invention, a reversibly collapsible column as defined above is disclosed, wherein the cart's base comprises at least one wheel.

According to another embodiment of the invention, a reversibly collapsible column as defined above is disclosed, wherein the cart comprises a motion stopping mechanism, e.g. wheel brakes.

According to another embodiment of the invention, a reversibly collapsible column as defined above is disclosed, wherein the cart's base is substantially of a shape selected from a group consisting of: rectangle, oval, round, triangular, geometric, none geometric, multifaceted, having smooth rounded edges, compound shape, a hollow frame, a shape frame and any combination thereof.

According to another embodiment of the invention, a reversibly collapsible column as defined above is disclosed, wherein the upper tray or incubator is substantially of a shape selected from a group consisting of: rectangle, a cube, a sphere, box, egg like, oval, round, triangular, geometric, none geometric, multifaceted, having smooth rounded edges, compound shape, a hollow frame, a shape frame and any combination thereof.

According to another embodiment of the invention, a reversibly collapsible column as defined above is disclosed, wherein the cart, the MRD or both comprise a user interface.

According to another embodiment of the invention, a reversibly collapsible column as defined above is disclosed, wherein the cart, the MRD or both comprising a CPU connected to a user interface.

According to another embodiment of the invention, a reversibly collapsible column as defined above is disclosed, wherein the cart user interface is configured to control the MRD operating system.

According to another embodiment of the invention, a reversibly collapsible column as defined above is disclosed, wherein the MRD, cart or both comprise at least one sensor configured to sense a selected from a group consisting of: neonate's physical condition, structural integrity of the MRD, structural integrity of the cart, structural integrity of the incubator, operation of life supporting equipment, location of the cart relative to the MRD, RF signal transmitted, RF signal received, temperature, smoke, gas concentration, humidity, movement, sound, light, presence of a metallic object, and any combination thereof.

According to another embodiment of the invention, a reversibly collapsible column as defined above is disclosed, wherein the sensor is connected to a selected from a group consisting of: a sensible indicator, a visual indicator, an auditable indicator, a CPU, a user interface, a control panel, According to another embodiment of the invention, a reversibly collapsible column as defined above is disclosed, wherein the cart comprises an installable RF coil assembly.

According to another embodiment of the invention, a reversibly collapsible column as defined above is disclosed, wherein the cart comprising a comprising at least one RF shielding conduit, connected to the cart; sized and shaped to allow passage of medical equipment tubing from the MRD bore to the external environment; further wherein the conduit is characterized by a length (l) and a width (w) l:w ratio is greater than a predefined value n, thereby providing RF shielding; where the numerical value of n is selected from a group consisting of: $2.5<n<6$, $4<n<6$, $4<n<9$ and any combination thereof.

According to another embodiment of the invention, a reversibly collapsible column as defined above is disclosed, wherein the MRD open bore is of a shape selected from a group consisting of: cylindered, quadrangular, geometrical, none geometrical, multifaceted shape, smooth-lined shape, and any combination thereof.

FIGS. 1-12 further enable a magnetic resonance system (MRS), useful for imaging a patient, comprising: (a) a magnetic resonance device (MRD) for imaging a patient, comprising an open bore, the MRD at least partially contained in an envelope comprising in its circumference at least one recess; and, (b) an MRI-safe cart made of MRI-safe material, comprising a substantially horizontal base and at least one substantially horizontal incubator above the base, the base and the incubator are interconnected by at least one pillar, wherein at least a portion of the cart and the MRD are configured to fit together such that at least a portion of the incubator is reversibly housed within the MRD, and further wherein at least a portion of the base is reversibly housed within at least one recess.

FIGS. 1-12 further enable a magnetic resonance device (MRD), useful for imaging a patient, at least partially contained in an envelope comprising an open bore, and at least one recess in the circumference of the envelope, wherein the MRD is configured to fit at least partially an MRI safe cart, made of MM-safe material, comprising a substantially horizontal base, and at least one substantially horizontal incubator above the base, interconnected by at least one pillar such that at least a portion of the cart's incubator is reversibly housed within the MRD, and at least a portion of the cart's base is reversibly housed within at least one recess.

FIGS. 1-12 further enable an MRI-safe cart, made of MRI-safe material, useful for imaging a patient with a magnetic resonance device (MRD), comprising a substantially horizontal base and at least one substantially horizontal incubator above the base, the base and the incubator are interconnected by at least one pillar; the MRD at least partially contained in an envelope comprising an open bore, and at least one recess in the circumference of the envelope; wherein the MRI-safe cart is configured to fit the MRD, such that at least a portion of the cart's incubator is reversibly housed within the MRD, and further wherein at least a portion of the cart's base is reversibly housed within at least one recess.

FIGS. 1-12 further enable a reversibly collapsible column, useful for supporting an incubator in connection with an MRI-safe cart, made of MRI-safe material, comprising a substantially horizontal base, and at least one substantially horizontal incubator above the base, interconnected by at least one pillar, the cart is configured to fit at least partially a magnetic resonance device (MRD), at least partially contained in an envelope comprising an open bore, and at least one recess in the circumference of the envelope, the column comprising an elongated member having at least two opposite ends; the column is selected from at least one member of a group consisting of: (a) at least one first end is maneuverably connected to the incubator, at least one the second end reversibly connected to a selected from a group consisting of: the cart base, the cart pillar, a storage unit, a transport device, a wall, the floor, an imaging apparatus, a treatment table, and any combination thereof and (b) at least one the first end is maneuverably connected to a selected from a group consisting of: the cart base, the cart pillar, a storage unit, a transport device, a wall, the floor, an imaging apparatus, a treatment table, and any combination thereof, at least one second end reversibly connected to the incubator, wherein at least a portion of the column is reversibly collapsible when the cart is at least partially intercepted within a selected from a group consisting of: the MRD, a storage apparatus, a transport device, a treatment table, an imaging apparatus, and any combination thereof.

The invention claimed is:

1. A magnetic resonance system (MRS), the system comprising:
    a. a magnetic resonance device (MRD) for imaging a patient, comprising an open bore, said MRD at least partially contained in an envelope comprising at least one recess below said open bore; and
    b. an magnetic resonance imaging (MRI)-safe cart made of MRI-safe material, comprising a horizontal base and an incubator above said base for accommodating a patient, said base and said incubator are interconnected by at least one pillar and said base comprising at least one two wheels;
    wherein said open bore is sized and shaped to accept said incubator and said recess is sized and shaped to accept said base such that when said cart is transported to said MRD for imaging said patient, said incubator is reversibly housed within said open bore and said base is reversibly housed within said at least one recess; and
    wherein said incubator comprises a first end and a second end, the second end coupled to an radio frequency (RF) shield, the RF shield configured to close said open bore when said incubator is inserted into said MRD and said incubator is housed within said MRD.

2. The MRS according to claim 1, wherein said pillar is a telescopic pillar configured to provide an adjustable height of said incubator.

3. The MRS according to claim 1, wherein said RF shield comprises a conduit configured to provide an RF shielding pass for medical tubing.

4. The MRS of claim 3 wherein said conduit of said RF shield has a length to width ratio that is greater than a predefined value n, wherein n is between 2.5 and 9.

5. The MRS of claim 3 wherein said conduit of said RF shield has a length to width ratio that is 5 to 1.

6. The MRS according to claim 1, wherein said pillar is at least partially hollow and comprises a conduit sized and shaped for passage of medical equipment tubing and/or electric current connection through said pillar to said incubator.

7. The MRS according to claim 1, wherein said cart further comprises a reversibly collapsible column, useful for supporting said incubator, said column is configured to be reversibly collapsible when the incubator is inserted inside into said open bore.

8. The MRS according to claim 7, wherein said column has at least two opposite ends and wherein:
   a. at least one of said at least two opposite ends is maneuverably connected to said incubator, and at least one second opposite end is reversibly connected to said said base; or
   b. at least one of said at least two opposite ends is maneuverably connected to said base and at least one second opposite end is reversibly connected to said incubator.

9. The MRS according to claim 7, wherein at least one of the following is held true:
   a. said column is collapsible upon application of horizontal force in an axis parallel to said open bore;
   b. said column is at least partially reversibly collapsible into or onto an element selected from a group consisting of: said base, said upper tray, said pillar, or any combination thereof, when said cart is at least partially intercepted within said MRD; and,
   c. said column is made of MRI-safe material.

10. The MRS of claim 1 wherein said first end of said incubator is coupled to an RF coil assembly.

* * * * *